US012595470B2

(12) United States Patent
Hekele et al.

(10) Patent No.: US 12,595,470 B2
(45) Date of Patent: Apr. 7, 2026

(54) ENGINEERED NUCLEASES THAT TARGET HUMAN AND CANINE FACTOR VIII GENES AS A TREATMENT FOR HEMOPHILIA A

(71) Applicant: Precision BioSciences, Inc., Durham, NC (US)

(72) Inventors: Armin Hekele, Cary, NC (US); Clayton Beard, Durham, NC (US); Derek Jantz, Durham, NC (US); James Jefferson Smith, Morrisville, NC (US); Victor Bartsevich, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 18/586,064

(22) Filed: Feb. 23, 2024

(65) Prior Publication Data

US 2025/0027065 A1 Jan. 23, 2025

Related U.S. Application Data

(62) Division of application No. 16/760,902, filed as application No. PCT/US2018/058692 on Nov. 1, 2018, now abandoned.

(60) Provisional application No. 62/580,031, filed on Nov. 1, 2017.

(51) Int. Cl.
| | |
|---|---|
| *C12N 9/22* | (2006.01) |
| *A61K 9/127* | (2025.01) |
| *A61K 38/02* | (2006.01) |
| *A61K 48/00* | (2006.01) |
| *A61P 7/00* | (2006.01) |
| *C07K 14/755* | (2006.01) |
| *C12N 5/071* | (2010.01) |
| *C12N 15/113* | (2010.01) |
| *C12N 15/86* | (2006.01) |

(52) U.S. Cl.
CPC ............... *C12N 9/22* (2013.01); *A61K 9/127* (2013.01); *A61K 48/005* (2013.01); *A61K 48/0066* (2013.01); *A61P 7/00* (2018.01); *C07K 14/755* (2013.01); *C12N 5/067* (2013.01); *C12N 5/0672* (2013.01); *C12N 15/113* (2013.01); *C12N 15/1136* (2013.01); *C12N 15/86* (2013.01); *A61K 38/02* (2013.01); *C12N 2310/20* (2017.05); *C12N 2320/34* (2013.01); *C12N 2750/14143* (2013.01); *C12N 2800/80* (2013.01)

(58) Field of Classification Search
CPC ........................................................ C12N 9/22
See application file for complete search history.

(56) References Cited

U.S. PATENT DOCUMENTS

| | | | |
|---|---|---|---|
| 4,873,192 A | 10/1989 | Kunkel | |
| 6,015,832 A | 1/2000 | Baker, Jr. et al. | |
| 6,506,803 B1 | 1/2003 | Baker, Jr. et al. | |
| 6,559,189 B2 | 5/2003 | Baker, Jr. et al. | |
| 6,635,676 B2 | 10/2003 | Baker, Jr. et al. | |
| 8,021,867 B2 | 9/2011 | Smith et al. | |
| 8,445,251 B2 | 5/2013 | Smith et al. | |
| 2002/0045667 A1 | 4/2002 | Baker, Jr. et al. | |
| 2004/0043041 A1 | 3/2004 | Baker, Jr. et al. | |
| 2015/0166618 A1* | 6/2015 | Miller ...................... | A61P 3/00 |
| | | | 435/456 |
| 2019/0142973 A1 | 5/2019 | Jantz et al. | |

FOREIGN PATENT DOCUMENTS

| | | | |
|---|---|---|---|
| EP | 2 500 434 A1 | 9/2012 | |
| EP | 3243529 A2 | 11/2017 | |
| WO | WO 02/12514 A2 | 2/2002 | |
| WO | WO 2004/067753 A2 | 8/2004 | |
| WO | WO 2007/047859 A2 | 4/2007 | |
| WO | WO 2009/059195 A2 | 5/2009 | |
| WO | WO 2009/095742 A1 | 8/2009 | |
| WO | WO 2010/009147 A1 | 1/2010 | |
| WO | WO 2012/167192 A2 | 12/2012 | |
| WO | WO 2014/089541 A2 | 6/2014 | |
| WO | WO-2016111546 A2 * | 7/2016 | ................ A61P 7/04 |
| WO | WO-2017062439 A1 * | 4/2017 | ............. A61K 47/67 |

OTHER PUBLICATIONS

English Translation of WO2016111546A2 (Year: 2016).*
International Search Report and Written Opinion for Application No. PCT/US2017/030872 mailed Jun. 28, 2017.
International Preliminary Report on Patentability for Application No. PCT/US2017/030872 mailed Nov. 15, 2018.
International Search Report and Written Opinion for Application No. PCT/US2018/058692 mailed Jan. 30, 2019.
International Preliminary Report on Patentability for Application No. PCT/US2018/058692 mailed May 14, 2020.
Airenne et al., "Baculovirus: an insect-derived vector for diverse gene transfer applications," Mol. Ther. 21(4), 739-749 (2013).

(Continued)

*Primary Examiner* — Christopher M Babic
*Assistant Examiner* — Hanan Isam Abuzeineh
(74) *Attorney, Agent, or Firm* — Womble Bond Dickinson (US) LLP

(57) ABSTRACT

The present invention encompasses engineered nucleases which recognize and cleave a recognition sequence within the int22h-1 sequence of a Factor VIII gene. The present invention also encompasses methods of using such engineered nucleases to make genetically-modified cells, and the use of such cells in a pharmaceutical composition and in methods for treating hemophilia A. Further, the invention encompasses pharmaceutical compositions comprising engineered nuclease proteins, nucleic acids encoding engineered nucleases, or genetically-modified cells of the invention, and the use of such compositions for treating of hemophilia A.

18 Claims, 15 Drawing Sheets

Specification includes a Sequence Listing.

(56)             References Cited

OTHER PUBLICATIONS

Altschul et al., "Basic local alignment search tool," J. Mol. Biol. 215, pp. 403-410 (1990).

Altschul et al., "Gapped BLAST and PSI-BLAST: a new generation of protein database search programs," Nucleic Acids Res. 25, pp. 3389-3402 (1997).

Arnould et al., "Engineering of large numbers of highly specific homing endonucleases that induce recombination on novel DNA targets," J. Mol. Biol. 355, pp. 443-458 (2006).

Bagnali, et al., "Gene conversion and evolution of Xq28 duplicons involved in recurring inversions causing severe hemophilia A," Genome Res., 2005, vol. 15(2), pp. 214-223.

Bagnall et al., Int22h-related inversions causing hemophilia A: a novel insight into their origin and a new more discriminant PCR test for their detection. J Thromb Haemost. Mar. 2006;4(3):591-8.

Belfort et al., Homing endonucleases: from genetic anomalies to programmable genomic clippers. Methods Mol Biol. 2014;1123:1-26. doi: 10.1007/978-1-62703-968-0_1. Author manuscript.

Benoist et al., "In vivo sequence requirements of the SV40 early promotor region," Nature 290(5804), pp. 304-310 (1981).

Beurdeley et al., "Compact designer TALENs for efficient genome engineering," Nat. Commun. 4, p. 1762 (2013).

Bolton-Maggs et al., Haemophilias A and B. Lancet. May 24, 2003;361(9371):1801-9.

Bowen, Haemophilia A and haemophilia B: molecular insights. Mol Pathol. Apr. 2002;55(2):127-44. Erratum in Mol Pathol Jun. 2002;55(3):208.

Cahill et al., "Mechanisms of eukaryotic DNA double strand break repair," Front. Biosci. 11, pp. 1958-1976 (2006).

Chames et al., "In vivo selection of engineered homing endonucleases using double-strand break induced homologous recombination," Nucleic Acids Res. 33, p. e178 (2005).

Chang et al., "Inducible retroviral vectors regulated by lac repressor in mammalian cells," Gene 183, pp. 137-142 (1996).

Chen et al., A novel adenoviral vector carrying an all-in-one Tet-On system with an autoregulatory loop for tight, inducible transgene expression. BMC Biotechnol. Feb. 13, 2015;15:4. doi: 10.1186/s12896-015-0121-4.

Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).

Cheng et al., "Dendrimers as drug carriers: applications in different routes of drug administration," J. Pharm. Sci. 97(1): 123-143 (2008).

Chevalier et al., Homing endonucleases: structural and functional insight into the catalysts of intron/intein mobility. Nucleic Acids Res. Sep. 15, 2001;29(18):3757-74.

Cots et al., "Helper dependent adenovirus vectors: progress and future prospects," Curr. Gene Ther. 13(5) pp. 370-381 (2013).

Deshayes et al., "Cell-penetrating peptides: tools for intracellular delivery of therapeutics," Cell Mol. Life Sci. 62, pp. 1839-1849 (2005).

Deshayes et al., "Primary amphipathic cell-penetrating peptides: structural requirements and interactions with model membranes," Biochemistry 43, pp. 7698-7706 (2004).

Dinda et al., "Nanobiotechnology-based drug delivery in brain targeting," Curr. Pharm. Biotechnol. 14, pp. 1264-1274 (2013).

Dingermann et al., "Establishment of a system for conditional gene expression using an inducible tRNA suppressor gene," Mol. Cell Biol. 12(9), pp. 4038-4045 (1992).

Durai et al., "Zinc finger nucleases: custom-designed molecular scissors for genome engineering of plant and mammalian cells," Nucleic Acids Res. 33, pp. 5978-5990 (2005).

English Translation of WO 2016111546, 2016.

Gao et al., "Efficient gene delivery into mammalian cells mediated by a recombinant baculovirus containing a whispovirus iel promoter, a novel shuttle promoter between insect cells and mammalian cells," J. Biotechnol. 131(2), pp. 138-143 (2007).

GenBank Submission; NIH/NCBI, Accession No. AY619999.1. Homo sapiens isolate Int22h-1 F8a gene, complete cds. Feb. 4, 2005. 3 pages.

Gish et al., "Identification of protein coding regions by database similarity search," Nature Genet. 3, pp. 266-272 (1993).

Grizot et al., "Efficient targeting of a SCID gene by an engineered single-chain homing endonuclease," Nucleic Acids Res. 37, pp. 5405-5419 (2009).

Haase, et al., "Generation of a tumor- and tissue-specific episomal non-viral vector system," BMC Biotechnol. 13, pp. 49-54 (2013).

Hudecz et al., "Medium-sized peptides as built in carriers for biologically active compounds," Med. Res. Rev. 25, pp. 679-736 (2005).

Jacox et al., "Tissue-specific and ubiquitous expression patterns from alternative promoters of human genes," PLoS One 5(8), p. e12274 (2010).

Jearawiriyapaisam et al., "Sustained dystrophin expression induced by peptide-conjugated morpholino oligomers in the muscles of mdx mice," Mol. Ther. 16, pp. 1624-1629 (2008).

Jiang et al., "Cationic core-shell liponanoparticles for ocular gene delivery," Biomaterials. 33(30), pp. 7621-7630 (2012).

Kang et al., "Harnessing the capacity of cell-penetrating peptides for drug delivery to the central nervous system," Curr. Pharm. Biotechnol. 15(3), pp. 220-230 (2014).

Kang et al., Thermoresponsive hydrogels as a new ocular drug delivery platform to the posterior segment of the eye. Trans Am Ophthalmol Soc. 2008; 106:206-13; discussion 213-4.

Kramer et al., "In vitro and in vivo comparative study of chimeric liver-specific promoters," Mol. Ther. 7, pp. 375-385 (2003).

Kunkel et al., Rapid and efficient site-specific mutagenesis without phenotypic selection. Methods Enzymol. 1987; 154:367-82.

Kunkel, "Rapid and efficient site-specific mutagenesis without phenotypic selection," Proc Natl Acad Sci U S A. Jan. 1985;82(2):488-92.

Lentz, et al., "Viral vectors for gene delivery to the central nervous system," Neurobiol. Dis. 48, pp. 179-188 (2012).

Li et al., "Generation of single-chain LAGLIDADG homing endonucleases from native homodimeric precursor proteins," Nucleic Acids . Res. 37, pp. 1650-1662 (2009).

Liu et al., "Therapeutic levels of factor IX expression using a muscle-specific promoter and adeno-associated virus serotype 1 vector," Hum. Gene Ther. 15, pp. 783-792 (2004).

Lozier et a., The Chapel Hill hemophilia A dog colony exhibits a factor VIII gene inversion. Proc Natl Acad Sci U S A. Oct. 1, 2002;99(20):12991-6. Epub Sep. 19, 2002.

Madden et al., "Applications of network BLAST server," Meth. Enzymol. 266, pp. 131-141 (1996).

Mak et al., "TAL effectors: function, structure, engineering and applications," Curr. Opin. Struct. Biol. 23, pp. 93-99 (2013).

Mali et al., "Cas9 as a versatile tool for engineering biology," Nat. Methods 10, pp. 957-963 (2013).

Martin et al., "Gene delivery to the eye using adeno-associated viral vectors," Methods 28, pp. 267-275 (2002).

Mastorakos et al., "Hydroxyl PAMAM dendrimer-based gene vectors for transgene delivery to human retinal pigment epithelial cells," Nanoscale 7(9), pp. 3845-3856 (2015).

McCall et al., "Pathogen-inspired drug delivery to the central nervous system," Tissue Barriers. 2(4), e944449; 12 pages (2014).

McCarty et al., "Self-complementary recombinant adeno-associated virus (scAAV) vectors promote efficient transduction independently of DNA synthesis," Gene Ther. 8, pp. 1248-1254 (2001).

Mishra et al., Recent applications of liposomes in ophthalmic drug delivery. J Drug Deliv. 2011;2011:863734. doi: 10.1155/2011/863734. Epub Mar. 1, 2011.

Park et al., Functional Correction of Large Factor VIII Gene Chromosomal Inversions in Hemophilia A Patient-Derived iPSCs Using CRISPR-Cas9. Cell Stem Cell. Aug. 6, 2015;17(2):213-20. doi: 10.1016/j.stem.2015.07.001. Epub Jul. 23, 2015.

Park et al., Targeted inversion and reversion of the blood coagulation factor 8 gene in human iPS cells using TALENs. Proc Natl Acad Sci U S A. Jun. 24, 2014;111(25):9253-8. doi: 10.1073/pnas.1323941111. Epub Jun. 9, 2014.

(56) References Cited

OTHER PUBLICATIONS

Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.

Ran et al., "Genome engineering using the CRISPR-Cas9 system," Nat. Protoc. 8, pp. 2281-2308 (2013).

Reyon et al., "FLASH assembly of TALENs for high-throughput genome editing," Nat Biotechnol. May 2012;30(5):460-5. doi: 10.1038/nbt.2170. Author manuscript.

Sands, AAV-mediated liver-directed gene therapy. Methods Mol Biol. 2011;807:141-57. doi: 10.1007/978-1-61779-370-7 6. Author manuscript.

Sauna et al., The intron-22-inverted F8 locus permits factor VIII synthesis: explanation for low inhibitor risk and a role for pharmacogenomics. Blood. Jan. 8, 2015;125(2):223-8. doi: 10.1182/blood-2013-12-530113. Epub Nov. 18, 2014.

Seligman et al., "Mutations altering the cleavage specificity of a homing endonuclease," Nucleic Acids Res. 30, pp. 3870-3879 (2002).

Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.

Sharma et al., "Next generation delivery system for proteins and genes of therapeutic purpose: why and how?" Biomed Res Int. 2014;2014:327950. doi: 10.1155/2014/327950. Epub Jul. 15, 2014.

Simeoni et al., "Insight into the mechanism of the peptide-based gene delivery system MPG: implications for delivery of siRNA into mammalian cells," Nucleic Acids Res. 31, pp. 2717-2724 (2003).

Sowa et al., "In vitro and in vivo testing of a novel regulatory system for gene therapy for intervertebral disc degeneration," Spine, 36(10), pp. E623-E628 (2011).

Stoddard, Homing endonuclease structure and function. Q Rev Biophys. Feb. 2005;38(1):49-95. Epub Dec. 9, 2005.

Sussman et al., "Isolation and characterization of new homing endonuclease specificities at individual target site positions," J. Mol. Biol. 342, pp. 31-41 (2004).

Tamboli et al., Polymeric vectors for ocular gene delivery. Ther Deliv. Apr. 2011;2(4):523-36. doi: 10.4155/tde.11.20.

Thomsen et al., "Promoter-regulatory region of the major immediate early gene of human cytomegalovirus," Proc. Natl. Acad. Sci. USA 81(3), pp. 659-663 (1984).

Tong et al., "Eye drop delivery of nano-polymeric micelle formulated genes with cornea-specific promoters," J. Gene Med. 9(11), pp. 956-966 (2007).

Vannucci et al., Viral vectors: a look back and ahead on gene transfer technology. New Microbiol. Jan. 2013;36(1):1-22. Epub Jan. 1, 2013.

Wu et al., In situ genetic correction of F8 intron 22 inversion in hemophilia A patient-specific iPSCs. Sci Rep. Jan. 8, 2016;6:18865. doi: 10.1038/srep18865.

Yuasa et al., "Adeno-associated virus vector-mediated gene transfer into dystrophin-deficient skeletal muscles evokes enhanced immune response against the transgene product," Gene Ther. 9, pp. 1576-1588 (2002).

Zhang et al., "A greedy algorithm for aligning DNA sequences," J. Comput. Biol. 7(1-2), pp. 203-214 (2000).

Zuris et al., "Efficient Delivery of Genome-Editing Proteins In Vitro and In Vivo," Nat. Biotechnol. 33, pp. 73-80 (2015). Author's manuscript. Published online Oct. 30, 2014. doi: 10.1038/nbt.3081.

* cited by examiner

ENGINEERED NUCLEASES THAT TARGET HUMAN AND CANINE FACTOR VIII GENES AS A TREATMENT FOR HEMOPHILIA A

CROSS REFERENCE TO RELATED APPLICATIONS

This application is a divisional of U.S. application Ser. No. 16/760,902, filed Apr. 30, 2020, which is a U.S. National Stage Entry of PCT/US2018/058,692, filed Nov. 1, 2018, which claims priority from U.S. Provisional Application No. 62/580,031, filed Nov. 1, 2017, which applications are hereby incorporated in their entirety by reference in this application.

FIELD OF THE INVENTION

The invention relates to the field of molecular biology and recombinant nucleic acid technology. In particular, the invention relates to engineered nucleases having specificity for a recognition sequence within intron 22 of a Factor VIII gene, and particularly within the int22h-1 sequence. Such engineered nucleases are useful in methods for treating hemophilia A characterized by an inversion of exons 1-22 in the Factor VIII gene.

REFERENCE TO A SEQUENCE LISTING SUBMITTED AS AN XML FILE VIA PATENT CENTER

The instant application contains a Sequence Listing which has been submitted in ST.26 xml format via Patent Center and is hereby incorporated by reference in its entirety. Said ST.26 xml copy, created on Sep. 13, 2024, is named P89339_1144_7_Seq_List.xml, and is 89,686 bytes in size.

BACKGROUND OF THE INVENTION

Hemophilia A is a common genetic bleeding disorder with an incidence of 1 in 5000 males worldwide. This genetic disease can result from various mutations within the coagulation Factor VIII (F8) gene located on the X chromosome, which include large deletions, insertions, inversions, and point mutations. Clinically, hemophilia A can be classified based on relative Factor VIII activity in the patient's plasma as mild (5-30% activity; 50% of patients), moderate (2-5% activity; 10% of patients), or severe (<1% activity; 50% of patients). Currently, there is no cure for hemophilia A. Standard therapy includes the administration of recombinant Factor VIII, but this approach is limited by cost, the requirement for frequent injections, and the formation of Factor VIII-inactivating antibodies in the subject which reduce the effectiveness of therapy. Therefore, a clear need still exists for alternative treatments for hemophilia A. Gene therapy, targeting mutations in the Factor VIII gene, remains an attractive yet elusive approach to treatment.

Factor VIII is an essential component of the clotting cascade. The protein circulates in the body in an inactive form that is attached to von Willebrand factor. In response to injury, Factor VIII is activated (Factor VIIIa) and separates from von Willebrand factor, then interacts with Factor IXa as part of the clotting cascade which leads to the formation of fibrin and stable clotting. A number of studies have suggested that Factor VIII is produced by liver sinusoidal endothelial cells, as well as extra-hepatic, hematopoietic cells throughout the body.

The Factor VIII gene on the X chromosome is large and structurally complex, comprising ~180 kb and 26 exons. The wild-type Factor VIII gene encodes two proteins. The first protein is the full-length Factor VIII protein, which is encoded by the 9030 bases found in exons 1 to 26, and has a circulating form containing 2332 amino acid residues. The second protein, referred to as Factor VIIIb, is encoded by 2598 bases in 5 exons present in the Factor VIII gene. The resulting protein comprises 216 amino acids and has a presently unknown function.

Approximately 45% of severe hemophilia A cases are caused by an intra-chromosomal inversion that involves intron 22 of the Factor VIII gene. This inversion arises when an ~9.5 kb segment of intron 22, referred to as int22h-1, recombines with one of two repeat copies (referred to as int22h-2 and int22h-3, respectively) which are positioned approximately 400 kb and 500 kb telomeric to the Factor VIII gene on the X chromosome. Following recombination, exons 1-22 of the Factor VIII gene become inverted in the genome relative to exons 23-26, resulting in the expression of a truncated, inactive Factor VIII protein that lacks the amino acids encoded by exons 23-26 (Sauna et al. (2015) Blood 125(2): 223-228).

The upstream repeat copy involved in exon 1-22 inversion is oriented in the opposite direction as int22h-1. Early studies suggested that int22h-2 and int22h-3 were both in reverse orientation relative to int22h-1, allowing for recombination to occur with either repeat sequence. This was referred to as Type I inversion and Type II inversion. However, more recent evidence indicates that int22h-2 and int22h-3 are found in an inverse orientation to one another on the X chromosome, and are part of an imperfect palindrome (FIG. 1). Recombination of sequences within this palindrome allows int22h-2 and in22h-3 to swap places in the genome and, consequently, change their orientation relative to int22h-1. As a result, the int22h-1 sequence can, in different circumstances, recombine with the int22h-2 repeat or the int22h-3 repeat, depending on which is in the opposite orientation to int22h-1 (Bagnall et al. (2006) Journal of Thrombosis and Haemostasis 4: 591-598).

Of note, intron 22 of the Factor VIII gene contains a CpG island that acts as a bi-directional promoter for two further genes, referred to as F8A1 (Factor VIII-associated 1) and F8B. The CpG island and the intron-less F8A1 gene (SEQ ID NO: 5) are both contained within the int22h-1 sequence (and consequently, within int22h-2 and in22h-3) and are transcribed in the opposite direction as the Factor VIII gene (Bowen (2002) J. Clin. Pathol: Mol. Pathol. 55: 127-144). Interestingly, the sequence of the F8A1 gene is the only region of the human Factor VIII gene that exhibits significant homology to the Factor VIII gene in the canine genome, and particularly in a clinically-relevant population of canines that are Factor VIII-deficient and exhibit an inversion of exons 1-22 in their Factor VIII gene (Lozier et al. (2002) PNAS 99(20): 12991-12996).

The present invention requires the use of site-specific, rare-cutting nucleases that are engineered to recognize DNA sequences within the int22h-1 sequence in order to generate a double-strand break and promote recombination between int22h-1 and an inversely-oriented repeat sequence (int22h-2 or int22h-3) positioned telomeric to the Factor VIII gene. Nuclease-induced recombination between these regions results in an inversion or reversion of exons 1-22 of the Factor VIII gene. The inventors have discovered that nucleases that are capable of targeting recognition sequences in the int22h-1 region that are highly homologous between the human and canine Factor VIII gene, and lack CpG sites, allows for cleavage of both the human and canine Factor VIII genes and recombination between int22h-1 and an inversely-oriented repeat sequence (int22h-2 or int22h-3). Thus, such nucleases are useful in the clinically-relevant Factor VIII-deficient canine model and for therapeutic treatment of humans.

Methods for producing engineered, site-specific nucleases are known in the art. For example, zinc-finger nucleases (ZFNs) can be engineered to recognize and cut pre-determined sites in a genome. ZFNs are chimeric proteins comprising a zinc finger DNA-binding domain fused to a nuclease domain from an endonuclease or exonuclease (e.g., Type IIs restriction endonuclease, such as the FokI restriction enzyme). The zinc finger domain can be a native sequence or can be redesigned through rational or experimental means to produce a protein which binds to a pre-determined DNA sequence ~18 basepairs in length. By fusing this engineered protein domain to the nuclease domain, it is possible to target DNA breaks with genome-level specificity. ZFNs have been used extensively to target gene addition, removal, and substitution in a wide range of eukaryotic organisms (reviewed in S. Durai et al., *Nucleic Acids Res* 33, 5978 (2005)).

Likewise, TAL-effector nucleases (TALENs) can be generated to cleave specific sites in genomic DNA. Like a ZFN, a TALEN comprises an engineered, site-specific DNA-binding domain fused to an endonuclease or exonuclease (e.g., Type IIs restriction endonuclease, such as the FokI restriction enzyme) (reviewed in Mak, et al. (2013) *Curr Opin Struct Biol.* 23:93-9). In this case, however, the DNA binding domain comprises a tandem array of TAL-effector domains, each of which specifically recognizes a single DNA basepair.

Compact TALENs are an alternative endonuclease architecture that avoids the need for dimerization (Beurdeley, et al. (2013) *Nat Commun.* 4:1762). A Compact TALEN comprises an engineered, site-specific TAL-effector DNA-binding domain fused to the nuclease domain from the I-TevI homing endonuclease or any of the endonucleases listed in Table 2 in U.S. Application No. 20130117869. Compact TALENs do not require dimerization for DNA processing activity, so a Compact TALEN is functional as a monomer.

Engineered endonucleases based on the CRISPR/Cas system are also known in the art (Ran, et al. (2013) *Nat Protoc.* 8:2281-2308; Mali et al. (2013) *Nat Methods.* 10:957-63). A CRISPR endonuclease comprises two components: (1) a caspase effector nuclease; and (2) a short "guide RNA" comprising a ~20 nucleotide targeting sequence that directs the nuclease to a location of interest in the genome. By expressing multiple guide RNAs in the same cell, each having a different targeting sequence, it is possible to target DNA breaks simultaneously to multiple sites in in the genome.

In the preferred embodiment of the invention, the DNA break-inducing agent is an engineered homing endonuclease (also called a "meganuclease"). Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), *Nucleic Acids Res.* 29(18): 3757-3774). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. This, coupled with the extremely low frequency of off-target cutting observed with engineered meganucleases makes them the preferred endonuclease for the present invention.

The use of engineered nucleases for gene therapy in severe hemophilia A has been limited. Park et al. described the use of a TALEN to induce an inversion of exon 1 in the Factor VIII gene in HEK 293T cells and induced pluripotent stem cells (iPSCs) (Park et al. (2014), *PNAS* 111(25): 9253-9258). Inversions of exon 1 are also associated with the occurrence of hemophilia A occur due to homologous recombination between an int1h-1 sequence in intron 1 of the Factor VIII gene and a single homologous region (int1h-2) positioned telomeric to the Factor VIII gene. The TALEN selected for this study cut within the intron 1 homology region in order to induce an inversion of this shorter sequence with an efficiency of 1.9% and 1.4% in the HEK 293T cells and iPSCs, respectively. The authors further demonstrated reversion of exon 1 in the iPSCs at a similar efficiency of 1.3%.

In a subsequent study, Park et al. reported the use of a CRISPR/Cas system to induce a reversion of exons 1-22 of the Factor VIII gene in iPSCs obtained from patients suffering from severe hemophilia A (Park et al. (2015) *Cell Stem Cell* 17: 213-220). The authors noted that inversions of exons 1-22 are eight times more prevalent than inversions of exon 1, but emphasized that the exon 1-22 inversion is technically more challenging to revert due in part to the substantially larger size of the inversion (600 kbp compared to 140 kbp) and the presence of three homologs of the int22h-1 sequence on the X chromosome, compared to only two homologs of the int1h-1 sequence. Indeed, Park et al. specifically targets recognition sequences outside of the int22h-1, int22h-2, and int22h-3 homology regions in order to rule out the possibility that unwanted deletions or inversions involving any two of the three int22 homologs, rather than the desired reversion of the inverted 600-kbp segment, would be induced by cutting within an int22h homology region. Using this approach, the authors observed a reversion frequency of approximately 3.7% in iPS cells.

The present invention improves on the art in several aspects. Despite suggestions in the art to avoid targeting recognition sequences within the int22h homology regions, surprisingly targeting recognition sequences within int22h-1 can, in fact, produce an inversion or reversion of exons 1-22 in the Factor VIII with high efficiency. The recognition sequences targeted within the int22h-1 sequence by the inventors lack CpG sites and have a high degree of homology between the human and canine genomes, such that they can both be targeted by the same nuclease. The absence of CpG sites within the recognition sequences targeted by nucleases avoids potential methylation of these sites, which can hinder cleavage. Thus, the methods of the invention are useful not only in human subjects suffering from hemophilia A, but also in the clinically-relevant canine hemophilia A model which also has an inversion of exons 1-22. Accordingly, the present invention fulfills a need in the art for further gene therapy approaches to severe hemophilia A.

SUMMARY OF THE INVENTION

The present invention provides engineered nucleases useful for the treatment of hemophilia A, which is characterized by an inversion of exons 1-22 of the Factor VIII gene. The engineered nucleases of the invention recognize and a cleave a recognition sequence within an int22h-1 sequence of the Factor VIII gene, thereby promoting recombination between the int22h-1 sequence and an identical, or highly homologous, inverted repeat sequence positioned telomeric to the Factor VIII gene on the X chromosome. Such recombination results in a reversion of exons 1-22 to generate a Factor VIII gene with a wild-type orientation that encodes a biologically-active Factor VIII protein. The recognition sequence recognized by the presently disclosed nucleases does not comprise a CpG site and is at least 80%, at least 85%, at least 90%, at least 95%, or more, identical between the human genome and the canine genome. The present invention also provides pharmaceutical compositions and methods for treatment of hemophilia A which utilize an engineered nuclease having specificity for a recognition sequence positioned within the int22h-1 sequence of the Factor VIII gene that does not comprise a CpG site and is at least 80%, at least 85%, at least 90%, at least 95%, or more, identical between the human genome and the canine genome. The present invention further provides genetically-modified cells which have been modified to correct an inversion of exons 1-22 in the Factor VIII gene, as well as pharmaceutical compositions comprising such genetically-modified cells and methods of using the same for the treatment of hemophilia A.

Thus, in one aspect, the invention provides an engineered meganuclease that recognizes and cleaves a recognition sequence within an int22h-1 sequence of a Factor VIII gene that does not comprise a CpG site and is at least 80%, at least 85%, at least 90%, at least 95%, or more, identical between the human genome and the canine genome. The engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In one embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the recognition sequence can be within an F8A1 coding sequence of the Factor VIII gene. In such an embodiment, the F8A1 coding sequence can have at least 80%, at least 85%, at least 90%, at least 95%, or more, sequence identity to SEQ ID NO: 5 or SEQ ID NO: 6. In another such embodiment, the F8A1 coding sequence can comprise SEQ ID NO: 5 or SEQ ID NO: 6.

In another embodiment, the recognition sequence can comprise SEQ ID NO: 7. In particular embodiments, the recognition sequence can comprise SEQ ID NO: 9 or SEQ ID NO: 11.

In some such embodiments, the HVR1 region can comprise an amino acid sequence having at least 80%, at least 85%, at least 90%, at least 95%, or more, sequence identity to an amino acid sequence corresponding to residues 24-79 of any one of SEQ ID NOs: 13-21.

In certain embodiments, the HVR1 region can comprise residues corresponding to residues 24, 26, 28, 32, 33, 38, 40, 42, 44, 46, 68, 70, 75, and 77 of any one of SEQ ID NOs: 13-21.

In particular embodiments, the HVR1 region can comprise residues 24-79 of any one of SEQ ID NOs: 13-21.

In some such embodiments, the HVR2 region can comprise an amino acid sequence having at least 80%, at least 85%, at least 90%, at least 95%, or more, sequence identity to an amino acid sequence corresponding to residues 215-270 of any one of SEQ ID NOs: 13-21.

In certain embodiments, the HVR2 region can comprise residues corresponding to residues 215, 217, 219, 221, 223, 224, 229, 231, 233, 235, 237, 259, 261, 266, and 268 of any one of SEQ ID NOs: 13-21.

In certain embodiments, the HVR2 region can further comprise a residue corresponding to residue 245 of SEQ ID NO: 16.

In certain embodiments, the HVR2 region can further comprise a residue corresponding to residue 262 of SEQ ID NO: 19.

In certain embodiments, the HVR2 region can further comprise one or more residues corresponding to residues 262, 263, 264, and 265 of SEQ ID NO: 19 or SEQ ID NO: 21.

In particular embodiments, the HVR2 region can comprise residues 215-270 of any one of SEQ ID NOs: 13-21.

In one such embodiment, the first subunit can comprise an amino acid sequence having at least 80%, at least 85%, at least 90%, at least 95%, or more, sequence identity to residues 7-153 of any one of SEQ ID NOs: 13-21, and the second subunit can comprise an amino acid sequence having at least 80%, at least 85%, at least 90%, at least 95, or more, sequence identity to residues 198-344 of any one of SEQ ID NOs: 13-21.

In another such embodiment, the first subunit can further comprise a residue corresponding to residue 80 of any one of SEQ ID NOs: 13-21.

In another such embodiment, the second subunit can further comprise a residue corresponding to residue 210 of any one of SEQ ID NOs: 13-21.

In another such embodiment, the second subunit can further comprise a residue corresponding to residue 271 of any one of SEQ ID NOs: 13-21.

In another embodiment, the first subunit can comprise residues 7-153 of any one of SEQ ID NOs: 13-21.

In another such embodiment, the second subunit can comprise residues 198-344 of any one of SEQ ID NOs: 13-21.

In another such embodiment, the engineered meganuclease can be a single-chain meganuclease comprising a linker, wherein the linker covalently joins the first subunit and the second subunit.

In another such embodiment, the engineered meganuclease can comprise the amino acid sequence of any one of SEQ ID NOs: 13-21.

In another aspect, the invention provides a polynucleotide comprising a nucleic acid sequence encoding any engineered meganuclease of the invention. In a particular embodiment, the polynucleotide can be an mRNA. In some embodiments, the mRNA can be a polycistronic mRNA encoding an engineered meganuclease of the invention and at least one additional polypeptide.

In another aspect, the invention provides a recombinant DNA construct comprising a nucleic acid sequence which encodes any engineered meganuclease of the invention.

In one embodiment, the recombinant DNA construct encodes a viral vector. In such an embodiment, the viral vector can be a retrovirus, a lentivirus, an adenovirus, or an adeno-associated virus (AAV) vector. In a particular embodiment, the viral vector can be a recombinant AAV vector.

In another aspect, the invention provides a viral vector comprising a nucleic acid sequence which encodes any engineered meganuclease of the invention.

In one embodiment, the viral vector can be a retrovirus, a lentivirus, an adenovirus, or an adeno-associated virus (AAV) vector. In a particular embodiment, the viral vector can be a recombinant AAV vector.

In another aspect, the invention provides a pharmaceutical composition for treatment of a subject having hemophilia A. In such an aspect, hemophilia A is characterized by an inversion of exons 1-22 in a Factor VIII gene. The pharmaceutical composition comprises a pharmaceutically acceptable carrier and an effective amount of: (a) a nucleic acid encoding an engineered nuclease, wherein the engineered nuclease is expressed in a target cell in vivo; or (b) an engineered nuclease protein; wherein the engineered nuclease has specificity for a first recognition sequence positioned within an int22h-1 sequence of the Factor VIII gene in the target cell, wherein the first recognition sequence does not comprise a CpG site and is at least 80%, at least 85%, at least 90%, at least 95%, or more identical between the human genome and the canine genome.

In one embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the first recognition sequence can be within an F8A1 coding sequence. In such an embodiment, the F8A1 coding sequence can have at least 80%, at least 85%, at least 90%, at least 95%, or more sequence identity to SEQ ID NO: 5 or SEQ ID NO: 6. In another such embodiment, the F8A1 coding sequence can comprise SEQ ID NO: 5 or SEQ ID NO: 6.

In another embodiment, the engineered nuclease can have specificity for a second recognition sequence that is identical to, or has a high degree of homology with, the first recognition sequence, wherein the second recognition sequence is positioned in a repeat sequence telomeric to the Factor VIII gene in the X chromosome. In such an embodiment, the repeat sequence is identical to, or has a high degree of homology with, the int22h-1 sequence except that the repeat sequence is in reverse orientation relative to the int22h-1 sequence.

In another embodiment, the nucleic acid encoding the engineered nuclease can be an mRNA. In a particular embodiment, the mRNA can be a polycistronic mRNA which encodes an engineered nuclease of the invention and at least one additional polypeptide. In some embodiments, the mRNA or polycistronic mRNA can be encapsulated in a lipid nanoparticle.

In another embodiment, the pharmaceutical composition comprises a recombinant DNA construct comprising the nucleic acid which encodes the engineered nuclease.

In another embodiment, the pharmaceutical composition comprises a viral vector comprising the nucleic acid. In one such embodiment, the viral vector can be a retrovirus, a lentivirus, an adenovirus, or an AAV. In a particular embodiment, the viral vector can be a recombinant AAV vector.

In another embodiment, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment, wherein the engineered nuclease is an engineered meganuclease, the first recognition sequence can comprise SEQ ID NO: 7. In particular embodiments, the first recognition sequence can comprise SEQ ID NO: 9 or SEQ ID NO: 11. In some such embodiments, the pharmaceutical composition can comprise an engineered meganuclease of the invention (or a nucleic acid encoding the same) which recognizes and cleaves SEQ ID NO: 7, 9, or 11. In a particular embodiment, the engineered meganuclease can comprise the amino acid sequence of any one of SEQ ID NOs: 13-21.

In another aspect, the invention provides a method for treating a subject having hemophilia A. In such an aspect, hemophilia A is characterized by an inversion of exons 1-22 of a Factor VIII gene. The method comprises delivering to a target cell in the subject an effective amount of: (a) a nucleic acid encoding an engineered nuclease, wherein the engineered nuclease is expressed in the target cell in vivo; or (b) an engineered nuclease protein; wherein the engineered nuclease is any engineered nuclease of the invention which has specificity for a first recognition sequence positioned within an int22h-1 sequence of the Factor VIII gene in the target cell, wherein the first recognition sequence does not comprise a CpG site and is at least 80%, at least 85%, at least 90%, at least 95%, or more identical between the human genome and the canine genome.

In one embodiment of the method, the method comprises administering to the subject a pharmaceutical composition of the invention described above, which comprises an effective amount of: (a) a nucleic acid encoding an engineered nuclease of the invention, wherein the engineered nuclease is expressed in a target cell in vivo; or (b) an engineered nuclease protein of the invention.

In another embodiment of the method, the engineered nuclease, or the nucleic acid encoding the engineered nuclease, can be delivered to a target cell which can express Factor VIII following a reversion of exons 1-22 to a wild-type orientation, or a progenitor cell which differentiates into a cell which can express Factor VIII following a reversion of exons 1-22 to a wild-type orientation. In one such embodiment, the target cell can be a hepatic cell. In a particular embodiment, the hepatic cell can be a hepatic sinusoidal endothelial cell. In another such embodiment, the hepatic cell can be a progenitor cell, such as a hepatic stem cell, which differentiates into a hepatic sinusoidal endothelial cell. In another such embodiment, the target cell can be a hematopoietic endothelial cell. In another such embodiment, the target cell can be a progenitor cell which differentiates into a hematopoietic endothelial cell. It is to be understood that target cells comprise a Factor VIII gene which has an inversion of exons 1-22.

In another embodiment of the method, the engineered nuclease recognizes and cleaves the first recognition sequence to promote recombination between the int22h-1 sequence and the repeat sequence, resulting in reversion of exons 1-22 to generate a Factor VIII gene having a wild-type orientation.

In another embodiment of the method, the engineered nuclease further recognizes and cleaves the second recognition sequence in the repeat sequence.

In another embodiment of the method, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment of the method, wherein the engineered nuclease is an engineered meganuclease, the first recognition sequence can comprise SEQ ID NO: 7. In one such embodiment, the engineered meganuclease can be any engineered meganuclease of the invention which recognizes and cleaves SEQ ID NO: 7, 9 or 11. In a particular embodiment, the engineered meganuclease can comprise the amino acid sequence of any one of SEQ ID NOs: 13-21.

In another embodiment of the method, the subject can be a mammal. In one such embodiment, the subject can be a human. In another such embodiment, the subject can be a canine. In some embodiments, hemophilia A in the subject is treated. In some embodiments, blood clotting time in the subject is reduced. In some embodiments, circulating levels of Factor VIII are increased.

In another aspect, the invention provides a method for producing a genetically-modified cell comprising a Factor VIII gene having a wild-type orientation. The method comprises: (a) obtaining a cell comprising a Factor VIII gene having an inversion of exons 1-22; and (b) introducing into the cell: (i) a nucleic acid sequence encoding an engineered nuclease, wherein the engineered nuclease is expressed in the cell; or (ii) an engineered nuclease protein; wherein the engineered nuclease has specificity for a first recognition sequence within an int22h-1 sequence of the Factor VIII gene; and wherein the engineered nuclease recognizes and cleaves the first recognition sequence within the int22h-1 sequence to promote recombination between the int22h-1 sequence and a repeat sequence positioned telomeric to the Factor VIII gene; wherein the first recognition sequence does not comprise a CpG site and is at least 80%, at least 85%, at least 90%, at least 95%, or more identical between the human genome and the canine genome, and wherein the repeat sequence is identical to, or has a high degree of homology with, the int22h-1 sequence except that the repeat sequence is in reverse orientation relative to the int22h-1 sequence; and wherein recombination causes reversion of exons 1-22 and generation of the genetically-modified cell comprising a Factor VIII gene having a wild-type orientation.

In one embodiment, the cell can be a eukaryotic cell. In one such embodiment, the eukaryotic cell can be a pluripotent cell. In such an embodiment, the pluripotent cell can be an induced pluripotent stem (iPS) cell. In a particular embodiment, the iPS cell can be a human iPS cell or a canine iPS cell.

In another embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the first recognition sequence can be within an F8A1 coding sequence of the Factor VIII gene. In such an embodiment, the F8A1 coding sequence can have at least 80%, at least 85%, at least 90%, at least 95%, or more, sequence identity to SEQ ID NO: 5 or SEQ ID NO: 6. In a particular embodiment, the F8A1 coding sequence can comprise SEQ ID NO: 5 or SEQ ID NO: 6.

In another embodiment, the engineered nuclease can have specificity for a second recognition sequence that is identical to, or has a high degree of homology with, the first recognition sequence, wherein the second recognition sequence is positioned in a repeat sequence telomeric to the Factor VIII gene in the X chromosome. In such an embodiment, the repeat sequence is identical to, or has a high degree of homology with, the int22h-1 sequence except that the repeat sequence is in reverse orientation relative to the int22h-1 sequence.

In another embodiment, the nucleic acid can be an mRNA.

In another embodiment, the nucleic acid can be introduced into the cell using a recombinant DNA construct.

In another embodiment, the nucleic acid can be introduced into the cell using a viral vector. In one such embodiment, the viral vector can be a retrovirus, a lentivirus, an adenovirus, or an AAV. In a particular embodiment, the viral vector can be a recombinant AAV vector.

In another embodiment, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment, the engineered nuclease can be any engineered meganuclease of the invention which recognizes and cleaves a recognition sequence comprising SEQ ID NO: 7, 9, or 11. In one such embodiment, the engineered meganuclease can comprise the amino acid sequence of any one of SEQ ID NOs: 13-21.

In another aspect, the invention provides a genetically-modified cell, wherein the genetically-modified cell comprises a Factor VIII gene having a wild-type orientation, and is produced according to the methods of the invention described herein, which produce a genetically-modified cell from a cell which comprises a Factor VIII gene having an inversion of exons 1-22.

In another aspect, the invention provides a pharmaceutical composition for treatment of a subject having hemophilia A. In such an aspect, hemophilia A is characterized by an inversion of exons 1-22 in a Factor VIII gene. In different embodiments, the pharmaceutical composition comprises a pharmaceutically acceptable carrier and an effective amount of any genetically-modified cell of the invention, and/or any genetically-modified cell produced according to the methods of the invention, which comprises a Factor VIII gene having a wild-type orientation.

In another aspect, the invention provides a method for treating a subject having hemophilia A. In such an aspect, hemophilia A is characterized by an inversion of exons 1-22 of the Factor VIII gene. The method comprises administering to the subject a pharmaceutical composition of the invention which comprises a pharmaceutically acceptable carrier and an effective amount of any genetically-modified cell of the invention. Such a genetically-modified cell comprises a Factor VIII gene having a wild-type orientation following modification.

In one embodiment of the method, the genetically-modified cell can be delivered to a target tissue. In one such embodiment, the target tissue can be the liver. In another such embodiment, the target tissue can be the circulatory system.

In another embodiment of the method, the genetically-modified cell can be a genetically-modified iPS cell. In one such embodiment, the genetically-modified iPS cell can differentiate into a cell which expresses Factor VIII when it is delivered to the target tissue. In a particular embodiment, the genetically-modified iPS cell can differentiate into a hepatic sinusoidal endothelial cell which expresses Factor VIII. In another particular embodiment, the genetically-modified iPS cell can differentiate into a hematopoietic cell, such as a hematopoietic endothelial cell, which expresses Factor VIII.

In another embodiment of the method, the subject can be a mammal. In one such embodiment, the subject can be a human. In another such embodiment, the subject can be a canine. In some embodiments, hemophilia A in the subject is treated. In some embodiments, blood clotting time in the subject is reduced. In some embodiments, circulating levels of Factor VIII are increased.

In another aspect, the invention provides a method for genetically modifying the Factor VIII gene in the genome of a mammalian cell, wherein the mammalian cell comprises an inversion of exons 1-22 in the Factor VIII gene compared to a wild-type Factor VIII gene. In some embodiments, the method comprises introducing into the mammalian cell: (a) an engineered nuclease having specificity for a first recognition sequence positioned within an int22h-1 sequence of the Factor VIII gene; or (b) a nucleic acid encoding the engineered nuclease, wherein the engineered nuclease is expressed in the mammalian cell; wherein the engineered nuclease recognizes and cleaves the first recognition sequence and causes a reversion of exons 1-22 to a wild-type orientation in the genetically modified mammalian cell; and wherein the first recognition sequence does not comprise a CpG site and is at least 80%, at least 85%, at least 90%, at least 95%, or more identical between the human genome and the canine genome. In such embodiments of the method, the engineered nuclease recognizes and cleaves the first recognition sequence within the int22h-1 sequence to promote recombination between the int22h-1 sequence and a repeat sequence positioned telomeric to the Factor VIII gene; wherein the repeat sequence is identical to, or has a high degree of homology with, the int22h-1 sequence except that the repeat sequence is in reverse orientation relative to the int22h-1 sequence; and wherein recombination causes reversion of exons 1-22 and generation of the genetically-modified cell comprising a Factor VIII gene having a wild-type orientation.

In some embodiments of the method, the int22h-1 sequence comprises a nucleotide sequence having at least 80%, at least 85%, at least 90%, at least 95%, or more, sequence identity to SEQ ID NO: 3 or SEQ ID NO: 4.

In some embodiments of the method, the first recognition sequence is within an F8A1 coding sequence of said Factor VIII gene.

In certain embodiments of the method, the F8A1 coding sequence comprises a nucleotide sequence having at least 80%, at least 85%, at least 90%, at least 95%, or more, sequence identity to SEQ ID NO: 5 or SEQ ID NO: 6.

In some embodiments of the method, the engineered nuclease has specificity for a second recognition sequence that is identical to the first recognition sequence, wherein the second recognition sequence is positioned in a repeat sequence telomeric to the Factor VIII gene in the X chromosome, and wherein the repeat sequence is identical to the int22h-1 sequence except that the repeat sequence is in reverse orientation relative to the int22h-1 sequence.

In some embodiments of the method, the nucleic acid is an mRNA. In certain embodiments of the method, the mRNA is encapsulated in a lipid nanoparticle.

In some embodiments of the method, the nucleic acid is introduced using a recombinant DNA construct comprising the nucleic acid.

In some embodiments of the method, the nucleic acid is introduced using a viral vector comprising the nucleic acid. In particular embodiments of the method, the viral vector is a retroviral vector, a lentiviral vector, an adenoviral vector, or an AAV vector. In certain embodiments of the method, the viral vector is a recombinant AAV vector.

In some embodiments of the method, the engineered nuclease is an engineered meganuclease, a TALEN, a zinc finger nuclease, a compact TALEN, a CRISPR, or a mega-TAL. In certain embodiments of the method, the engineered nuclease is an engineered meganuclease.

In particular embodiments of the method, the first recognition sequence comprises SEQ ID NO: 7. In certain embodiments of the method, the first recognition sequence comprises SEQ ID NO: 9 or SEQ ID NO: 11. In specific embodiments of the method, the engineered meganuclease is any engineered meganuclease described herein which has specificity for a recognition sequence comprising SEQ ID NO: 7, 9, or 11. In other specific embodiments of the method, the engineered meganuclease comprises the amino acid sequence of any one of SEQ ID NOs: 13-21.

In some embodiments of the method, the mammalian cell can express Factor VIII following reversion of exons 1-22 to a wild-type orientation. In certain embodiments of the method, the mammalian cell is a progenitor cell which can differentiate into a cell which can express Factor VIII following reversion of exons 1-22 to a wild-type orientation.

In some embodiments of the method, the mammalian cell is a hepatic cell. In particular embodiments of the method, the mammalian cell is a hepatic sinusoidal endothelial cell. In certain embodiments of the method, the mammalian cell is a progenitor cell capable of differentiating into a hepatic sinusoidal endothelial cell. In certain embodiments of the method, the progenitor cell is a hepatic stem cell.

In some embodiments of the method, the mammalian cell is a hematopoietic endothelial cell. In some embodiments of the method, the mammalian cell is a progenitor cell capable of differentiating into a hematopoietic endothelial cell.

In some embodiments, the method is performed in a subject in vivo. In certain embodiments, the subject has hemophilia A characterized by an inversion of exons 1-22 of the Factor VIII gene. In some such embodiments, the method comprises administering to the subject a pharmaceutical composition described herein. In some such embodiments of the method, the subject is a human. In some such embodiments of the method, the subject is a canine. In some embodiments, hemophilia A in the subject is treated. In some embodiments, blood clotting time in the subject is reduced. In some embodiments, circulating levels of Factor VIII are increased.

In some embodiments, the method is performed in vitro. In some such embodiments of the method, the mammalian cell is a human cell. In some such embodiments of the method, the mammalian cell is a canine cell. In some embodiments of the method, the mammalian cell can be a pluripotent cell, such as an induced pluripotent stem (iPS) cell.

In another aspect, the invention provides a genetically-modified cell produced according to the methods described herein.

In another aspect, the invention provides an engineered nuclease, and particularly an engineered meganuclease, described herein for use as a medicament. The invention further provides the use of an engineered nuclease, and particularly an engineered meganuclease, described herein in the manufacture of a medicament for treating hemophilia A, which is characterized by an inversion of exons 1-22 in the Factor VIII gene.

In another aspect, the invention provides a polynucleotide for use as a medicament, wherein the polynucleotide comprises a nucleic acid sequence encoding an engineered nuclease, and particularly an engineered meganuclease, of the invention. The invention further provides the use of a polynucleotide in the manufacture of a medicament for treating hemophilia A, which is characterized by an inversion of exons 1-22 in the Factor VIII gene, wherein the polynucleotide comprises a nucleic acid sequence encoding an engineered nuclease, and particularly an engineered meganuclease, of the invention.

In another aspect, the invention provides a recombinant AAV vector for use as a medicament, wherein the recombinant AAV vector comprises a polynucleotide which comprises a nucleic acid sequence encoding an engineered nuclease, and particularly an engineered meganuclease, of the invention. The invention further provides the use of a recombinant AAV vector in the manufacture of a medicament for treating hemophilia A, which is characterized by an inversion of exons 1-22 of the Factor VIII gene, wherein the recombinant AAV vector comprises a polynucleotide which comprises a nucleic acid sequence encoding an engineered nuclease, and particularly an engineered meganuclease, of the invention.

In another aspect, the invention provides a genetically-modified cell of the invention for use as a medicament, wherein the genetically-modified cell has been modified to comprise a Factor VIII gene having a wild-type orientation. The invention further provides the use of a genetically-modified cell of the invention in the manufacture of a medicament for treating hemophilia A, which is characterized by an inversion of exons 1-22 of the Factor VIII gene, wherein the genetically-modified cell has been modified to comprise a Factor VIII gene having a wild-type orientation.

BRIEF DESCRIPTION OF THE FIGURES

FIG. 1A shows a configuration in which int22h-3 is in an inverse orientation to int22h-1, allowing for intrachromosomal recombination to occur between these repeat sequences, resulting in the illustrated inversion of exons 1-22. FIG. 1B shows a configuration in which int22h-2 is in an inverse orientation to int22h-1, allowing for intrachromosomal recombination to occur between these repeat sequences, resulting in the illustrated inversion of exons 1-22.

FIG. 5A. shows meganucleases targeting the human F8R 17-18 recognition sequence. FIG. 5B shows meganucleases targeting the canine F8R 17-18 recognition sequence.

FIG. 6A. shows meganucleases targeting the human F8R 17-18 recognition sequence. FIG. 6B shows meganucleases targeting the canine F8R 17-18 recognition sequence.

FIG. 7A. shows meganucleases targeting the human F8R 17-18 recognition sequence. FIG. 7B shows meganucleases targeting the canine F8R 17-18 recognition sequence.

FIG. 8A shows F8R 17-18 meganucleases targeting the human F8R 17-18 recognition sequence. FIG. 8B shows F8R 17-18 meganucleases targeting the canine F8R 17-18 recognition sequence.

FIG. 10A and FIG. 10B. Reversion of Factor VIII gene by F8R nucleases in primary human patient T cells and determination of editing by long-distance PCR. Hemophilia A patient T-cells were transfected with mRNA encoding F8R 17-18x.1, F8R 17-18x.2, F8R 17-18x.79, or F8R 17-18x.88 nucleases. At 3 days post-transfection, genomic DNA was isolated from cells and long-distance PCR was performed to determine Factor VIII genome editing. FIG. 10A shows PCR bands corresponding to the hemophilia A-associated Factor VIII gene inversion, as detected using primers H3D and H1D. FIG. 10B shows PCR bands corresponding to a wild-type Factor VIII gene configuration, as detected using primers H1U and H1D.

FIG. 11A shows PCR bands corresponding to a wild-type Factor VIII gene configuration, as detected using primers H1U and H1D. FIG. 11B shows PCR bands corresponding to the hemophilia A-associated Factor VIII gene inversion, as detected using primers H3D and H1D.

FIG. 12A shows the results corresponding to a wild-type Factor VIII gene configuration, as detected using primers U1 and D1. FIG. 12B shows the results corresponding to the hemophilia A-associated Factor VIII gene inversion, as detected using primers U3 and U1.

FIG. 13A shows the results corresponding to a wild-type Factor VIII gene configuration, as detected using primers U1 and D1. FIG. 13B shows the results corresponding to the hemophilia A-associated Factor VIII gene inversion, as detected using primers U3 and U1.

BRIEF DESCRIPTION OF THE SEQUENCES

Figure 1A:
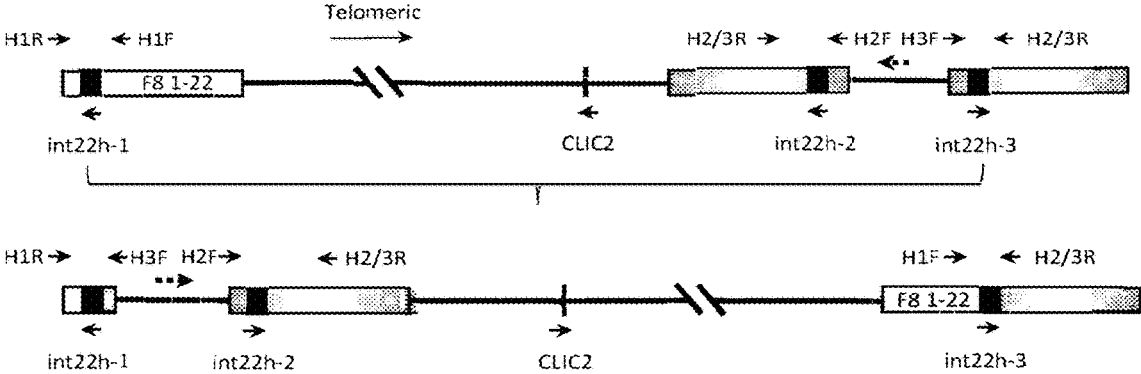
FIG. 1A and FIG. 1B. Inversion of introns 1-22 in the Factor VIII gene. The int22h-2 and int22h-3 repeat sequences are positioned telomeric to the int22h-1 sequence on the X chromosome. Further, int22h-2 and int22h-3 are found in an inverse orientation to one another as part of an imperfect palindrome. Recombination of sequences within this palindrome allows int22h-2 and in22h-3 to swap places in the genome and, consequently, change their orientation relative to int22h-1. As a result, the int22h-1 sequence can, in different circumstances, recombine with the int22h-2 repeat or the int22h-3 repeat, depending on which is in the opposite orientation to int22h-1.
Figure 1B:
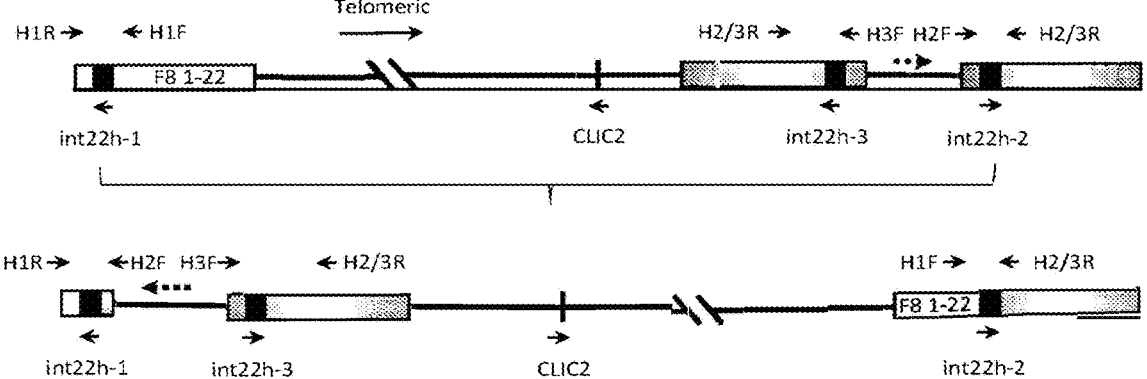

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the nucleic acid sequence of a human int22h-1 sequence.

SEQ ID NO: 4 sets forth the nucleic acid sequence of a canine int22h-1 sequence.

SEQ ID NO: 5 sets forth the nucleic acid sequence of a human F8A1 sequence.

SEQ ID NO: 6 sets forth the nucleic acid sequence of a canine F8A1 sequence.

SEQ ID NO: 7 sets forth the nucleic acid sequence of the F8R 17-18 consensus recognition sequence (sense).

SEQ ID NO: 8 sets forth the nucleic acid sequence of the F8R 17-18 consensus recognition sequence (antisense).

SEQ ID NO: 9 sets forth the nucleic acid sequence of the F8R 17-18 human recognition sequence (sense).

SEQ ID NO: 10 sets forth the nucleic acid sequence of the F8R 17-18 human recognition sequence (antisense).

SEQ ID NO: 11 sets forth the nucleic acid sequence of the F8R 17-18 canine recognition sequence (sense).

SEQ ID NO: 12 sets forth the nucleic acid sequence of the F8R 17-18 canine recognition sequence (antisense).

SEQ ID NO: 13 sets forth the amino acid sequence of the F8R 17-18L1.35 meganuclease.

SEQ ID NO: 14 sets forth the amino acid sequence of the F8R 17-18L2.23 meganuclease.

SEQ ID NO: 15 sets forth the amino acid sequence of the F8R 17-18x.1 meganuclease.

SEQ ID NO: 16 sets forth the amino acid sequence of the F8R 17-18x.2 meganuclease.

SEQ ID NO: 17 sets forth the amino acid sequence of the F8R 17-18x.79 meganuclease.

SEQ ID NO: 18 sets forth the amino acid sequence of the F8R 17-18x.88 meganuclease.

SEQ ID NO: 19 sets forth the amino acid sequence of the F8R 17-18L.626 meganuclease.

SEQ ID NO: 20 sets forth the amino acid sequence of the F8R 17-18L.615 meganuclease.

SEQ ID NO: 21 sets forth the amino acid sequence of the F8R 17-18L.553 meganuclease.

SEQ ID NO: 22 sets forth the amino acid sequence of the F8R 17-18L1.35 meganuclease F8R17-binding monomer.

SEQ ID NO: 23 sets forth the amino acid sequence of the F8R 17-18L2.23 meganuclease F8R17-binding monomer.

SEQ ID NO: 24 sets forth the amino acid sequence of the F8R 17-18x.1 meganuclease F8R17-binding monomer.

SEQ ID NO: 25 sets forth the amino acid sequence of the F8R 17-18x.2 meganuclease F8R17-binding monomer.

SEQ ID NO: 26 sets forth the amino acid sequence of the F8R 17-18x.79 meganuclease F8R17-binding monomer.

SEQ ID NO: 27 sets forth the amino acid sequence of the F8R 17-18x.88 meganuclease F8R17-binding monomer.

SEQ ID NO: 28 sets forth the amino acid sequence of the F8R 17-18L.626 meganuclease F8R17-binding monomer.

SEQ ID NO: 29 sets forth the amino acid sequence of the F8R 17-18L.615 meganuclease F8R17-binding monomer.

SEQ ID NO: 30 sets forth the amino acid sequence of the F8R 17-18L.553 meganuclease F8R17-binding monomer.

SEQ ID NO: 31 sets forth the amino acid sequence of the F8R 17-18L1.35 meganuclease F8R18-binding monomer.

SEQ ID NO: 32 sets forth the amino acid sequence of the F8R 17-18L2.23 meganuclease F8R18-binding monomer.

SEQ ID NO: 33 sets forth the amino acid sequence of the F8R 17-18x.1 meganuclease F8R18-binding monomer.

SEQ ID NO: 34 sets forth the amino acid sequence of the F8R 17-18x.2 meganuclease F8R18-binding monomer.

SEQ ID NO: 35 sets forth the amino acid sequence of the F8R 17-18x.79 meganuclease F8R18-binding monomer.

SEQ ID NO: 36 sets forth the amino acid sequence of the F8R 17-18x.88 meganuclease F8R18-binding monomer.

SEQ ID NO: 37 sets forth the amino acid sequence of the F8R 17-18L.626 meganuclease F8R18-binding monomer.

SEQ ID NO: 38 sets forth the amino acid sequence of the F8R 17-18L.615 meganuclease F8R18-binding monomer.

SEQ ID NO: 39 sets forth the amino acid sequence of the F8R 17-18L.553 meganuclease F8R18-binding monomer.

SEQ ID NO: 40 sets forth the nucleic acid sequence of the H1U primer.

SEQ ID NO: 41 sets forth the nucleic acid sequence of the H1D primer.

SEQ ID NO: 42 sets forth the nucleic acid sequence of the H3D primer.

SEQ ID NO: 43 sets forth the nucleic acid sequence of the U1 primer.

SEQ ID NO: 44 sets forth the nucleic acid sequence of the D1 primer.

SEQ ID NO: 45 sets forth the nucleic acid sequence of the U3 primer.

SEQ ID NO: 46 sets forth the nucleic acid sequence of an off-target recognition sequence.

SEQ ID NO: 47 sets forth the nucleic acid sequence of a K9F8e22F primer sequence.

SEQ ID NO: 48 (tgccaaaga) sets forth the nucleic acid sequence of a K9F8e22-23FAM probe sequence.

SEQ ID NO: 49 sets forth the nucleic acid sequence of a K9F8e22-23FAM probe sequence.

SEQ ID NO: 50 sets forth the nucleic acid sequence of a K9F8e23R primer sequence.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes which cleave a phosphodiester bond within a polynucleotide chain.

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859, incorporated by reference in its entirety). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the present disclosure are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, any of those encompassed by U.S. Pat. Nos. 8,445,251, 9,340,777, 9,434,931, and 10,041,053, each of which is incorporated by reference in its entirety. In some embodiments, a linker may have an amino acid sequence comprising residues 154-195 of any one of SEQ ID NOs: 13-21.

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, S1 nuclease, mung bean nuclease, pancreatic DNAse I, micrococcal nuclease, and yeast HO endonuclease. See, for example, Christian et al. (2010) Genetics 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRI, BglI, and AlwI. Additional Type IIs restriction endonucleases are described in International Publication No. WO 2007/014275. In some embodiments, the nuclease domain of the TALEN is a FokI nuclease domain or an active portion thereof. TAL domain repeats can be derived from the TALE (transcription activator-like effector) family of proteins used in the infection process by plant pathogens of the *Xanthomonas* genus. TAL domain repeats are 33-34 amino acid sequences with divergent $12^{th}$ and $13^{th}$ amino acids. These two positions, referred to as the repeat variable dipeptide (RVD), are highly variable and show a strong correlation with specific nucleotide recognition. Each base pair in the DNA target sequence is contacted by a single TAL repeat, with the specificity resulting from the RVD. In some embodiments, the TALEN comprises 16-22 TAL domain repeats. DNA cleavage by a TALEN requires two DNA recognition regions flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally-occurring TALE protein or can be redesigned through rational or experimental means to produce a protein which binds to a pre-determined DNA sequence (see, for example, Boch et al. (2009) Science 326(5959): 1509-1512 and Moscou and Bogdanove (2009) Science 326(5959):1501, each of which is incorporated by reference in its entirety). See also, U.S. Publication No. 20110145940 and International Publication No. WO 2010/079430 for methods for engineering a TALEN to recognize a specific sequence and examples of RVDs and their corresponding target nucleotides. In some embodiments, each nuclease (e.g., FokI) monomer can be fused to a TAL effector sequence that recognizes a different DNA sequence, and only when the two recognition sites are in close proximity do the inactive monomers come together to create a functional enzyme.

As used herein, the term "compact TALEN" refers to an endonuclease comprising a DNA-binding domain with one or more TAL domain repeats fused in any orientation to any portion of the I-TevI homing endonuclease or any of the endonucleases listed in Table 2 in U.S. Application No. 20130117869 (which is incorporated by reference in its entirety), including but not limited to MmeI, EndA, End1, I-BasI, I-TevII, I-TevIII, I-TwoI, MspI, MvaI, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the term "zinc finger nuclease" or "ZFN" refers to a chimeric protein comprising a zinc finger DNA-binding domain fused to a nuclease domain from an endonuclease or exonuclease, including but not limited to a restriction endonuclease, homing endonuclease, S1 nuclease, mung bean nuclease, pancreatic DNAse I, micrococcal nuclease, and yeast HO endonuclease. Nuclease domains useful for the design of zinc finger nucleases include those from a Type IIs restriction endonuclease, including but not limited to FokI, FoM, and StsI restriction enzyme. Additional Type IIs restriction endonucleases are described in International Publication No. WO 2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 basepairs in length, comprising a pair of nine basepair half-sites separated by 2-10 basepairs. See, for example, U.S. Pat. Nos. 5,789,538, 5,925,523, 6,007,988, 6,013,453, 6,200,759, and International Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in U.S. Publications Nos. 20030232410, 20050208489, 2005064474, 20050026157, 20060188987 and International Publication No. WO 07/014275, each of which is incorporated by reference in its entirety. Cleavage by a zinc finger nuclease can create a blunt end or a 5' overhang of variable length (frequently four basepairs).

As used herein, the term "CRISPR" refers to a system comprising a caspase-based endonuclease comprising a caspase, such as Cas9, Cpf1, or others known in the art, and a guide RNA that directs DNA cleavage of the caspase by hybridizing to a recognition site in the genomic DNA. The caspase component of a CRISPR is an RNA-guided DNA endonuclease. In certain embodiments, the caspase is a class II Cas enzyme. In some of these embodiments, the caspase is a class II, type II enzyme, such as Cas9. In other embodiments, the caspase is a class II, type V enzyme, such as Cpf1. The guide RNA comprises a direct repeat and a guide sequence (often referred to as a spacer in the context of an endogenous CRISPR system), which is complementary to the target recognition site. In certain embodiments, the CRISPR further comprises a tracrRNA (trans-activating CRISPR RNA) that is complementary (fully or partially) to a direct repeat sequence (sometimes referred to as a tracr-mate sequence) present on the guide RNA. In particular embodiments, the caspase can be mutated with respect to a corresponding wild-type enzyme such that the enzyme lacks the ability to cleave one strand of a target polynucleotide, functioning as a nickase, cleaving only a single strand of the target DNA. Non-limiting examples of caspase enzymes that function as a nickase include Cas9 enzymes with a D10A mutation within the RuvC I catalytic domain, or with a H840A, N854A, or N863A mutation.

As used herein, the term "megaTAL" refers to a single-chain endonuclease comprising a transcription activator-like effector (TALE) DNA binding domain with an engineered, sequence-specific homing endonuclease.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

The term "wild-type orientation" as used herein refers to the orientation of exons 1-22 as found in the wild-type Factor VIII gene. It is understood that a Factor VIII gene having a wild-type orientation can be either the wild-type Factor VIII gene normally present in healthy subjects or, alternatively, a variant thereof which comprises an insertion or deletion ("indel") but still encodes a biologically-active Factor VIII protein. For example, in cases where a nuclease cleavage site is within an intron of the int22h-1 region, nuclease cleavage can cause a reversion of the inverted gene back to the wild-type orientation and may produce an indel at the nuclease cleavage site. In such cases, the Factor VIII gene may be modified but, because the resulting indel is within an intron, the gene still encodes a biologically-active Factor VIII protein.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the term "recognition sequence" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a compact TALEN, the recognition sequence comprises a first CNNNGN sequence that is recognized by the I-TevI domain, followed by a nonspecific spacer 4-16 basepairs in length, followed by a second sequence 16-22 bp in length that is recognized by the TAL-effector domain (this sequence typically has a 5' T base). Cleavage by a Compact TALEN produces two basepair 3' overhangs. In the case of a CRISPR, the recognition sequence is the sequence, typically 16-24 basepairs, to which the guide RNA binds to direct cleavage. Full complementarity between the guide sequence and the recognition sequence is not necessarily required to effect cleavage. Cleavage by a CRISPR can produce blunt ends (such as by a class II, type II caspase) or overhanging ends (such as by a class II, type V caspase), depending on the caspase. In those embodiments wherein a Cpf1 caspase is utilized, cleavage by the CRISPR complex comprising the same will result in 5' overhangs and in certain embodiments, 5 nucleotide 5' overhangs. Each caspase enzyme also requires the recognition of a PAM (protospacer adjacent motif) sequence that is near the recognition sequence complementary to the guide RNA. The precise sequence, length requirements for the PAM, and distance from the target sequence differ depending on the caspase enzyme, but PAMs are typically 2-5 base pair sequences adjacent to the target/recognition sequence. PAM sequences for particular caspase enzymes are known in the art (see, for example, U.S. Pat. No. 8,697,359 and U.S. Publication No. 20160208243, each of which is incorporated by reference in its entirety) and PAM sequences for novel or engineered caspase enzymes can be identified using methods known in the art, such as a PAM depletion assay (see, for example, Karvelis et al. (2017) Methods 121-122:3-8, which is incorporated herein in its entirety). In the case of a zinc finger, the DNA binding domains typically recognize an 18-bp recognition sequence comprising a pair of nine base-pair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a nuclease.

As used herein, the term "DNA-binding affinity" or "binding affinity" means the tendency of a nuclease to non-covalently associate with a reference DNA molecule (e.g., a recognition sequence or an arbitrary sequence). Binding affinity is measured by a dissociation constant, $K_d$. As used herein, a nuclease has "altered" binding affinity if the $K_d$ of the nuclease for a reference recognition sequence is increased or decreased by a statistically significant ($p<0.05$) amount relative to a reference nuclease.

As used herein, the term "specificity" means the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art. As used herein, a nuclease has "altered" specificity if it binds to and cleaves a recognition sequence which is not bound to and cleaved by a reference nuclease (e.g., a wild-type) under physiological conditions, or if the rate of cleavage of a recognition sequence is increased or decreased by a biologically significant amount (e.g., at least 2×, or 2×-10×) relative to a reference nuclease.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 13-21. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 32, 33, 38, 40, 42, 44, 46, 68, 70, 75, and 77 of any one of SEQ ID NOs: 13-21. In other embodiments, variable residues within a hypervariable region correspond to one or more of positions 215, 217, 219, 221, 223, 224, 229, 231, 233, 235, 237, 245, 259, 261, 266, and 268 of any one of SEQ ID NOs: 13-21. In certain embodiments, a hypervariable region further comprises a variable residue corresponding to residue 245 of SEQ ID NO: 16. In certain embodiments, a hypervariable region comprises a variable residue corresponding to residue 262 of SEQ ID NO: 19. In certain embodiments, a hypervariable region comprises a variable residue corresponding to one or more of residues 262, 263, 264, and 265 of SEQ ID NO: 19 or SEQ ID NO: 21.

As used herein, the terms "Factor VIII gene," "F8 gene," and the like, refer to a gene located on the X chromosome which encodes the coagulation Factor VIII protein. In humans, the Factor VIII gene, identified by NCBI as Gene ID No. 2157, is located from base pair 154,835,788 to base pair 155,026,934 on the X chromosome. In canines, the Factor VIII gene can be the gene identified by NCBI Reference Sequence: NM_001003212.1. It is understood that the term "Factor VIII gene" can include both a wild-type Factor VIII gene and a Factor VIII gene which comprises naturally-occurring polymorphisms and/or mutations that allow for the production of a functional Factor VIII protein.

As used herein, the terms "int22h-1" and "int22h-1 sequence" refer to a sequence positioned within intron 22 of the Factor VIII gene having a size of approximately 9.5 kb (Bagnall et al. (2006) Journal of Thrombosis and Haemostasis 4:591-598) and can further refer to the human sequence identified by GenBank as Accession No. AY619999.1. The int22h-1 sequence is characterized as comprising a CpG island, a coding sequence for the H2AFB1 histone protein, and a coding sequence for the Factor VIII-Associated 1 protein (F8A1; also referred to as the intron 22 protein). The int22h-1 sequence is further characterized as being identical to, or having high homology with, at least one repeat sequence that is positioned telomeric to the Factor VIII gene on the X chromosome. In humans, two repeat sequences, referred to as int22h-2 and int22h-3, are positioned telomeric to the Factor VIII gene on the X chromosome. In particular embodiments of the invention, the human int22h-1 sequence can comprise SEQ ID NO: 3. In other particular embodiments of the invention, the canine int22h-1 sequence can comprise SEQ ID NO: 4.

As used herein, the terms "F8A1 coding sequence" and "intron 22 protein coding sequence" are used interchangeably and refer to a sequence positioned within the int22h-1 sequence which encodes the F8A1 protein. The F8A1 coding sequence is intronless and is transcribed in the opposite direction as the Factor VIII gene. In one embodiment, the wild-type human F8A1 coding sequence can comprise SEQ ID NO: 5. In another embodiment, the wild-type canine F8A1 coding sequence can comprise SEQ ID NO: 6, which has ~75% homology to the human F8A1 coding sequence. It is understood that reference to an F8A1 coding sequence includes a wild-type F8A1 sequence and an F8A1 sequence comprising naturally-occurring polymorphisms and/or mutations that allow for the production of a functional F8A1 protein.

As used herein, the terms "inversion" and "inversion of exons 1-22" refer to a mutation of a Factor VIII gene wherein an intra-chromosomal homologous recombination event occurs between the int22h-1 sequence of the Factor VIII gene and an identical or closely related, inversely oriented, repeat sequence positioned telomeric to the Factor VIII gene on the X chromosome, which results in an inversion of exons 1-22 with respect to exons 23-26.

As used herein, the term "reversion" refers to an intra-chromosomal homologous recombination event in a cell comprising an inversion of exons 1-22 of the Factor VIII gene, wherein a double-strand break is produced within the int22h-1 sequence to promote recombination with a repeat sequence telomeric to the Factor VIII gene on the X chromosome. Such recombination results in the corrected orientation of exons 1-22 and the production of a functional Factor VIII gene having a wild-type orientation which encodes a biologically-active Factor VIII protein.

As used herein, the term "CpG site" refers to regions of DNA in the genome characterized by a cytosine nucleotide followed by a guanine nucleotide in the linear sequence of bases. Cytosine bases in CpG sites can be methylated.

The terms "recombinant DNA construct," "recombinant construct," "expression cassette," "expression construct," "chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a nuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, the terms "treatment" or "treating a subject" refers to the administration of an effective amount of an engineered nuclease of the invention, or an effective amount of a nucleic acid encoding an engineered nuclease of the invention, to a subject having hemophilia A for the purpose of correcting an inversion of exons 1-22 in the Factor VIII gene in cells which normally express Factor VIII in wild-type subjects. Such treatment results in correction of the Factor VIII gene in a number of cells sufficient to increase circulating levels of Factor VIII in the subject, and either partial or complete relief of one or more symptoms of hemophilia A in the subject including, but not limited to, a reduction in clotting time. The terms "treatment" or "treating a subject" can further refer to the administration of an effective amount of a genetically-modified cell comprising a Factor VIII gene having a wild-type orientation to a subject according the method of the invention, wherein the genetically-modified cell is delivered to a target tissue and either produces biologically-active Factor VIII, or differentiates into a cell which produces biologically-active Factor VIII, in an amount sufficient to increase the circulating levels of biologically-active Factor VIII in the subject, resulting in either partial or complete relief of one or more symptoms of hemophilia A including, but not limited to, a reduction in clotting time. In some aspects, an engineered nuclease of the invention, a nucleic acid encoding the same, or a genetically-modified cell of the invention is administered during treatment in the form of a pharmaceutical composition of the invention.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of the engineered meganuclease or pharmaceutical compositions disclosed herein reduces clotting time in a subject having hemophilia A, and/or increases detectable circulating levels of functional Factor VIII protein in the subject's blood.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Invention

The present invention is based, in part, on the hypothesis that engineered nucleases that cleave recognition sequences within an int22h-1 sequence of the Factor VIII gene in both the human and canine genome can be used to correct an inversion of exons 1-22 in the Factor VIII gene and are thus useful for the treatment of human patients with hemophilia A and the clinically-relevant canine model of hemophilia A. More specifically, nucleases can be engineered to recognize and cleave a recognition sequence within an int22h-1 sequence of the Factor VIII gene that does not comprise a CpG site and has a high degree of homology between the human and canine genome to produce a double-strand break in either the human or canine genome. Intra-chromosomal homologous recombination can then occur between the int22h-1 sequence and a repeat sequence which is telomeric to the Factor VIII gene on the X chromosome, resulting in a reversion of exons 1-22 and the production of a Factor VIII gene having a wild-type orientation in target cells of the subject, which encodes a biologically-active Factor VIII protein.

The invention is also based, in part, on the hypothesis that pluripotent cells (e.g., induced pluripotent stem (iPS) cells) comprising an inversion of exons 1-22 in the Factor VIII gene can be obtained and contacted with an engineered nuclease of the invention (or a nucleic acid encoding the same) in order to correct the Factor VIII gene by the same mechanism described above. Such pluripotent cells can then be administered to a subject having hemophilia A, wherein the cells are delivered to a target tissue (e.g., the liver or the circulatory system) and differentiate into cells which express biologically-active Factor VIII in the subject.

Thus, the present invention encompasses engineered nucleases, and particularly engineered recombinant meganucleases, which recognize and cleave a recognition sequence within the int22h-1 sequence of a Factor VIII gene in both the human and canine genomes. The present invention also encompasses methods of using such engineered nucleases to make genetically-modified cells, and the use of such cells in a pharmaceutical composition and in methods for treating hemophilia A. Further, the invention encompasses pharmaceutical compositions comprising engineered nuclease proteins, nucleic acids encoding engineered nucleases, or genetically-modified cells of the invention, and the use of such compositions for the treatment of hemophilia A.

2.2 Nucleases for Recognizing and Cleaving Recognition Sequences within an int22h-1 Sequence of the Factor VIII Gene It is known in the art that it is possible to use a site-specific nuclease to make a DNA break in the genome of a living cell, and that such a DNA break can result in permanent modification of the genome via homologous recombination of the cleaved target site with an identical or highly homologous DNA sequence within the genome.

Thus, in different embodiments, a variety of different types of nuclease are useful for practicing the invention. In one embodiment, the invention can be practiced using engineered recombinant meganucleases. In another embodiment, the invention can be practiced using a CRISPR nuclease or CRISPR Nickase. Methods for making CRIS-PRs and CRISPR Nickases that recognize pre-determined DNA sites are known in the art, for example Ran, et al. (2013) Nat Protoc. 8:2281-308. In another embodiment, the invention can be practiced using TALENs or Compact TALENs. Methods for making TALE domains that bind to pre-determined DNA sites are known in the art, for example and the canine F8R 17-18 recognition sequence (SEQ ID NO: 11), which are represented by the consensus F8R 17-18 recognition sequence (SEQ ID NO: 7). The F8R 17-18 recognition sequence is positioned within both the int22h-1 sequence and the F8A1 sequence. Such recombinant meganucleases are collectively referred to herein as "F8R 17-18 meganucleases." Exemplary F8R 17-18 meganucleases are provided in SEQ ID NOs: 13-21.

Recombinant meganucleases of the invention comprise a first subunit, comprising a first hypervariable (HVR1) region, and a second subunit, comprising a second hypervariable (HVR2) region. Further, the first subunit binds to a first recognition half-site in the recognition sequence (i.e., the F8R17 half-site), and the second subunit binds to a second recognition half-site in the recognition sequence (e.g., the F8R18 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary F8R 17-18 meganucleases of the invention are provided in Table 1.

TABLE 1

Exemplary recombinant meganucleases engineered to recognize and cleave the consensus F8R 17-18 recognition sequence (SEQ ID NO: 7)

| Meganuclease | AA SEQ ID | F8R17 Subunit Residues | F8R17 Subunit SEQ ID | *F8R17 Subunit % | F8R18 Subunit Residues | F8R18 Subunit SEQ ID | *F8R18 Subunit % |
|---|---|---|---|---|---|---|---|
| F8R 17-18L1.35 | 13 | 7-153 | 22 | 100 | 198-344 | 31 | 100 |
| F8R 17-18L2.23 | 14 | 7-153 | 23 | 97.96 | 198-344 | 32 | 92.52 |
| F8R 17-18x.1 | 15 | 7-153 | 24 | 97.28 | 198-344 | 33 | 98.64 |
| F8R 17-18x.2 | 16 | 7-153 | 25 | 97.28 | 198-344 | 34 | 91.84 |
| F8R 17-18x.79 | 17 | 7-153 | 26 | 96.6 | 198-344 | 35 | 92.52 |
| F8R17-18x.88 | 18 | 7-153 | 27 | 97.28 | 198-344 | 36 | 92.52 |
| F8R17-18L.626 | 19 | 7-153 | 28 | 96.6 | 198-344 | 37 | 96.6 |
| F8R17-18L.615 | 20 | 7-153 | 29 | 96.6 | 198-344 | 38 | 97.28 |
| F8R17-18L.553 | 21 | 7-153 | 30 | 96.6 | 198-344 | 39 | 94.56 |

*"F8R17 Subunit %" and "F8R18 Subunit %" represent the amino acid sequence identity between the F8R17-binding and F8R18-binding subunit regions of each meganuclease and the F8R17-binding and F8R18-binding subunit regions, respectively, of the F8R 17-18L1.35 meganuclease.

Reyon et al. (2012) Nat Biotechnol. 30:460-5. In another embodiment, the invention can be practiced using zinc finger nucleases (ZFNs). In a further embodiment, the invention can be practiced using megaTALs.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, recombinant meganucleases of the invention have been engineered to recognize and cleave both the human F8R 17-18 recognition sequence (SEQ ID NO: 9)

2.3 Methods for Delivering and Expressing Nucleases

The invention provides methods for producing genetically-modified cells using engineered nucleases that recognize and cleave recognition sequences found within an intron 22 sequence of a Factor VIII gene. The invention further provides methods for treating hemophilia A in a subject by administering a pharmaceutical composition comprising a pharmaceutically acceptable carrier and an engineered nuclease of the invention (or a nucleic acid encoding the engineered nuclease). In each case, the invention requires that an engineered nuclease of the invention can be delivered to and/or expressed from DNA/RNA in appropriate cells that comprise an inversion of exons 1-22 in a Factor VIII gene and would typically express Factor VIII in a healthy subject (e.g., hepatic sinusoidal endothelial cells or hematopoietic endothelial cells, or progenitor cells which differentiate into the same).

Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA (e.g., mRNA). For embodiments in which the engineered nuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804):304-10) as well as inducible promoters such as the tetracycline-inducible promoter (Dingermann et al. (1992), Mol Cell Biol. 12(9):4038-45). An engineered nuclease of the invention can also be operably linked to a synthetic promoter. Synthetic promoters can include, without limitation, the JeT promoter (WO 2002/012514).

In some embodiments, mRNA encoding a nuclease is delivered to a cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methyl-guanosine. In some embodiments, the mRNA may be polyadenylated.

In another particular embodiment, a nucleic acid encoding a nuclease of the invention can be introduced into the cell using a single-stranded DNA template. The single-stranded DNA can further comprise a 5' and/or a 3' AAV inverted terminal repeat (ITR) upstream and/or downstream of the sequence encoding the engineered nuclease. In other embodiments, the single-stranded DNA can further comprise a 5' and/or a 3' homology arm upstream and/or downstream of the sequence encoding the engineered nuclease.

In another particular embodiment, genes encoding a nuclease of the invention can be introduced into a cell using a linearized DNA template. In some examples, a plasmid DNA encoding a nuclease can be digested by one or more restriction enzymes such that the circular plasmid DNA is linearized prior to being introduced into a cell.

Purified nuclease proteins can be delivered into cells to cleave genomic DNA by a variety of different mechanisms known in the art, including those further detailed herein below.

The target tissue(s) for delivery of recombinant nucleases of the invention include, without limitation, cells of the liver, preferably hepatic sinusoidal endothelial cells or, alternatively, progenitor cells which differentiate into hepatic sinusoidal endothelial cells. Target tissues can also include, without limitation, cells in the circulatory system, preferably hematopoietic endothelial cells or, alternatively, progenitor cells which differentiate into hematopoietic endothelial cells. As discussed, nucleases of the invention can be delivered as purified protein or as RNA or DNA encoding the nucleases. In one embodiment, nuclease proteins, or mRNA, or DNA vectors encoding nucleases, are supplied to target cells (e.g., cells in the liver or cells in the circulatory system) via injection directly to the target tissue. Alternatively, nuclease protein, mRNA, or DNA can be delivered systemically via the circulatory system.

In some embodiments, nuclease proteins, or DNA/mRNA encoding nucleases, are formulated for systemic administration, or administration to target tissues, in a pharmaceutically acceptable carrier in accordance with known techniques. See, e.g., Remington, The Science And Practice of Pharmacy (21st ed. 2005). In the manufacture of a pharmaceutical formulation according to the invention, proteins/RNA/mRNA are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, nuclease proteins, or DNA/mRNA encoding the nuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, nuclease proteins, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, nuclease protein/DNA/mRNA can be coupled covalently or non-covalently to the natural ligand (or a portion of the natural ligand) for such a cell-surface receptor. (McCall, et al. (2014) Tissue Barriers. 2(4):e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, nuclease proteins, or DNA/mRNA encoding nucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, nuclease proteins, or DNA/mRNA encoding nucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the nuclease proteins, mRNA, or DNA can be attached to or encapsulated with the nanoparticle core. This increases the copy number of the protein/mRNA/DNA that is delivered to each cell and, so, increases the intracellular expression of each nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to tar-
geting molecules to direct the nanoparticle to the appropriate
cell type and/or increase the likelihood of cellular uptake.
Examples of such targeting molecules include antibodies
specific for cell-surface receptors and the natural ligands (or
portions of the natural ligands) for cell surface receptors.

In some embodiments, the nuclease proteins or DNA/
mRNA encoding the nucleases are encapsulated within
liposomes or complexed using cationic lipids (see, e.g.,
Lipofectamine™, Life Technologies Corp., Carlsbad, CA;
Zuris et al. (2015) Nat Biotechnol. 33: 73-80; Mishra et al.
(2011) J Drug Deliv. 2011:863734). The liposome and
lipoplex formulations can protect the payload from degra-
dation, enhance accumulation and retention at the target site,
and facilitate cellular uptake and delivery efficiency through
fusion with and/or disruption of the cellular membranes of
the target cells.

In some embodiments, nuclease proteins, or DNA/mRNA
encoding nucleases, are encapsulated within polymeric scaf-
folds (e.g., PLGA) or complexed using cationic polymers
(e.g., PEI, PLL) (Tamboli et al. (2011) Ther Deliv. 2(4):
523-536). Polymeric carriers can be designed to provide
tunable drug release rates through control of polymer ero-
sion and drug diffusion, and high drug encapsulation effi-
ciencies can offer protection of the therapeutic payload until
intracellular delivery to the desired target cell population.

In some embodiments, nuclease proteins, or DNA/mRNA
encoding recombinant meganucleases, are combined with
amphiphilic molecules that self-assemble into micelles
(Tong et al. (2007) J Gene Med. 9(11): 956-66). Polymeric
micelles may include a micellar shell formed with a hydro-
philic polymer (e.g., polyethyleneglycol) that can prevent
aggregation, mask charge interactions, and reduce nonspe-
cific interactions.

In some embodiments, nuclease proteins, or DNA/mRNA
encoding nucleases, are formulated into an emulsion or a
nanoemulsion (i.e., having an average particle diameter of
<1 nm) for administration and/or delivery to the target cell.
The term "emulsion" refers to, without limitation, any
oil-in-water, water-in-oil, water-in-oil-in-water, or oil-in-
water-in-oil dispersions or droplets, including lipid struc-
tures that can form as a result of hydrophobic forces that
drive apolar residues (e.g., long hydrocarbon chains) away
from water and polar head groups toward water, when a
water immiscible phase is mixed with an aqueous phase.
These other lipid structures include, but are not limited to,
unilamellar, paucilamellar, and multilamellar lipid vesicles,
micelles, and lamellar phases. Emulsions are composed of
an aqueous phase and a lipophilic phase (typically contain-
ing an oil and an organic solvent). Emulsions also frequently
contain one or more surfactants. Nanoemulsion formulations
are well known, e.g., as described in US Patent Application
Nos. 2002/0045667 and 2004/0043041, and U.S. Pat. Nos.
6,015,832, 6,506,803, 6,635,676, and 6,559,189, each of
which is incorporated herein by reference in its entirety.

In some embodiments, nuclease proteins, or DNA/mRNA
encoding nucleases, are covalently attached to, or non-
covalently associated with, multifunctional polymer conju-
gates, DNA dendrimers, and polymeric dendrimers (Mas-
torakos et al. (2015) Nanoscale. 7(9): 3845-56; Cheng et al.
(2008) J Pharm Sci. 97(1): 123-43). The dendrimer genera-
tion can control the payload capacity and size, and can
provide a high drug payload capacity. Moreover, display of
multiple surface groups can be leveraged to improve stabil-
ity, reduce nonspecific interactions, and enhance cell-spe-
cific targeting and drug release.

In some embodiments, genes encoding a nuclease are
delivered using a viral vector. Such vectors are known in the
art and include retroviral vectors, lentiviral vectors, adeno-
viral vectors, and adeno-associated virus (AAV) vectors
(reviewed in Vannucci, et al. (2013 New Microbiol. 36:1-
22). In some embodiments, the viral vectors are injected
directly into target tissues. In alternative embodiments, the
viral vectors are delivered systemically via the circulatory
system. It is known in the art that different AAV vectors tend
to localize to different tissues. In liver target tissues, effec-
tive transduction of hepatocytes has been shown, for
example, with AAV serotypes 2, 8, and 9 (Sands (2011)
Methods Mol. Biol. 807:141-157). AAV vectors can also be
self-complementary such that they do not require second-
strand DNA synthesis in the host cell (McCarty, et al. (2001)
Gene Ther. 8:1248-54).

In one embodiment, a viral vector used for nuclease gene
delivery is a self-limiting viral vector. A self-limiting viral
vector can have limited persistence time in a cell or organ-
ism due to the presence of a recognition sequence for a
recombinant nuclease within the vector. Thus, a self-limiting
viral vector can be engineered to provide coding for a
promoter, a nuclease described herein, and a nuclease rec-
ognition site within the ITRs. The self-limiting viral vector
delivers the nuclease gene to a cell, tissue, or organism, such
that the nuclease is expressed and able to cut the genome of
the cell at an endogenous recognition sequence within the
genome. The delivered nuclease will also find its target site
within the self-limiting viral vector itself, and cut the vector
at this target site. Once cut, the 5' and 3' ends of the viral
genome will be exposed and degraded by exonucleases, thus
killing the virus and ceasing production of the nuclease.

If the nuclease genes are delivered in DNA form (e.g.
plasmid) and/or via a viral vector (e.g. AAV) they must be
operably linked to a promoter. In some embodiments, this
can be a viral promoter such as endogenous promoters from
the viral vector (e.g. the LTR of a lentiviral vector) or the
well-known cytomegalovirus- or SV40 virus-early promot-
ers. In a preferred embodiment, nuclease genes are operably
linked to a promoter that drives gene expression preferen-
tially in the target cells. Examples of liver-specific promot-
ers include, without limitation, human alpha-1 antitrypsin
promoter and apolipoprotein A-II promoter.

It is envisioned that a single treatment will permanently
cause a reversion of exons 1-22 in the Factor VIII gene,
resulting in a gene having a wild-type orientation in a
percentage of patient target cells. If the frequency of rever-
sion is low, however, or if a large percentage of target cells
need to be corrected, it may be necessary to perform
multiple treatments on each patient.

2.4 Pharmaceutical Compositions

In some embodiments, the invention provides a pharma-
ceutical composition comprising a pharmaceutically accept-
able carrier and an effective amount of an engineered
nuclease of the invention, or a pharmaceutically acceptable
carrier and an effective amount of a polynucleotide com-
prising a nucleic acid encoding an engineered nuclease of
the invention. In other embodiments, the invention provides
a pharmaceutical composition comprising a pharmaceuti-
cally acceptable carrier and an effective amount of a geneti-
cally-modified cell of the invention which can be delivered
to a target tissue where the cell can then differentiate into a
cell which expresses biologically-active Factor VIII. Phar-
maceutical compositions of the invention can be useful for treating a subject having hemophilia A, wherein the disease is characterized by an inversion of exons 1-22 in a Factor VIII gene.

Such pharmaceutical compositions can be prepared in accordance with known techniques. See, e.g., Remington, The Science and Practice of Pharmacy (21st ed. 2005). In the manufacture of a pharmaceutical formulation according to the invention, nuclease polypeptides (or DNA/RNA encoding the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

In particular embodiments of the invention, the pharmaceutical composition can comprise one or more mRNAs described herein encapsulated within lipid nanoparticles, which are described elsewhere herein. In other embodiments, lipid nanoparticles can comprise one or more polycistronic mRNAs described herein, wherein each polycistronic mRNA encodes at least one engineered nucleases of the invention and at least one additional polypeptide.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, 7-LenMC3, CP-7-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N, N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA·Cl), 1,2-dilinoleoyl-3-trimethylaminopropane chloride salt (DLin-TAP·Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N, N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, 7-LenMC3, CP-7-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In preferred embodiments, the non-cationic lipid comprises one of the following neutral lipid components: (1) cholesterol or a derivative thereof, (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoylphosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl]cholesterol, TC-Chol 3-β-[N—(N', N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethyl-amronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or omithine and phosphatidyl ethanolarnine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidyletha-nolamine and phosphatidic acid, PEG-ceramide conjugates (e.g., PEG-CerC14 or PEG-CerC20), PEG-modified dialky-lamines and PEG-modified 1,2-diacyloxypropan-3-amines. Particularly preferred are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggrega-tion of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cat-ionic to anionic lipid may selected in order to achieve the desired properties of nucleic acid encapsulation, zeta poten-tial, pKa, or other physicochemical property that is at least in part dependent on the presence of charged lipid compo-nents.

In some embodiments, the lipid nanoparticles have a composition which specifically enhances delivery and uptake in the liver, or specifically within hepatic sinusoidal endothelial cells. The composition may also specifically enhance delivery uptake by endothelial cells in the circula-tory system.

An "effective amount" or "therapeutically effective amount" of a pharmaceutical composition, engineered nuclease, or nucleic acid encoding an engineering nuclease, generally refers to an amount sufficient to effect beneficial or desirable biological and/or clinical results. In the treatment of hemophilia A, characterized by an inversion of exons 1-22 of the Factor VIII gene, an effective amount reduces clotting time and/or increases detectable circulating levels of functional Factor VIII protein in the subject's blood. Clot-ting time in a subject may be reduced by any amount until achieving a clotting time exhibited by a wild-type healthy subject. Clotting time can be measured relative to the same subject prior to treatment, or relative to the clotting time of a subject having hemophilia A characterized by an inversion of exons 1-22 of the Factor VIII gene. Clotting time of a healthy human subject can typically be between 8 to 15 minutes. Such reductions in clotting time can be about 1, 2, 3, 4, 5, 6, 7, 8, 9, 10, 15, 20, 25, 30, 35, 40, 45, 50, 55, or 60 minutes, or more, including a reduction to the clotting time of a healthy wild-type subject. Clotting time can be measured using any methods known in the art including, but not limited to, a whole blood clotting test (WBCT) as described in the Examples herein, an activated partial throm-boplastin time (aPTT) test, a prothrombin time (PT) test, and/or a fibrinogen test. Increases in detectable circulating Factor VIII can be up to about 1 fold, 2 fold, 3 fold, 4, fold, 5 fold, 10 fold, 20 fold, 30 fold, 40 fold, 50 fold, 60 fold, 70 fold, 80 fold, 90 fold, 100 fold, 250 fold, 500 fold, 750 fold, or 1000 fold, or more, higher than the baseline level of circulating Factor VIII in the subject, or up to the level of circulating Factor VIII exhibited by a healthy wild-type subject. Circulating levels of Factor VIII can be measured using any methods known in the art including, but not limited to, an enzyme linked immunosorbent assay (ELSIA). Methods for detecting mRNA encoding full-length Factor VIII in a wild-type orientation include those described in the Examples herein.

2.5 Methods for Producing Recombinant AAV Vectors

In some embodiments, the invention provides recombi-nant AAV vectors for us in the methods of the invention. Recombinant AAV vectors are typically produced in mam-malian cell lines such as HEK-293. Because the viral cap and rep genes are removed from the vector to prevent its self-replication to make room for the therapeutic gene(s) to be delivered (e.g. the nuclease gene), it is necessary to provide these in trans in the packaging cell line. In addition, it is necessary to provide the "helper" (e.g. adenoviral) components necessary to support replication (Cots D, Bosch A, Chillon M (2013) Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the interven-ing DNA sequence to be packaged into the virus. Viral particles comprising a genome (ITRs and intervening gene (s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically pro-duced (manufactured) in cells, precautions must be taken in practicing the current invention to ensure that the site-specific nuclease is not expressed in the packaging cells. Because the viral genomes of the invention comprise a recognition sequence for the nuclease, any nuclease expressed in the packaging cell line will be capable of cleaving the viral genome before it can be packaged into viral particles. This will result in reduced packaging effi-ciency and/or the packaging of fragmented genomes. Sev-eral approaches can be used to prevent nuclease expression in the packaging cells, including:

1. The nuclease can be placed under the control of a tissue-specific promoter that is not active in the packaging cells. For example, if a viral vector is developed for delivery of (an) nuclease gene(s) to muscle tissue, a muscle-specific promoter can be used. Examples of muscle-specific promoters include C5-12 (Liu, et al. (2004) *Hum Gene Ther.* 15:783-92), the muscle-specific creatine kinase (MCK) promoter (Yuasa, et al. (2002) *Gene Ther.* 9:1576-88), or the smooth muscle 22 (SM22) promoter (Haase, et al. (2013) *BMC Biotechnol.* 13:49-54). Examples of CNS (neuron)-specific promoters include the NSE, Synapsin, and MeCP2 promoters (Lentz, et al. (2012) *Neurobiol Dis.* 48:179-88). Examples of liver-specific promoters include albumin promoters (such as Palb), human $\alpha$1-antitrypsin (such as Pa1AT), and hemopexin (such as Phpx) (Kramer, M G et al., (2003) *Mol. Therapy* 7:375-85). Examples of eye-specific promoters include opsin, and corneal epithelium-specific K12 promoters (Martin K R G, Klein R L, and Quigley H A (2002) Methods (28): 267-75) (Tong Y, et al., (2007) *J Gene Med,* 9:956-66). These promoters, or other tissue-specific promoters known in the art, are not highly-active in HEK-293 cells and, thus, will not be expected to yield significant levels of nuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) *PLoS One* v. 5(8):e12274).

2. Alternatively, the vector can be packaged in cells from a different species in which the nuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) *J. Biotechnol.* 131(2):138-43). A nuclease under the control of a mammalian promoter is unlikely to be expressed in these cells (Airenne, K J, et al. (2013) *Mol. Ther.* 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a nuclease. Because these introns are not spliced efficiently from pre-mRNA transcripts in insect cells, insect cells will not express a functional nuclease and will package the full-length genome. In contrast, mammalian cells to which the resulting recombinant AAV particles are delivered will properly splice the pre-mRNA and will express functional nuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) *Mol Ther Nucleic Acids.* 1(11): e57).

3. The nuclease gene can be operably linked to an inducible promoter such that a small-molecule inducer is required for nuclease expression. Examples of inducible promoters include the Tet-On system (Clontech; Chen H., et al., (2015) *BMC Biotechnol.* 15(1):4)) and the RheoSwitch system (Intrexon; Sowa G., et al., (2011) *Spine,* 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the nuclease gene under the control of a promoter that responds to the corresponding transcription factor, the nuclease gene having (a) binding site(s) for the transcription factor; and 2) including the gene encoding the transcription factor in the packaged viral genome The latter step is necessary because the nuclease will not be expressed in the target cells or tissues following recombinant AAV delivery if the transcription activator is not also provided to the same cells. The transcription activator then induces nuclease gene expression only in cells or tissues that are treated with the cognate small-molecule activator. This approach is advantageous because it enables nuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the nuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the nuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the nuclease gene will be repressed only in the packaging cells expressing the repressor and not in target cells or tissues transduced with the resulting recombinant AAV vector.

2.6 Engineered Nuclease Variants

Embodiments of the invention encompass the engineered nucleases described herein, and variants thereof. Further embodiments of the invention encompass polynucleotides comprising a nucleic acid sequence encoding the nucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave recognition sequences found in an int22h-1 sequence in a Factor VIII gene including, for example, the human F8R 17-18 recognition sequence (SEQ ID NO: 9), the canine F8R 17-18 recognition sequence (SEQ ID NO: 11), and the consensus F8R 17-18 recognition sequence (SEQ ID NO: 7). Such variants may result, for example, from human manipulation. Biologically active variants of a native polypeptide of the embodiments (e.g., SEQ ID NOs: 13-21), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 2 provides potential substitutions that can be made in a recombinant meganuclease monomer or subunit to enhance specificity based on the base present at each half-site position (−1 through −9) of a recognition half-site.

TABLE 2

| Posn. | Favored Sense-Strand Base | | | | | | | | | |
|---|---|---|---|---|---|---|---|---|---|---|
| | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | | K28* | C28* | | | M66 |
| | | | | | | | | Q42 | | | K66 |

TABLE 2-continued

| | | | | Favored Sense-Strand Base | | | | | | | |
|---|---|---|---|---|---|---|---|---|---|---|---|
| Posn. | A | C | G | T | A/T | A/C | A/G | C/T | G/T | A/G/T | A/C/G/T |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | | C38 | | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | | D32 | | S32 |
| | | | K32 | V32 | | | | | I32 | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein. An asterisk indicates that the residue contacts the base on the antisense strand.

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave recognition sequences found within an int22h-1 sequence of a Factor VIII gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Figure 2:
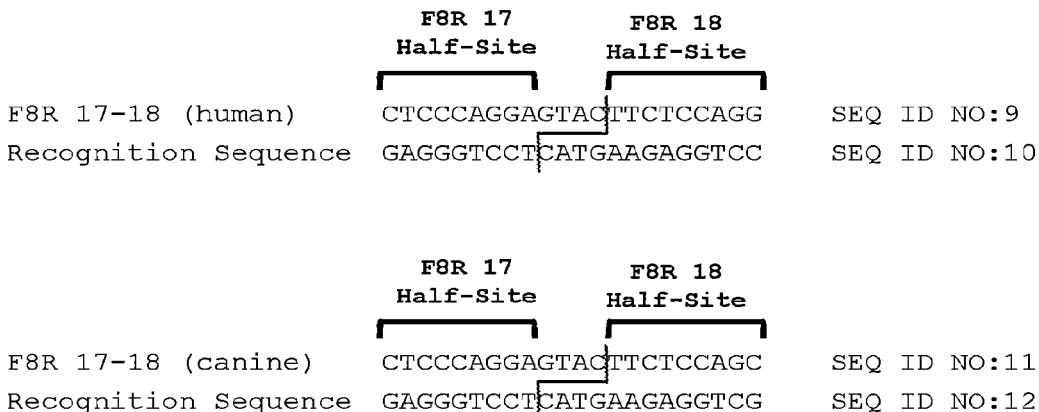
FIG. 2. F8R recognition sequences in the Factor VIII gene. A) Each recognition sequence targeted by a recombinant meganuclease of the invention comprises two recognition half-sites. Each recognition half-site comprises 9 base pairs, separated by a 4 base pair central sequence. The human F8R 17-18 recognition sequence (SEQ ID NO: 9) and canine F8R 17-18 recognition sequence (SEQ ID NO: 11) comprise two recognition half-sites referred to as F8R17 and F8R18.
Figure 3:
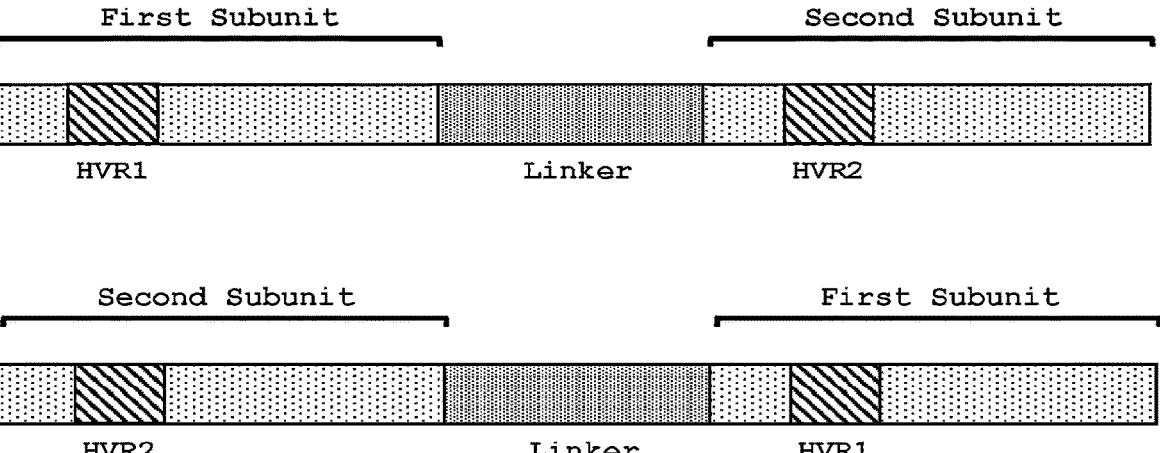
FIG. 3. The recombinant meganucleases of the invention comprise two subunits, wherein the first subunit comprising the HVR1 region binds to a first recognition half-site (i.e., F8R17) and the second subunit comprising the HVR2 region binds to a second recognition half-site (i.e., F8R18). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

Characterization of Meganucleases that Recognize and Cleave F8R Recognition Sequences
1. Meganucleases that Recognize and Cleave the F8R 17-18 Recognition Sequence Recombinant meganucleases (SEQ ID NOs: 13-21), collectively referred to herein as "F8R 17-18 meganucleases," were engineered to recognize and cleave the F8R 17-18 recognition sequence in the human genome (SEQ ID NO: 9), and the F8R 17-18 recognition sequence in the canine genome (SEQ ID NO: 11). Each recognition sequence is present in the Factor VIII gene, specifically within the int22h-1 sequence, and more specifically within the F8A1 sequence. Each F8R 17-18 recombinant meganuclease comprises an N-terminal nuclease-localization signal derived from SV40, a first meganuclease subunit, a linker sequence, and a second meganuclease subunit. A first subunit in each F8R 17-18 meganuclease binds to the F8R17 recognition half-site of SEQ ID NO: 9 or SEQ ID NO: 11, while a second subunit binds to the F8R18 recognition half-site (see, FIG. 2).

The F8R17-binding subunits and F8R18-binding subunits each comprise a 56 base pair hypervariable region, referred to as HVR1 and HVR2, respectively. F8R17-binding subunits are highly conserved outside of the HVR1 region. Similarly, F8R18-binding subunits are also highly conserved outside of the HVR2 region. The F8R17-binding regions of SEQ ID NOs: 13-21 are provided as SEQ ID NOs: 22-30, respectively. Each of SEQ ID NOs: 22-30 share at least 90% sequence identity to SEQ ID NO: 22, which is the F8R17-binding region of the meganuclease F8R 17-18L1.35 (SEQ ID NO: 13). F8R18-binding regions of SEQ ID NOs: 13-21 are provided as SEQ ID NOs: 31-39, respectively. Each of SEQ ID NOs: 31-39 share at least 90% sequence identity to SEQ ID NO: 31, which is the F8R18-binding region of the meganuclease F8R 17-18L1.35 (SEQ ID NO: 13).

2. Cleavage of F8R Recognition Sequences in a CHO Cell Reporter Assay

Figure 4:
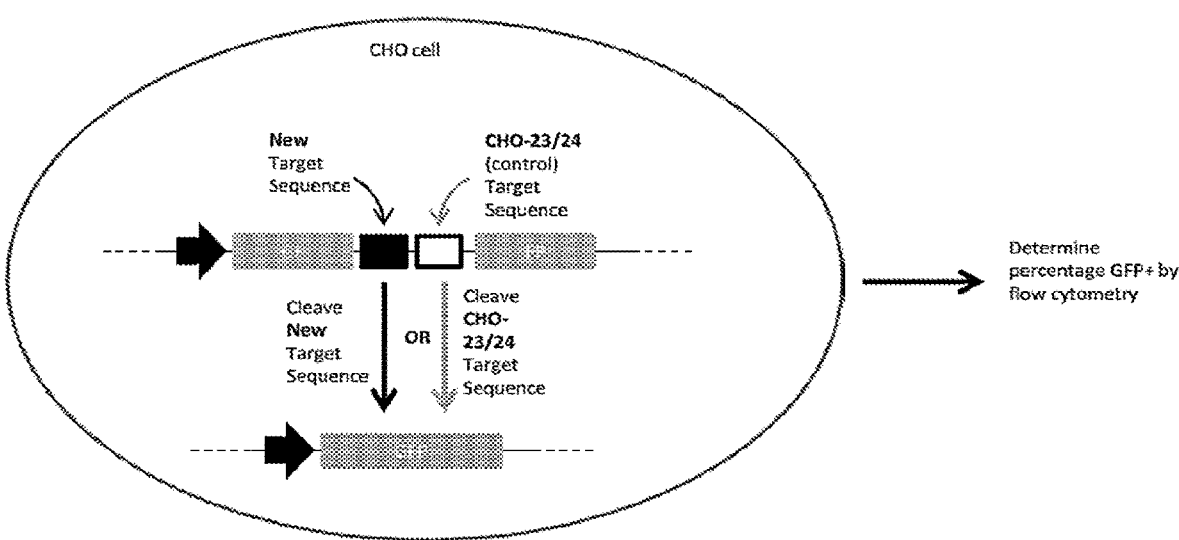
FIG. 4. Schematic of reporter assay in CHO cells for evaluating recombinant meganucleases targeting recognition sequences found in intron 22 of the Factor VIII gene. For the recombinant meganucleases described herein, a CHO cell line was produced in which a reporter cassette was integrated stably into the genome of the cell. The reporter cassette comprised, in 5' to 3' order: an SV40 Early Promoter; the 5' ⅔ of the GFP gene; the recognition sequence for an engineered meganuclease of the invention (i.e., the human or canine F8R 17-18 recognition sequence); the recognition sequence for the CHO-23/24 meganuclease (WO/2012/167192); and the 3' ⅔ of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

To determine whether F8R 17-18 meganucleases could recognize and cleave both the human (SEQ ID NO: 9) and canine (SEQ ID NO: 11) F8R 17-18 recognition sequences, each recombinant meganuclease was evaluated using the CHO cell reporter assay previously described (see, WO/2012/167192 and FIG. 4). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the human F8R 17-18 recognition sequence (SEQ ID NO: 9) or the canine F8R 17-18 recognition sequence (SEQ ID NO: 11). The second recognition sequence inserted into the GFP gene was a CHO-23/24 recognition sequence, which is recognized and cleaved by a control meganuclease called "CHO-23/24". CHO reporter cells comprising the human F8R 17-18 recognition sequence and the CHO-23/24 recognition sequence are referred to as "F8R 17-18h cells." CHO reporter cells comprising the canine F8R 17-18 recognition sequence and the CHO-23/24 recognition sequence are referred to as "F8R 17-18c cells."

Figure 5A:
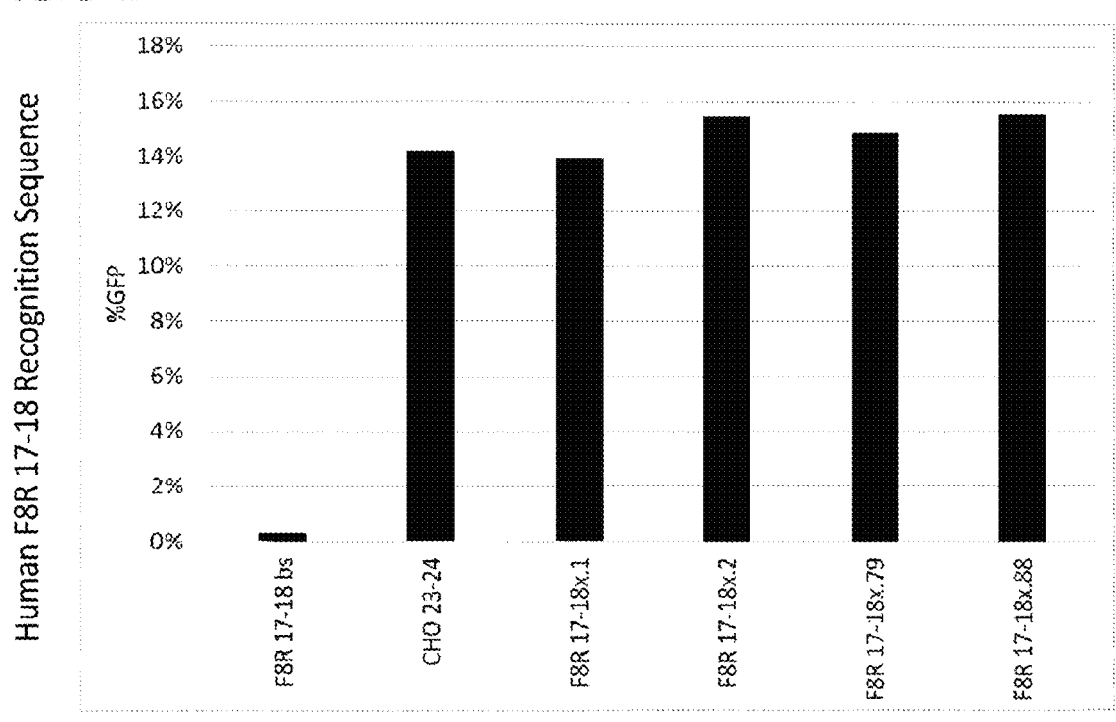
FIG. 5A and FIG. 5B. Efficiency of first-generation recombinant meganucleases for recognizing and cleaving F8R 17-18 recognition sequences in the int22h-1 sequence of the Factor VIII gene in a CHO cell reporter assay. Recombinant meganucleases set forth in SEQ ID NOs: 15 (F8R 17-18x.1), SEQ ID NO: 16 (F8R 17-18x.2), SEQ ID NO: 17 (F8R 17-18x.79), and SEQ ID NO: 18 (F8R 17-18x.88) were engineered to target the human F8R 17-18 recognition sequence (SEQ ID NO: 9) and the canine F8R 17-18 recognition sequence (SEQ ID NO: 11), and were screened for efficacy in the CHO cell reporter assay. The results shown provide the percentage of GFP-expressing cells observed in each assay, which indicates the efficacy of each meganuclease for cleaving a target recognition sequence or the CHO-23/24 recognition sequence. A negative control (bs) was further included in each assay.
Figure 5B:
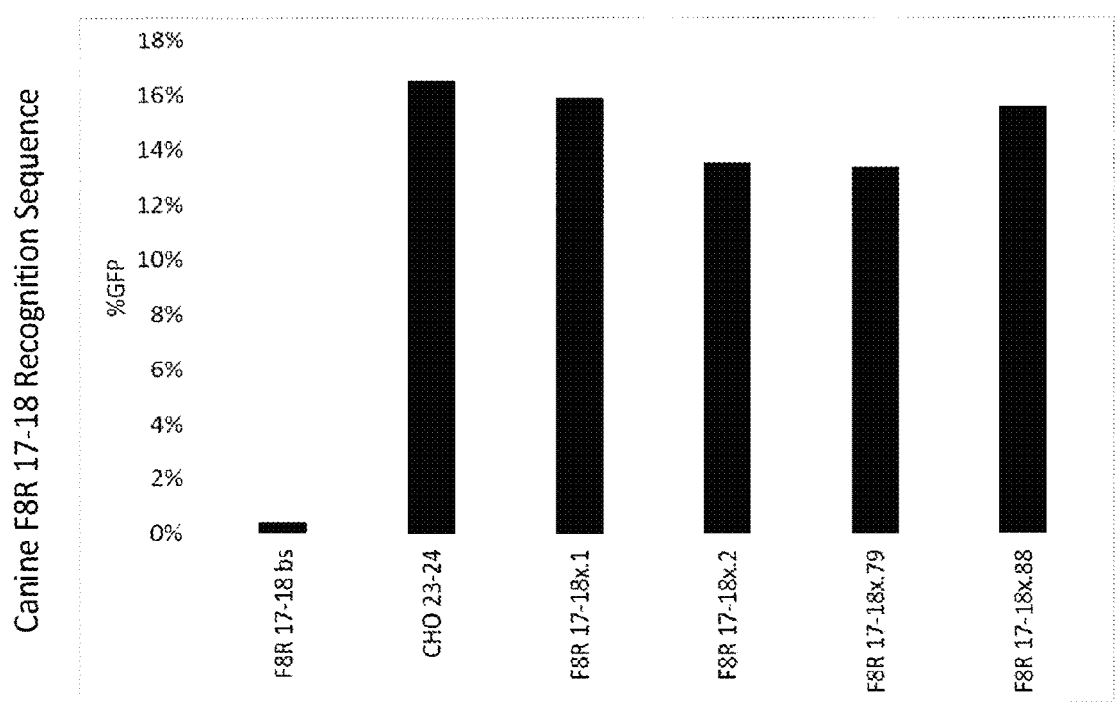
Figure 6A:
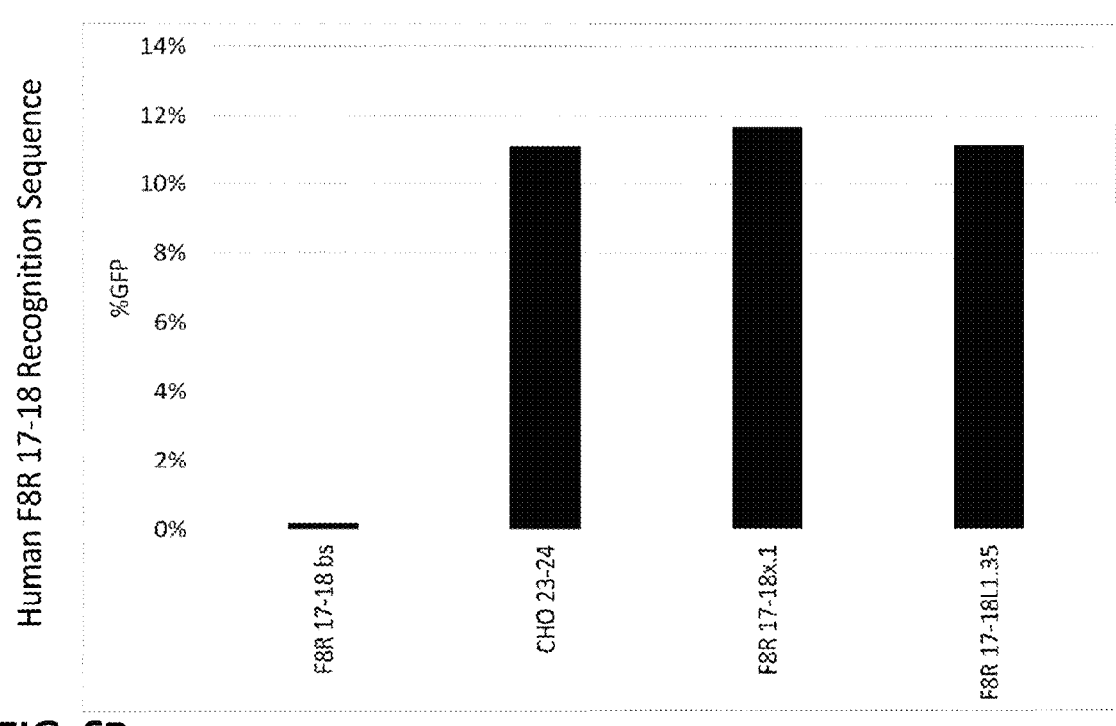
FIG. 6A and FIG. 6B. Efficiency of second-generation engineered meganuclease for recognizing and cleaving recognition sequences in the int22h-1 sequence of the Factor VIII gene in a CHO cell reporter assay. The second-generation engineered meganuclease F8R 17-18L1.35 set forth in SEQ ID NO: 13 was screened for efficacy for targeting the human F8R 17-18 recognition sequence (SEQ ID NO: 9) and the canine F8R 17-18 recognition sequence (SEQ ID NO: 11) in the CHO cell reporter assay and compared to the first-generation recombinant meganuclease F8R 17-18x.1 from which it was derived. The results shown provide the percentage of GFP-expressing cells observed in each assay, which indicates the efficacy of each meganuclease for cleaving a target recognition sequence or the CHO-23/24 recognition sequence. A negative control (bs) was further included in each assay.
Figure 6B:
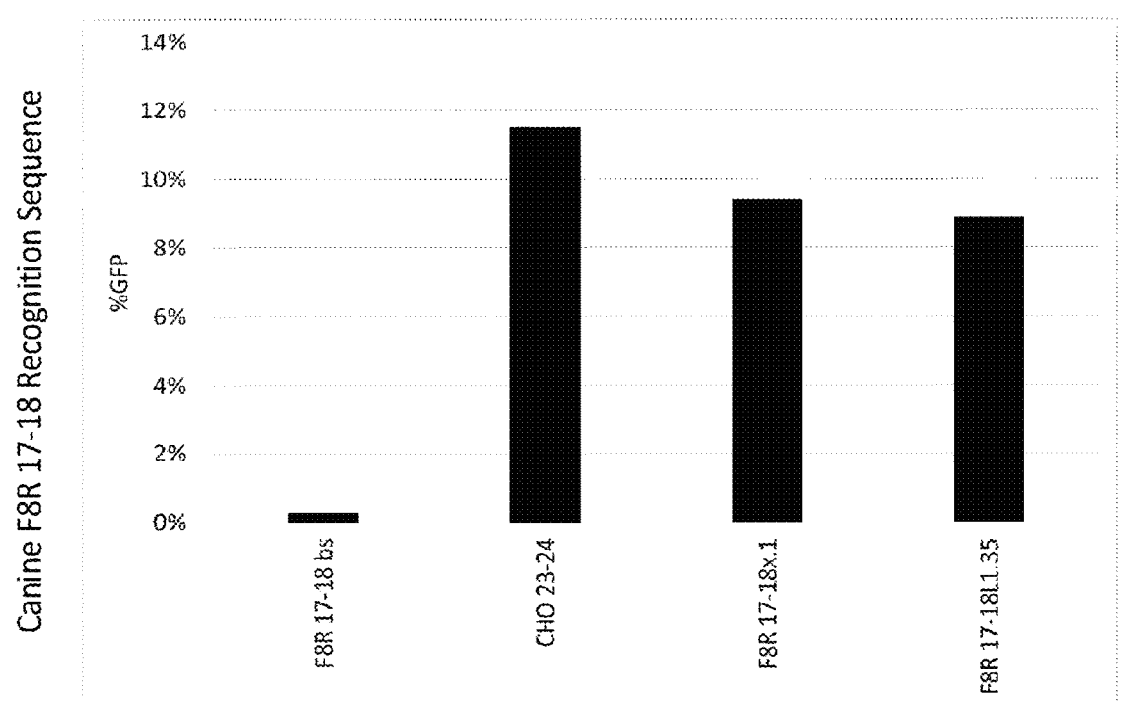
Figure 7A:
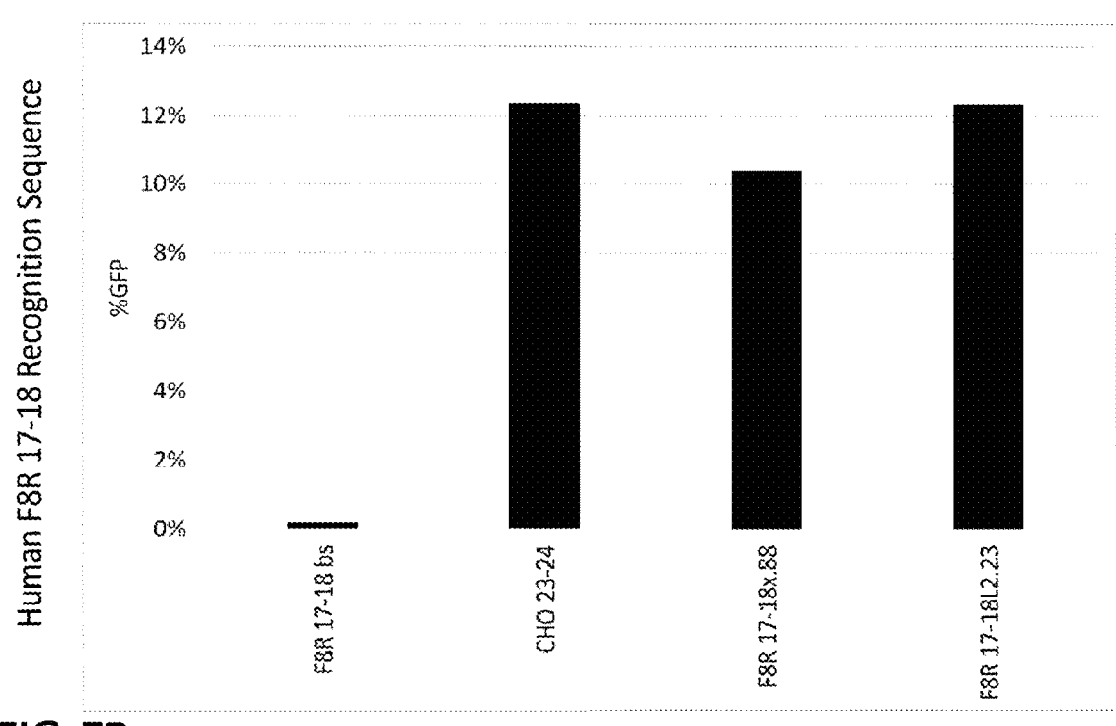
FIG. 7A and FIG. 7B. Efficiency of second-generation engineered meganuclease for recognizing and cleaving recognition sequences in the int22h-1 sequence of the Factor VIII gene in a CHO cell reporter assay. The second-generation engineered meganuclease F8R 17-18L2.23 set forth in SEQ ID NO: 14 was screened for efficacy for targeting the human F8R 17-18 recognition sequence (SEQ ID NO: 9) and the canine F8R 17-18 recognition sequence (SEQ ID NO: 11) in the CHO cell reporter assay and compared to the first-generation recombinant meganuclease F8R 17-18x.88 from which it was derived. The results shown provide the percentage of GFP-expressing cells observed in each assay, which indicates the efficacy of each meganuclease for cleaving a target recognition sequence or the CHO-23/24 recognition sequence. A negative control (bs) was further included in each assay.
Figure 7B:
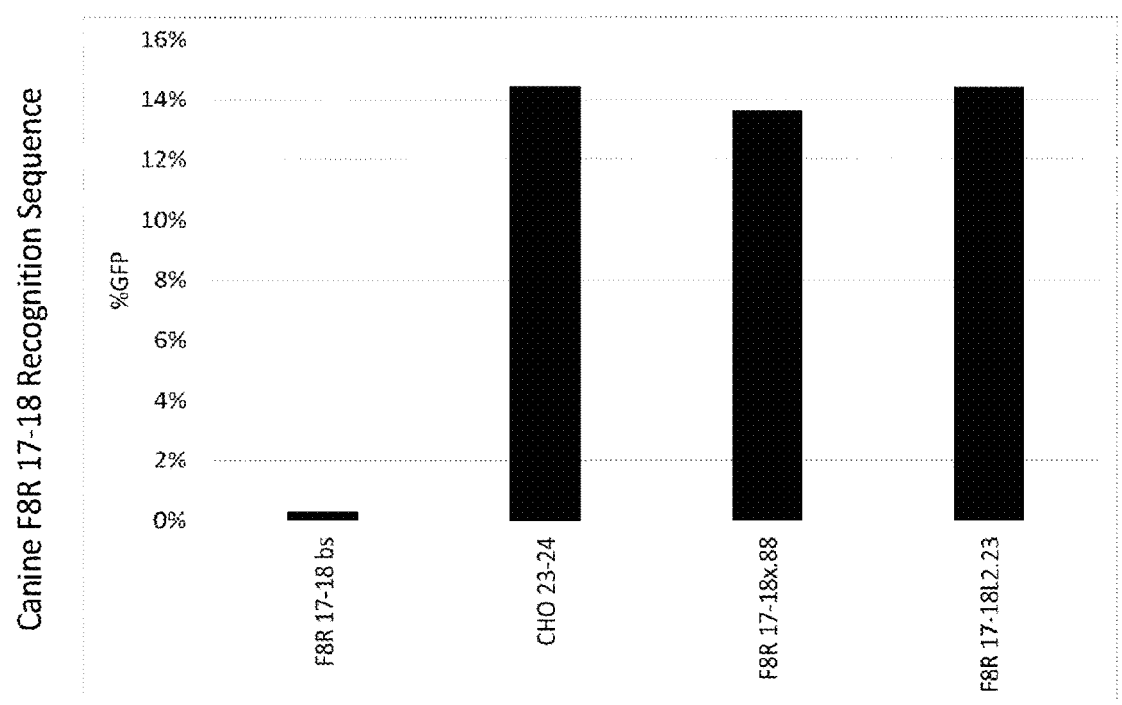

CHO reporter cells were transfected with plasmid DNA encoding their corresponding recombinant meganucleases (e.g., F8R 17-18h cells were transfected with plasmid DNA encoding F8R 17-18 meganucleases) or encoding the CHO-23/34 meganuclease. In each assay, 4e5 CHO reporter cells were transfected with 50 ng of plasmid DNA in a 96-well plate using Lipofectamine® 2000 (ThermoFisher) according to the manufacturer's instructions. At 48 hours post-transfection, cells were evaluated by flow cytometry to determine the percentage of GFP-positive cells compared to an untransfected negative control (F8R bs). As shown in FIG. 5, first-generation F8R 17-18 meganucleases were found to produce GFP-positive cells in cell lines comprising the human (FIG. 5A) or the canine (FIG. 5B) F8R 17-18 recognition sequence at frequencies significantly exceeding the negative control. Similarly, FIG. 6 shows that the second-generation F8R 17-18L1.35 meganuclease also produced GFP-positive cells in cell lines comprising the human (FIG. 6A) or the canine (FIG. 6B) F8R 17-18 recognition sequence at frequencies significantly exceeding the negative control, and comparable to the F8R 17-18x.1 meganuclease from which it was derived. Likewise, FIG. 7 shows that the second-generation F8R 17-18L2.23 meganuclease produced GFP-positive cells in cell lines comprising the human (FIG. 7A) or the canine (FIG. 7B) F8R 17-18 recognition sequence at frequencies significantly exceeding the negative control, and comparable to the F8R 17-18x.88 meganuclease from which it was derived.

The efficacy of F8R 17-18 meganucleases was also determined in a time-dependent manner 2, 5, and 7 days after introduction of the meganucleases into CHO reporter cells. In this study, F8R 17-18h or F8R 17-18c cells (1.0×106) were electroporated with 1×106 copies of F8R 17-18 meganuclease mRNA per cell using a BioRad Gene Pulser Xcell according to the manufacturer's instructions. At the designated time points post-transfection, cells were evaluated by flow cytometry to determine the percentage of GFP-positive cells. A CHO-23/24 meganuclease was also included at each time point as a positive control.

Figure 8A:
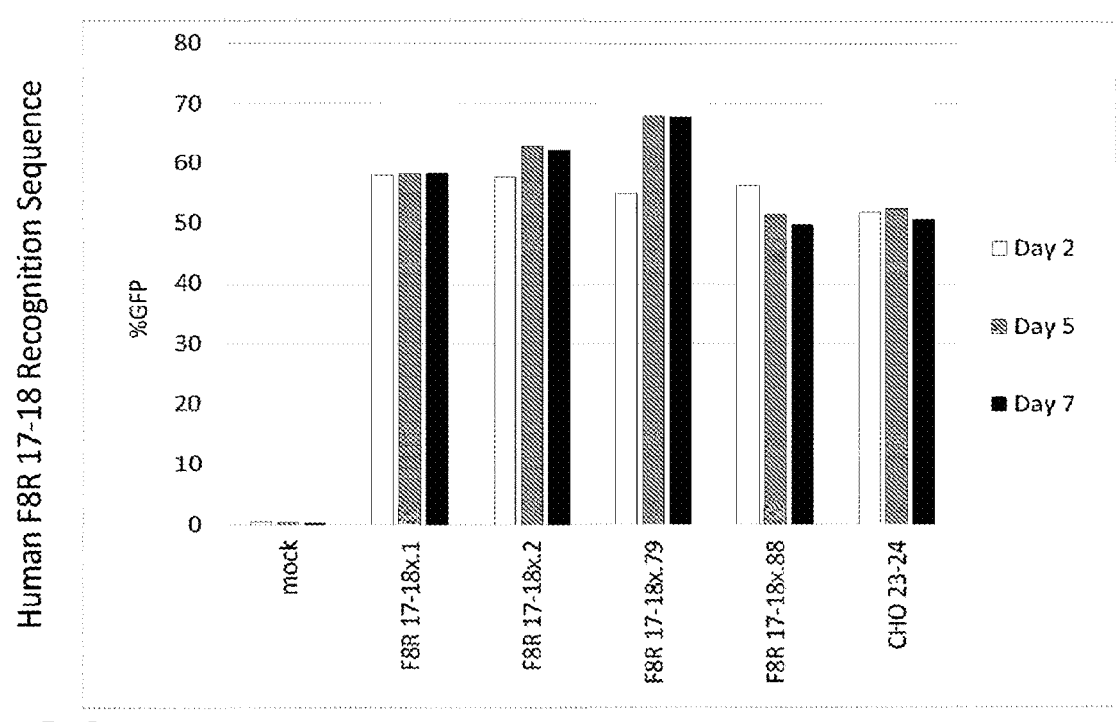
FIG. 8A and FIG. 8B. Engineered meganucleases encompassed by the invention were engineered to target the human F8R 17-18 (SEQ ID NO: 9) and canine F84 17-18 (SEQ ID NO: 11) recognition sequences, and were screened for efficacy in the CHO cell reporter assay at multiple time points over 7 days after nucleofection. The results shown provide the percentage of GFP-expressing cells observed in each assay at days 2, 5, and 7, which indicates the efficacy of each meganuclease for cleaving a target recognition sequence or the CHO-23/24 recognition sequence as a function of time.
Figure 8B:
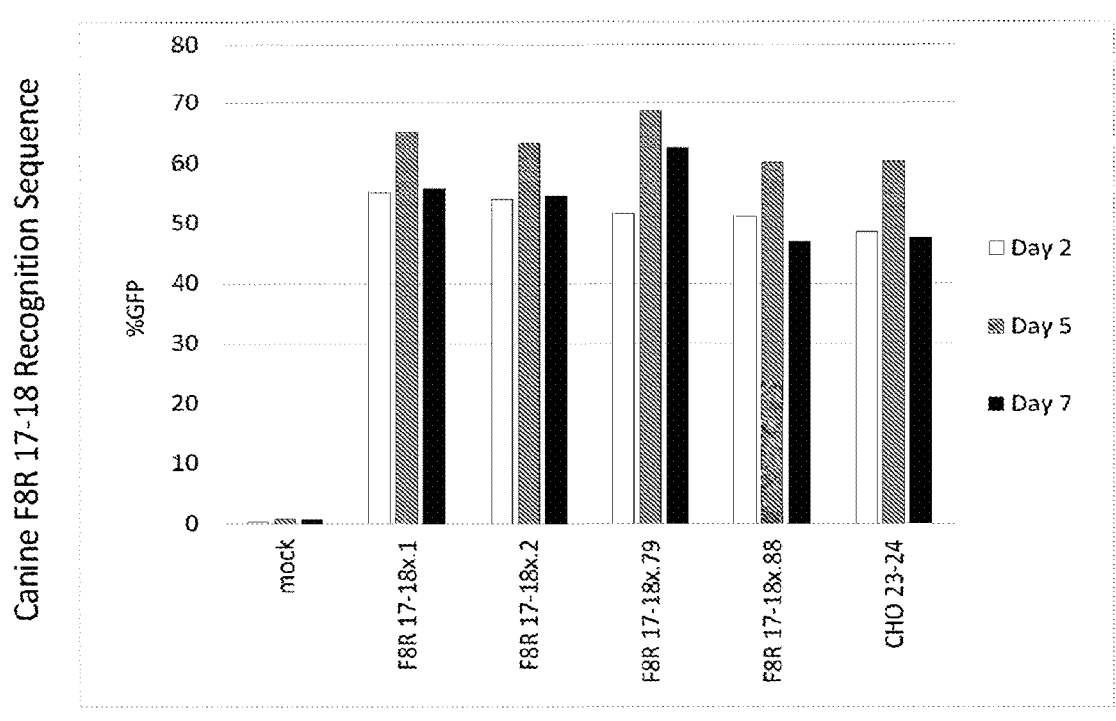

As shown in FIG. 8, the % GFP produced by F8R 17-18 meganucleases was relatively consistent over the time course of each study in both F8R 17-18h (FIG. 8A) and F8R 17-18c (FIG. 8B) cells, indicating persistent cleavage activity and a lack of any substantial toxicity in the cells.

3. Reduced Off-Target Cutting in a Cell Reporter Assay by Optimized F8R Nucleases Analysis of off-target cutting by second-generation F8R meganucleases (which are specific for SEQ ID NOs: 9 and 11) revealed an off-target recognition sequence which is cleaved at some frequency in cells. This recognition site is referred to herein as "nf2" and is set forth in SEQ ID NO: 46.

Third-generation F8R nucleases were engineered to reduce cutting of the off-target site, while maintaining specificity for both the human and canine recognition sequences (SEQ ID NOs: 9 and 11). The CHO cell reporter assay used to evaluate the third-generation F8R nucleases is similar to that described above. In CHO reporter cell lines developed for this study, one recognition sequence inserted into the GFP gene was the human F8R 17-18 recognition sequence (SEQ ID NO: 9), the canine F8R 17-18 recognition sequence (SEQ ID NO: 11), or the nf2 off-target recognition sequence (SEQ ID NO: 46). The second recognition sequence inserted into the GFP gene was a CHO-23/24 recognition sequence, which is recognized and cleaved by a control meganuclease called "CHO-23/24". CHO reporter cells comprising the human F8R 17-18 recognition sequence and the CHO-23/24 recognition sequence are referred to as "F8R 17-18h cells." CHO reporter cells comprising the canine F8R 17-18 recognition sequence and the CHO-23/24 recognition sequence are referred to as "F8R 17-18c cells." CHO reporter cells comprising the nf2 off-target recognition sequence and the CHO-23/24 recognition sequence are referred to as "Off-target cells."

CHO reporter cells were transfected with mRNA encoding either the F8R 17-18L1.35 meganuclease, or third-generation nucleases including F8R 17-18L.553, F8R 17-18L.615, or F8R 17-18L.626. CHO reporter cells were also transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. F8R 17-18h and F8R 17-18c cells were evaluated by flow cytometry at 48 hours, 120 hours and 168 hours to determine the percentage of GFP-positive cells compared to an untransfected negative control. F8R 17-18 off-target cells were evaluated by flow cytometry at 48 hours only. Data obtained at each time point was normalized to the % GFP positive cells observed using the CHO-23/24 meganuclease to determine an "activity score" and the normalized data from the earliest time point was subtracted from that of the latest time point to determine a "toxicity score". The activity and toxicity scores were then added together to determine an "activity index," which was then normalized to the activity index of the CHO-23/24 meganuclease to compare data between cell lines.

Figure 9:
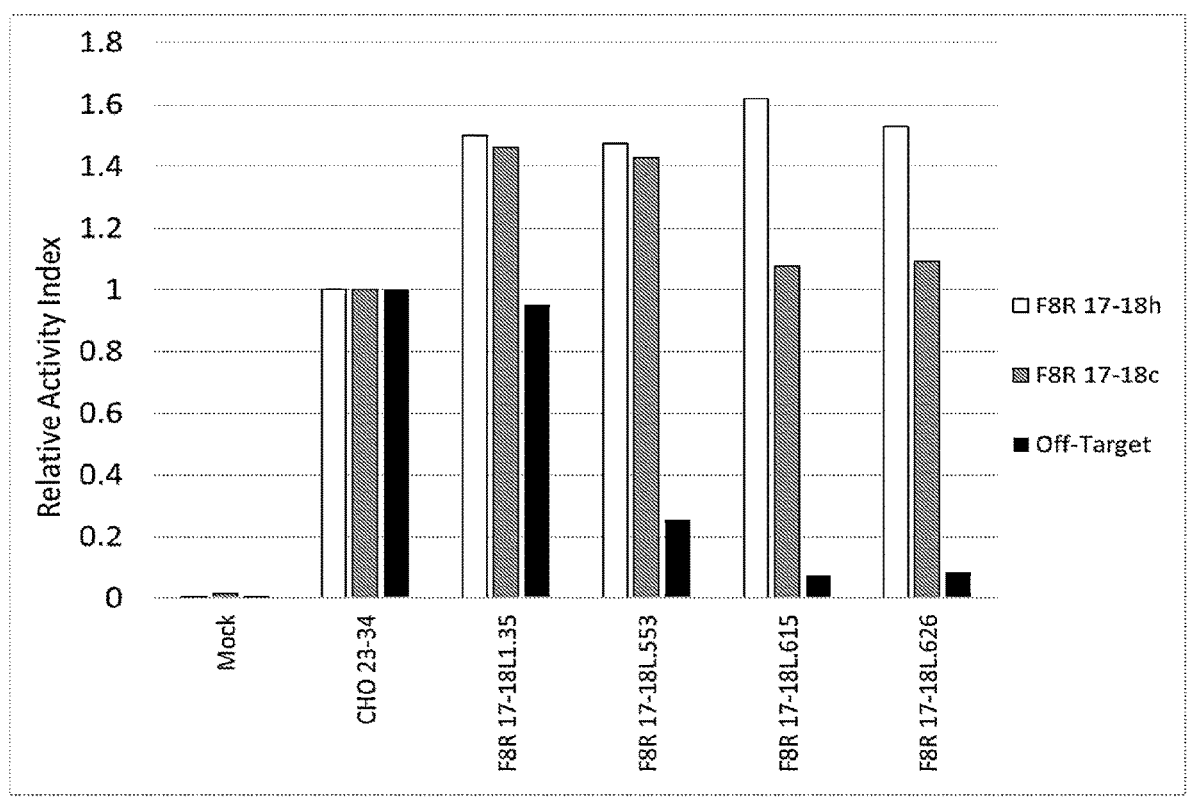
FIG. 9. Efficiency of third-generation engineered meganucleases for recognizing and cleaving human and canine F8R recognition sequences, and for reducing cleavage of an off-target recognition sequence, in a CHO cell reporter assay. Third-generation engineered meganucleases were screened for efficacy for targeting the human F8R 17-18 recognition sequence (SEQ ID NO: 9), the canine F8R 17-18 recognition sequence (SEQ ID NO: 11), or an off-target sequence (SEQ ID NO: 46), in the CHO cell reporter assay and were compared to the F8R 17-18L1.35 meganuclease.

As shown in FIG. 9, the F8R 17-18L1.35 meganuclease cleaved both the human and canine F8R 17-18 recognition sequences with high frequency, while also showing cleavage of the nf2 off-target site. However, each of the optimized third-generation nucleases maintained a high efficiency of on-target cutting of the human and canine F8R 17-18 recognition sequences, while drastically reducing cleavage of the nf2 off-target recognition sequence. In particular, the F8R 17-18L.615 and F8R 17-18L.626 nucleases exhibited to lowest frequencies of cleavage of the off-target site.

4. Conclusions

These studies demonstrated that F8R meganucleases encompassed by the invention can efficiently target and cleave their respective recognition sequences in cells. Further, these studies demonstrated that optimized third-generation nucleases could be developed to improve specificity for the on-target human and canine recognition sequences while reducing cleavage of off-target sequences.

Example 2

Reversion of Exons 1-22 in the Human Factor VIII Gene in Patient T Cells

1. Methods

This study demonstrated that F8R 17-18 nucleases encompassed by the invention could lead to the reversion of the hemophilia A specific Factor VIII gene inversion in hemophilia A patient T cells.

Hemophilia A patient T-cells (1×10^6) were transfected with mRNA (1 µg) encoding F8R17-18x.1, F8R17-18x.2, F8R17-18x.79, or F8R17-18x.88, respectively, using a Lonza 4D nucleofector according to the manufacturer's instructions. At 3 days post-transfection, genomic DNA was isolated from cells and long-distance PCR was performed to determine Factor VIII genome editing. Genomic DNA isolated from untreated normal T-cells, as well as patient T cells transfected with mRNA encoding green fluorescent protein (GFP) and F8R11-12.x69 nuclease, respectively, served as controls.

In this long-distance PCR, the genomic DNA was amplified between primers H1U/H1D and H3D/H1D, respectively.

```
H1U:
                              (SEQ ID NO: 40)
[5'-CCCTTACAGTTATTAACTACTCTCATGAGGTTCATTCC-3']

H1D:
                              (SEQ ID NO: 41)
[5'-GGCCCTACAACCATTCTGCCTTTCACTTTCAGTGCAATA-3']

H3D:
                              (SEQ ID NO: 42)
[5'-CACAAGGGGGAAGAGTGTGAGGGTGTGGGATAAGAA-3']
```

Primers H1U and H1D bind upstream and downstream, respectively of the int22h-1 repeat in intron 22 of the Factor VIII gene; primer H3D binds downstream of a near-identical, inversely oriented copy of the int22h-1 repeat located about 0.5 Mb upstream of int22h-1.

Figure 10B:
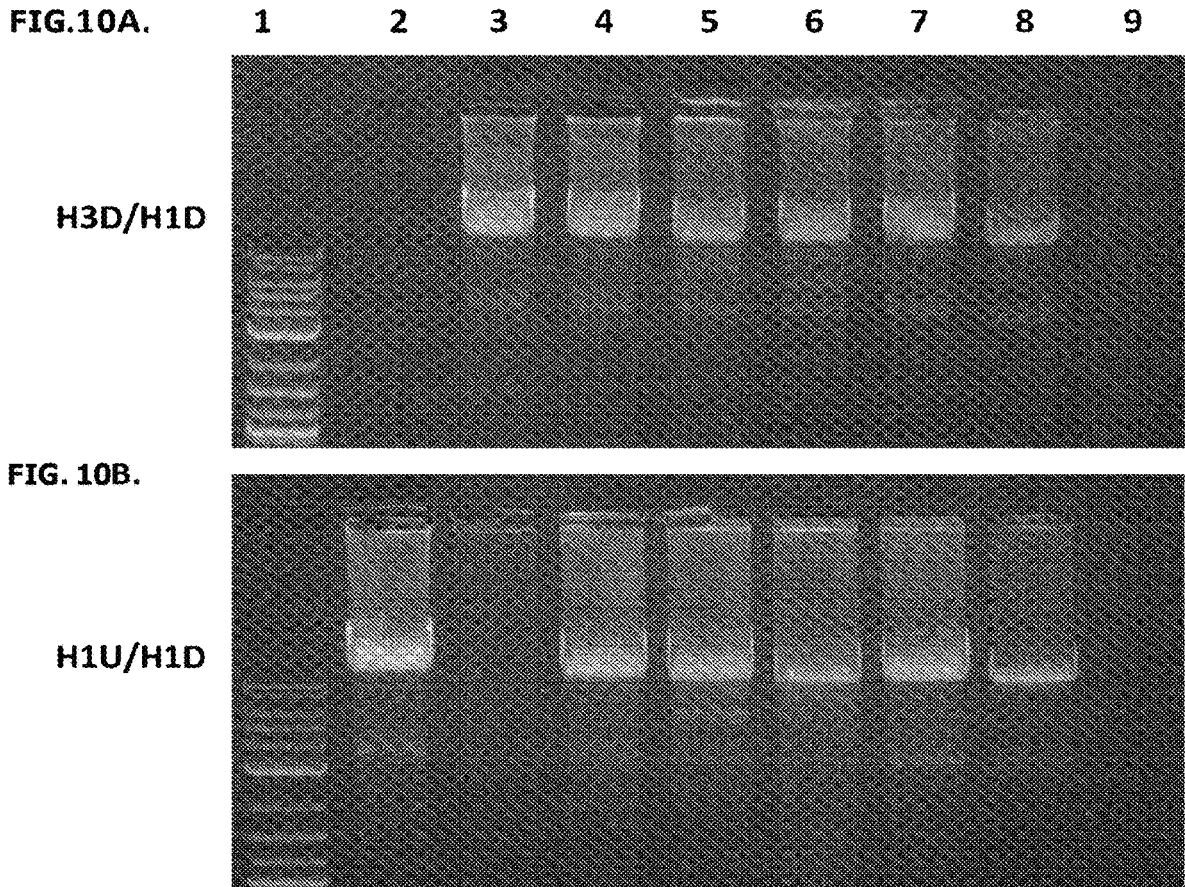

FIG. 10 shows the gels obtained following the long-distance PCR. FIG. 10A shows the result of using the H3D/H1D primer pair. FIG. 10B shows the result of using the H1U/H1D primer pair. In each figure, lane 1 is a molecular weight standard, lane 2 is gDNA obtained from normal human T cells, and lanes 3-8 show gDNA obtained from hemophilia A patient T cells treated with mRNA for GFP (lane 3), the F8R 11-12x.69 meganuclease (which targets a separate recognition site (F8R 11-12) in the int22h-1 region that is only present in the human genome) (lane 4), the F8R 17-18x.1 meganuclease (lane 5), the F8R 17-18x.2 meganuclease (lane 6), the F8R 17-18x.79 meganuclease (lane 7), or the F8R 17-18x.88 meganuclease (lane 8). Lane 9 is blank.

Long-distance PCR of genomic DNA from normal human T cells with primers H1U/H1D yields an approximately 11 kb amplicon (FIG. 10B, lane 2) while PCR with primers H3D/H1D does not generate an amplification product (FIG. 10A, lane 2). Conversely, long-distance PCR of genomic DNA from patient cells with the hemophilia A gene inversion treated with GFP mRNA using primers H1U/H1D fails to generate a PCR product (FIG. 10B, lane 3) while the H3D/H1D PCR yields an approximately 11 kb amplicon (FIG. 10A, lane 3).

Upon successful reversion of the genomic fragment in patient T cells between two inversely oriented int22h repeats, the H1U primer binding site, which is located on the inverted fragment, is reoriented relative to the H1D and H3D primer binding sites. Now the H1U/H1D PCR yields the 11 kb amplicon (FIG. 10B, lanes 4 through 8), indicating a reversion to the wild-type configuration of the Factor VIII gene. PCR fragments were analyzed by agarose gel electrophoresis and visualized by ethidium bromide.

2. Results

Genomic DNAs from hemophilia A patient T cells treated with mRNA encoding F8R17-18x.1, F8R17-18x.2, F8R17-18x.79 and F8R17-18x.88 nucleases (or GFP as a control) were analyzed by long-distance PCR (FIG. 10). Only the H3D/H1D fragment could be amplified from genomic DNA isolated from patient T-cells treated with GFP mRNA (FIG. 10A, lane 3). Using genomic DNA from F8R17-18x.1, F8R17-18x.2, F8R17-18x.79 and F8R17-18x.88 nuclease-treated patient T cells as PCR template, both H1U/H1D and H3D/H1D primer combinations yielded their signature wild-type (~11 kb) and inversion (~11 kb) amplicons, respectively (FIG. 10A, lanes 5-8, and FIG. 10B, lanes 5-8). The H3U/H1D fragment was still being amplified from genomic DNA from F8R nuclease-treated patient T-cells because the nuclease treatment generated a mixed population of cells with edited and unedited genomes.

3. Conclusions

F8R 17-18 meganucleases encompassed by the invention were capable of inducing a reversion of the inverted Factor VIII gene back to a wild-type configuration in hemophilia A patient T cells in vitro, and this reversion could be detected by long-distance PCR.

Example 3

Inversion of Exons 1-22 in the Human Factor VIII Gene in HEK293 Cells

1. Methods

Nucleases F8R 17-18x.1 and F8R 17-18x.88 were optimized with respect to their specificity for the human and canine F8R 17-18 recognition sequences. Two improved nucleases, F8R 17-18L1.35 (derived from F8R 17-18x.1) and F8R 17-18L2.23 (derived from F8R 17-18x.88), were evaluated in HEK293 cells for their ability to cause the Factor VIII locus inversion characteristic of a subset of hemophilia A patients.

HEK293 cells were transfected with mRNA encoding F8R17-18L1.35 and F8R17-18L2.23 (both in triplicate) and long-distance PCR was performed, essentially as described in Example 2. Genomic DNA isolated from HEK293 cells transfected with mRNA encoding green fluorescent protein (GFP) as well as F8R17-18x.1 and F8R17-18x.88 nucleases, respectively, served as controls.

Figures 11A, 11B:
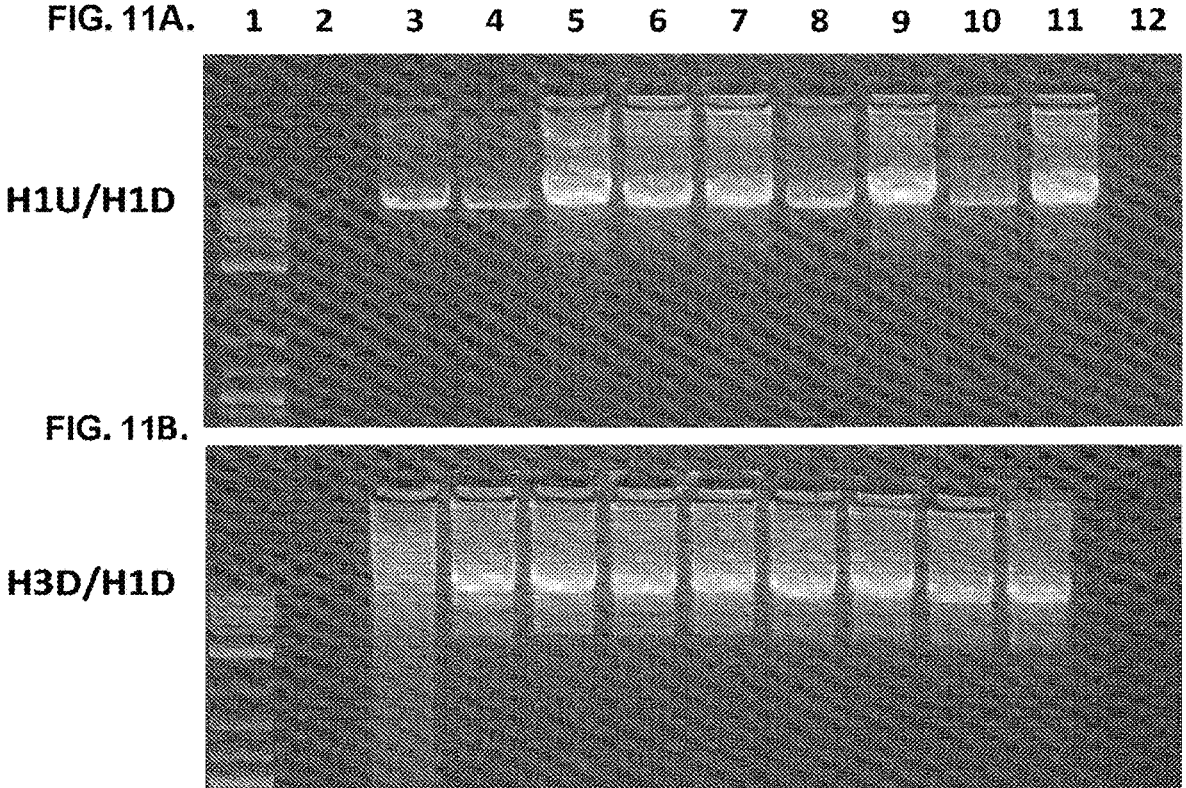
FIG. 11A and FIG. 11B. Inversion of exons 1-22 in the Factor VIII gene by F8R nucleases in HEK293 cells and determination of editing by long-distance PCR. HEK293 cells were transfected with mRNA encoding F8R 17-18x.1, F8R 17-18x.88, F8R 17-18L1.35, or F8R 17-18L2.23 nucleases. At 3 days post-transfection, genomic DNA was isolated from cells and long-distance PCR was performed to determine Factor VIII genome editing.

Gels obtained from the long-distance PCR are shown in FIG. 11. FIG. 11A shows the result of using the H1U/H1D primer pair. FIG. 11B shows the result of using the H3D/H1D primer pair. In each figure, lane 1 is a molecular weight standard, lanes 2 and 12 are blank, lane 3 is gDNA obtained from untreated HEK293 cells, and lanes 3-8 show gDNA obtained from HEK293 cells treated with mRNA for GFP (lane 3), the F8R 17-18x.1 meganuclease (lane 4), the F8R 17-18x.88 meganuclease (lane 5), the F8R 17-18L1.35 meganuclease (lanes 6-8), or the F8R 17-18L2.23 meganuclease (lanes 9-11).

2. Results

Genomic DNAs from HEK293 cells treated with mRNA encoding F8R 17-18L1.35 and F8R 17-18L2.23 nucleases (or GFP as a control) were analyzed by long-distance PCR (FIG. 11). Only the H1U/H1D fragment could be amplified from genomic DNA isolated from HEK293 cells treated with GFP mRNA (FIG. 11A, lane 3; but not FIG. 11B, lane 3). Using genomic DNA from F8R 17-18L1.35 and F8R 17-18L2.23 nuclease-treated 293 cells as PCR template, both H1U/H1D and H3D/H1D primer combinations yielded their signature wild-type (~11 kb) and inversion (~11 kb) amplicons, respectively (FIG. 11A, lanes 6-11; FIG. 11B, lanes 6-11). The H1U/H1D fragment could still be amplified from genomic DNA from F8R 17-18 nuclease-treated HEK293 cells because the nuclease treatment generated a mixed population of cells with edited and unedited genomes.

3. Conclusions

The optimized F8R 17-18 meganucleases were capable of inducing an inversion of the Factor VIII locus in HEK293 cells in vitro, and this inversion could be detected by long-distance PCR.

Example 4

Inversion of Exons 1-22 in the Canine Factor VIII Gene in MDCK Cells

1. Methods

This study demonstrated that F8R 17-18 meganucleases encompassed by this invention can lead to the hemophilia A-specific Factor VIII gene inversion in canine MDCK cells. In addition, the described method can be used to determine the efficiency of F8R nuclease-mediated Factor VIII gene inversion.

MDCK cells (1×10^6) were transfected with mRNA (1 μg) encoding F8R 17-18x.1, F8R 17-18x.2, F8R 17-18x.79 and F8R 17-18x.88 meganucleases, respectively, using the ThermoFisher Neon Transfection System according to the manufacturer's instructions. At 3 days post-transfection, genomic DNA was isolated from cells and inverse digital PCR was performed to determine Factor VIII genome editing. Genomic DNA isolated from MDCK cells transfected with mRNA encoding green fluorescent protein (GFP) served as a control.

Genomic DNA was digested to completion with restriction endonuclease BclI. Digested DNA was circularized using T4 DNA ligase and analyzed by inverse digital PCR using the Bio-Rad QX200 Digital PCR System according to the manufacturer's instructions.

In normal canine genomic DNA, the BclI digest generates an approximately 12 kb fragment encompassing the int22h-1 repeat in intron 22 of the Factor VIII gene as well as an approximately 9 kb fragment encompassing a near-identical, inversely oriented copy of the int22h-1 repeat located about 0.5 Mb upstream of int22h-1.

In inverse digital PCR, the two circularized BclI fragments described above are amplified with primers flanking the respective BclI sites. Primers U1 and D1 bind upstream and downstream, respectively, of the int22h-1 repeat in intron 22 of the Factor VIII gene; primer U3 binds upstream of a near-identical, inversely oriented copy of the int22h-1 repeat located about 0.5 Mb upstream of int22h-1. All primers bind the genomic DNA in opposite orientation to conventional PCR and generate amplicons only when the BclI fragments are circularized.

```
U1:
                                    (SEQ ID NO: 43)
    [5'-GAGCCAGTTGTGTACCAT-3']

D1:
                                    (SEQ ID NO: 44)
    [5'-ACGTGATCCCGATTTGAATA-3']

U3:
                                    (SEQ ID NO: 45)
    [5'-GCACCTTACTGTCCTGAT-3']
```

Inverse digital PCR of BclI-digested and circularized MDCK genomic DNA with primers U1/D1 yields an approximately 0.5 kb amplicon that can be detected using a TaqMan probe while PCR with primers U3/U1 does not generate an amplification product.

Upon successful inversion of the genomic fragment between int22h-1 and its distal copy, the U1 primer binding site, which is located on the inverted fragment, is reoriented relative to the D1 and U3 primer binding sites. Now, the U1/D1 PCR fails to generate a PCR product, while the U3/U1 PCR yields an approximately 0.5 kb amplicon which can be detected with the same TaqMan probe.

Figures 12A, 12B:
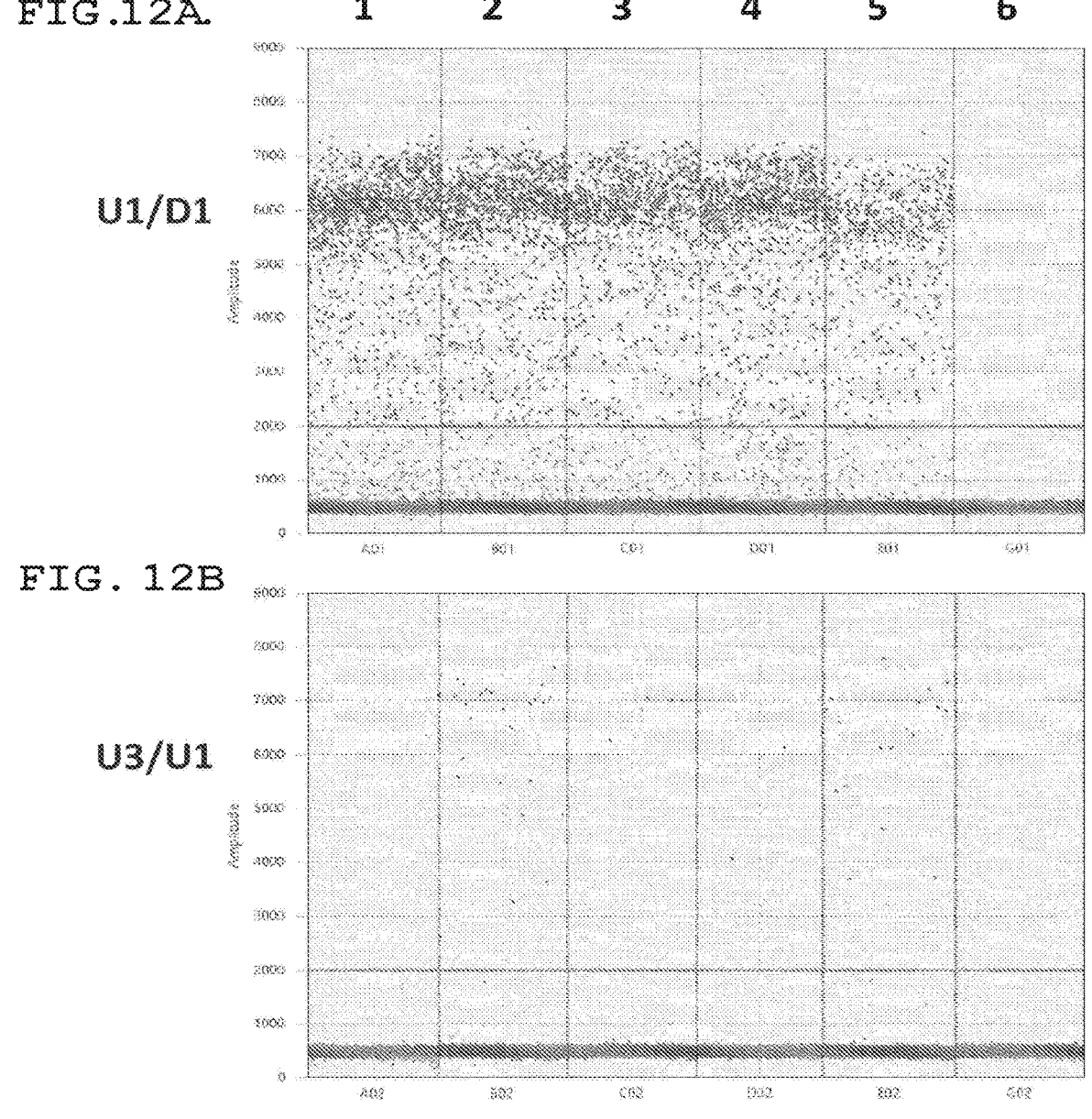
FIG. 12A and FIG. 12B. Inversion of exons 1-22 in the Factor VIII gene by F8R nucleases in canine cells. MDCK cells were transfected with mRNA encoding F8R 17-18x.1, F8R 17-18x.2, F8R 17-18x.79, or F8R 17-18x.88 nucleases. At 3 days post-transfection, genomic DNA was isolated from cells and inverse digital PCR was performed to determine Factor VIII genome editing.

FIG. 12 shows the results of the digital PCR performed in this study. FIG. 12A shows the results obtained using the U1/D1 primer pair. FIG. 12B shows the results obtained using the U3/U1 primer pair. In each figure, the lanes are as follows: lane 1, MDCK cells treated with mRNA encoding GFP; lane 2, MDCK cells treated with mRNA encoding the F8R 17-18x.1 meganuclease; lane 3, MDCK cells treated with mRNA encoding the F8R 17-18x.2 meganuclease; lane 4, MDCK cells treated with mRNA encoding the F8R 17-18x.79 meganuclease; lane 5, MDCK cells treated with mRNA encoding the F8R 17-18x.88 meganuclease; lane 6, no template control.

2. Results

Genomic DNAs from MDCK cells treated with GFP and MDCK cells treated with F8R17-18x.1, F8R17-18x.2, F8R17-18x.79 and F8R17-18x.88 nucleases, respectively, were analyzed by inverse digital PCR. Only the U1/D1 fragment was amplified from genomic DNA isolated from GFP-treated MDCK cells (FIG. 12A, lane 1), while the U3/U1 PCR did not generate a signal (FIG. 12B, lane 1). Using genomic DNA from F8R nuclease-treated MDCK cells, both U1/D1 and U3/U1 amplicons were detected (FIG. 12A, lane 2-5, and FIG. 12B, lanes 2-5). The U1/D1 fragment was still amplified from genomic DNA from F8R nuclease-treated MDCK cells because the nuclease treatment generated a mixed population of cells with both edited and unedited genomes. Since digital PCR allows parallel analysis of hundreds to thousands of chromosome equivalents, the Factor VIII gene inversion efficiency could be calculated. Out of the total number of Factor VIII genes detected by this assay, 0.3 to 2.8% showed an inversion as a result of the activity of nucleases F8R17-18x.1, F8R17-18x.2, F8R17-18x.79 and F8R17-18x.88, respectively.

3. Conclusions

Inverse digital PCR detected Factor VIII gene inversion in MDCK cells treated with nucleases F8R17-18x.1, F8R17-18x.2, F8R17-18x.79 and F8R17-18x.88. In addition, using inverse digital PCR, the editing efficiency could be calculated. Depending on the nuclease, up to 2.8% of the detected Factor VIII genes in MDCK cells were edited. Importantly, this study further demonstrates that Factor VIII gene inversions can be induced by DNA double-strand breaks within the int22h repeats, and that F8R 17-18 nucleases can induce a flipping of the intron in both human and canine cells.

Example 5

Inversion of Exons 1-22 in the Canine Factor VIII Gene in MDCK Cells

1. Methods

As previously discussed, the F8R 17-18x.1 and F8R 17-18x.88 meganucleases were optimized with respect to their specificity for the human and canine F8R 17-18 recognition sequence. In this study, the optimized F8R 17-18L1.35 and F8R17-18L2.23 meganucleases were evaluated in MDCK cells for their ability to cause the Factor VIII locus inversion characteristic of a subset of hemophilia A patients.

MDCK cells were transfected with mRNA encoding F8R 17-18L1.35 or F8R 17-18L2.23 and inverse digital PCR was performed, essentially as described in Example 4. Genomic DNA isolated from MDCK cells transfected with mRNA encoding green fluorescent protein (GFP) as well as F8R 17-18x.1 and F8R 17-18x.88 nucleases, respectively, served as controls.

Figures 13A, 13B:
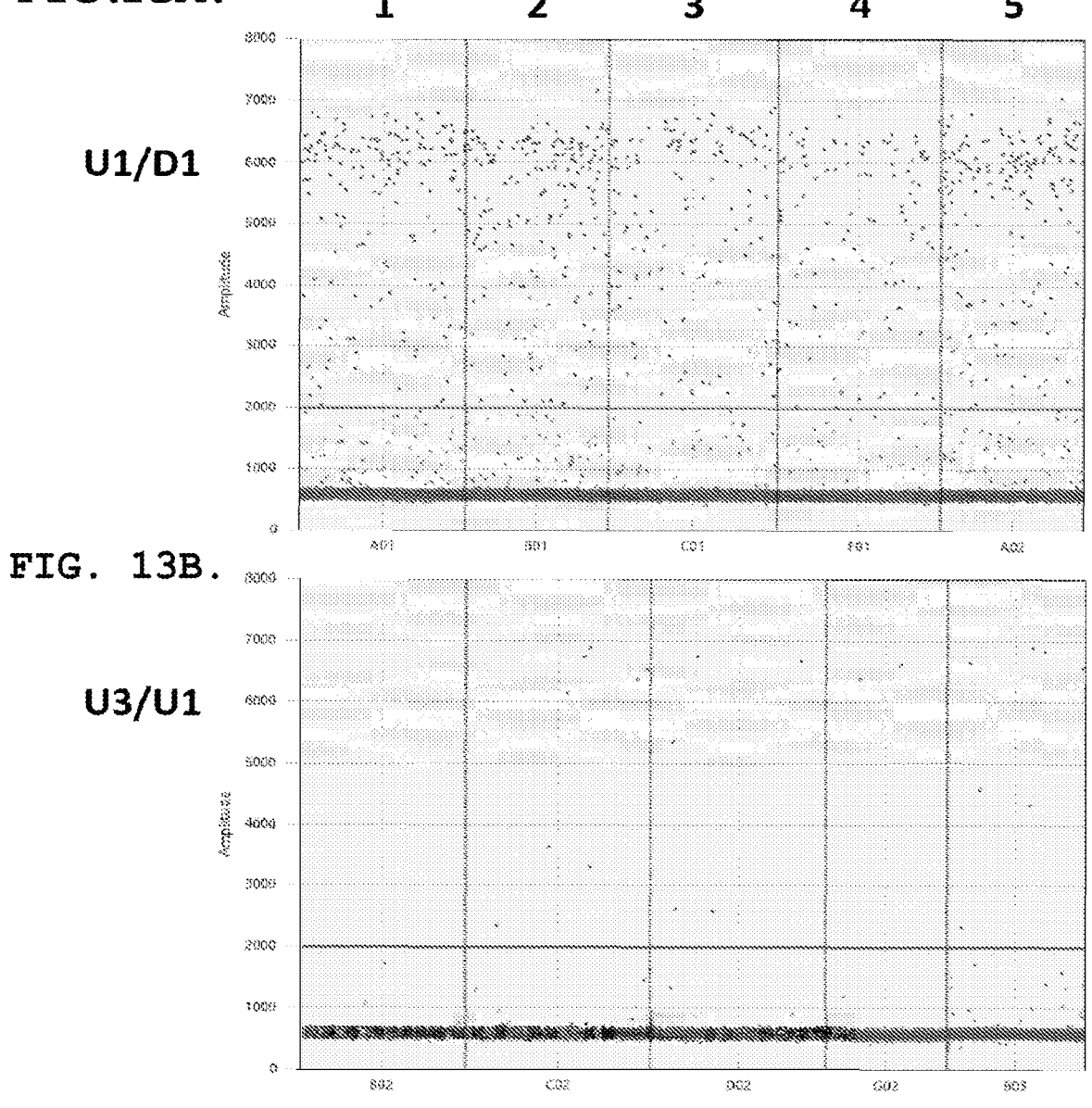
FIG. 13A and FIG. 13B. Inversion of exons 1-22 in the Factor VIII gene by F8R nucleases in canine cells. MDCK cells were transfected with mRNA encoding F8R 17-18x.1, F8R 17-18x.88, F8R 17-18L1.35, or F8R 17-18L2.23 nucleases. At 3 days post-transfection, genomic DNA was isolated from cells and inverse digital PCR was performed to determine Factor VIII genome editing.

FIG. 13 shows the results of the digital PCR performed in this study. FIG. 13A shows the results obtained using the U1/D1 primer pair. FIG. 13B shows the results obtained using the U3/U1 primer pair. In each figure, the lanes are as follows: lane 1, MDCK cells treated with mRNA encoding GFP; lane 2, MDCK cells treated with mRNA encoding the F8R 17-18x.1 meganuclease; lane 3, MDCK cells treated with mRNA encoding the F8R 17-18x.2 meganuclease; lane 4, MDCK cells treated with mRNA encoding the F8R 17-18L1.35 meganuclease; lane 5, MDCK cells treated with mRNA encoding the F8R 17-18L2.23 meganuclease.

2. Results

Genomic DNAs from MDCK cells treated with GFP and MDCK cells treated with F8R 17-18L1.35 and F8R 17-18L2.23 nucleases, respectively, were analyzed by inverse digital PCR. Only the U1/D1 fragment was amplified from genomic DNA isolated from GFP-treated MDCK cells (FIG. 13A, lane 1), while the U3/U1 PCR did not generate a signal (FIG. 13B, lane 1). Using genomic DNA from F8R nuclease-treated MDCK cells, both U1/D1 and U3/U1 amplicons were detected (FIG. 13A, lanes 4 and 5, FIG. 13B, lanes 4 and 5). The U1/D1 fragment was still amplified from genomic DNA from F8R nuclease-treated MDCK cells because the nuclease treatment generated a mixed population of cells with both edited and unedited genomes. Since digital PCR allows parallel analysis of hundreds to thousands of chromosome equivalents, the Factor VIII gene inversion efficiency could be calculated. Out of the total number of Factor VIII genes detected by this assay, 2.8 to 4.5% showed an inversion as a result of the activity of nucleases F8R 17-18L1.35 and F8R17-18 L2.23, respectively.

3. Conclusions

The optimized F8R meganucleases F8R17-18 L1.35 and F8R17-18 L2.23 were also capable of inducing an inversion of the wild-type Factor VIII gene in MDCK cells in vitro, and this inversion could be detected by digital PCR.

Example 6

Whole-Blood Clotting Time in a Nuclease-Treated Hemophilic Dog

1. Methods

This study demonstrated that nucleases encompassed by this invention can be administered in vivo and lead to a significant reduction in whole-blood clotting time in a large animal model of hemophilia A.

A dog from the Chapel Hill colony of Factor VIII-deficient dogs was selected for use in this study. Dogs in this colony are hemophilic and carry the int22 inversion of exons 1-22 in their Factor VIII gene. In this study, a 24.1 kg dog was infused with a single dose of 2.4E14 AAV8 particles (1E13 viral genomes/kg) encoding the F8R17-18L1.35 meganuclease under the control of a liver-specific promoter.

Whole-blood clotting time (WBCT) was determined repeatedly after over a period of approximately 2.5 months (110 days) following AAV infusion. The WBCT assay uses two siliconized glass tubes (Vacutainer, Becton-Dickinson, Rutherford, NJ) in a 28° C. water bath. One mL of whole blood was drawn from the study animal and 0.5 mL blood was distributed into each dry tube. After one minute, one tube was tilted every 30 seconds, the other left undisturbed. When a clot formed in the tilted tube, the second tube was then tilted every 30 seconds until a clot formed. The time for formation of a fully gelled clot in the second tube was recorded as the WBCT.

2. Results

Figure 14:
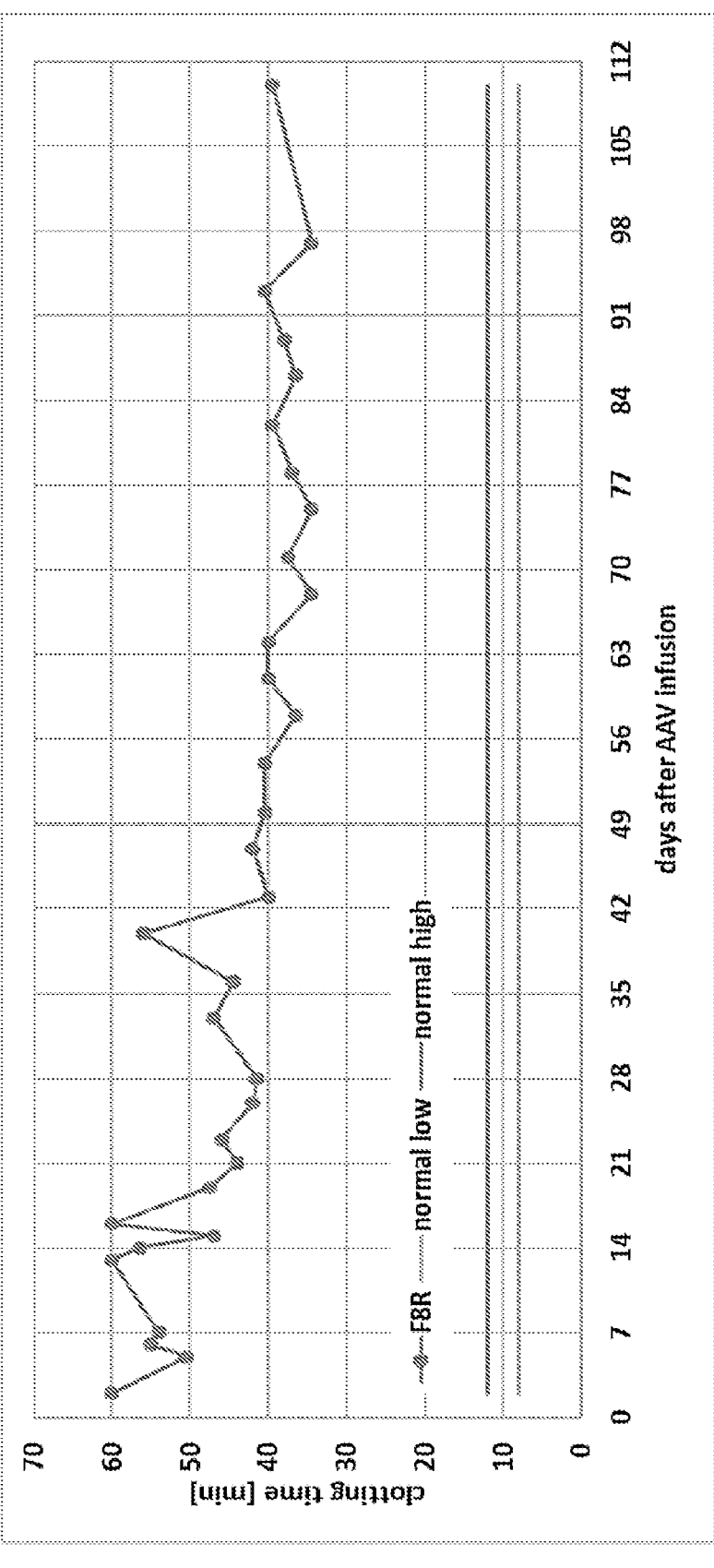
FIG. 14. Whole blood clotting time in a nuclease-treated hemophilic dog. A dog carrying the int22 Factor VIII inversion was infused with a single dose of 2.4E14 AAV8 particles (1E13 viral genomes/kg) encoding the F8R17-18L1.35 meganuclease under the control of a liver-specific promoter. Whole-blood clotting time (WBCT) was determined repeatedly after over a period of approximately 2.5 months (110 days) following AAV infusion.

Untreated dogs from the Chapel Hill colony of Factor VIII-deficient dogs synthesize a truncated Factor VIII transcript and consequently fail to express functional Factor VIII protein. Consequently, their baseline clotting time is at or above 60 minutes (see, FIG. 14), whereas the WBCT of a normal dog is between 8 to 12 minutes (grey lines). However, following a single administration of AAV encoding the F8R 17-18L1.35 meganuclease under the control of a liver-specific promoter, a significant reduction in WBCT was observed within 21 days (~45 minutes), and was further reduced to as low as 35 minutes during the course of the study. A relatively stable clotting time between 35 and 40 minutes was maintained through day 112.

3. Conclusions

A functional Factor VIII protein can only be synthesized from a correctly spliced transcript containing all 26 exons. The shortened WBCT observed in this dog after AAV infusion provides in vivo proof-of-concept for nuclease-induced Factor VIII gene reversion to a wild-type orientation in a large animal model of hemophilia A.

Example 7

Detection of Corrected Factor VIII mRNA by Digital PCR in Liver Biopsy

1. Methods

A liver biopsy was obtained from the hemophilic dog treated in Example 6. The biopsy sample was collected approximately four months (117 days) after AAV administration of the nuclease. Total RNA was isolated using TRIzol reagent (ThermoFisher, Waltham, MA) following the manufacturer's instructions. Total RNA isolated from a liver biopsy from the same dog prior to AAV infusion served as a control. RNA was analyzed by reverse transcription digital PCR (RT-dPCR; Bio-Rad, Hercules, CA) using the following primers and probes. Full-length Factor VIII transcripts can be detected using primers K9F8e22F (which binds in exon 22) and K9F8e23R (which binds in exon 23) and probe K9F8e22-23FAM (which overlaps the exon 22-23 junction).

```
K9F8e22F
                                        (SEQ ID NO: 47)
[5'-TCTGGATGGCAACAAGT-3']

K9F8e22-23FAM
[5'-56-FAM/TGCCAAAGA(SEQ ID NO: 48)/ZEN/
AGACCATTAAGGTCCC(SEQ ID NO: 49)/3IABkFQ-3']

K9F8e23R
                                        (SEQ ID NO: 50)
[5'-TGATCCCAGATGAATCCAC-3']
```

2. Results

Figure 15:
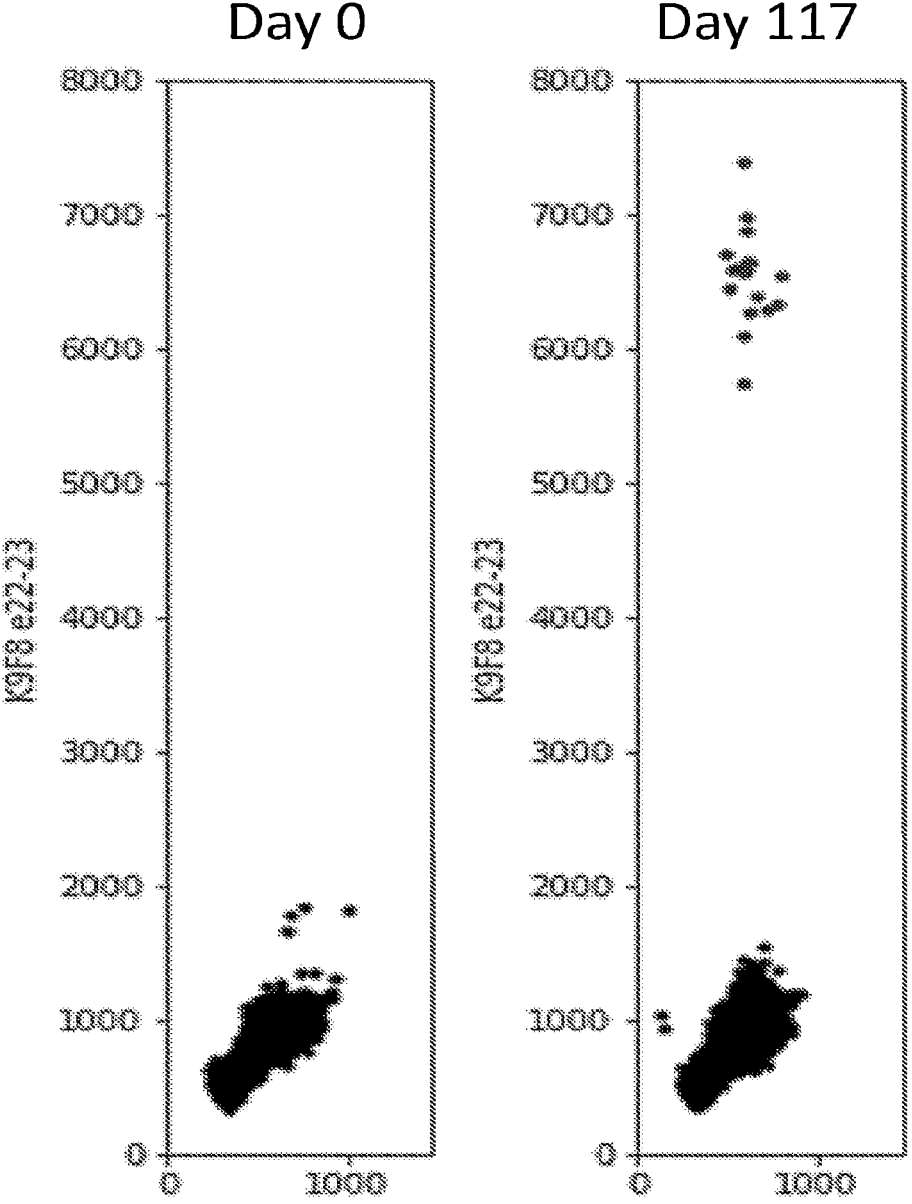
FIG. 15. Detection of corrected Factor VIII mRNA by digital PCR in liver biopsy. A liver biopsy was obtained from the hemophilic dog approximately four months (117 days) after AAV administration of the nuclease. Total RNA was isolated from the biopsy sample and from a liver biopsy sample from the same dog collected prior to AAV infusion. RNA was analyzed by reverse transcription digital PCR to try and detect full-length corrected Factor VIII transcripts.

Total RNA isolated from liver biopsies taken prior to the study and on day 117 after AAV infusion were analyzed by RT-dPCR using K9F8e22F, K9F8e22-23FAM and K9F8e23R. In RNA purified from the pre-treatment biopsy (Day 0), the assay failed to detect the exon 22-23 junction which is indicative of the presence of correctly spliced Factor VIII transcripts (FIG. 15, left panel). In contrast, RNA purified from the post-treatment biopsy (Day 117) contained the correctly spliced Factor VIII transcripts and was detected by the assay (FIG. 15, right panel).

3. Conclusions

In this study, RT-dPCR detected correctly spliced Factor VIII transcripts in RNA isolated from a liver biopsy taken from a hemophilic dog treated with the F8R17-18L1.35 meganuclease. Prior to treatment, this transcript is absent due to the hemophilia A-specific Factor VIII gene inversion. In these dogs, two messenger RNAs containing Factor VIII exons 1-22 and 23-26, respectively, are transcribed in opposite directions from two different promoters on the X-chromosome and cannot be spliced into a transcript encoding functional Factor VIII protein. Only after Factor VIII gene reversion can an mRNA be synthesized that is spliced into a transcript containing all 26 exons, thereby leading to the synthesis of full-length, functional Factor VIII.

The presence of correctly spliced Factor VIII transcripts observed in this study provides further proof-of-concept for nuclease-induced Factor VIII gene reversion in a large animal model of hemophilia A.

---

The invention claimed is:

1. An engineered meganuclease that recognizes and cleaves a recognition sequence positioned within an int22h-1 sequence of said Factor VIII gene, wherein said engineered meganuclease comprises the amino acid sequence of SEQ ID NO: 13.

2. A polynucleotide comprising a nucleic acid sequence encoding said engineered meganuclease of claim 1.

3. A recombinant DNA construct comprising a nucleic acid sequence encoding said engineered meganuclease of claim 1.

4. A viral vector comprising a nucleic acid sequence encoding said engineered meganuclease of claim 1.

5. A pharmaceutical composition for treatment of a subject having hemophilia A characterized by an inversion of exons 1-22 in a Factor VIII gene, said pharmaceutical composition comprising a pharmaceutically acceptable carrier and an effective amount of:

(a) a nucleic acid encoding an engineered meganuclease, wherein said engineered meganuclease is expressed in a target cell in vivo; or (b) an engineered meganuclease protein;

wherein said engineered nuclease has specificity for a first recognition sequence positioned within an int22h-1 sequence of said Factor VIII gene;

wherein said first recognition sequence does not comprise a CpG site;

and wherein said first recognition sequence is at least 95% identical between the human genome and in the canine genome, wherein said engineered meganuclease is said engineered meganuclease of claim 1.

6. A method for treating a subject having hemophilia A characterized by an inversion of exons 1-22 of the Factor VIII gene, said method comprising administering to said subject said pharmaceutical composition of claim 5.

7. A method for genetically modifying the Factor VIII gene in the genome of a mammalian cell, wherein said mammalian cell comprises an inversion of exons 1-22 in the Factor VIII gene compared to a wild-type Factor VIII gene, said method comprising introducing into said mammalian cell:

(a) an engineered meganuclease having specificity for a first recognition sequence positioned within an int22h-1 sequence of said Factor VIII gene; or (b) a nucleic acid encoding said engineered meganuclease, wherein said engineered nuclease is expressed in said mammalian cell;

wherein said engineered meganuclease cleaves said first recognition sequence and causes a reversion of exons 1-22 to a wild-type orientation in said genetically modified mammalian cell;

and wherein said recognition sequence does not comprise a CpG site and is at least 95% identical between the human genome and the canine genome, wherein said engineered meganuclease is said engineered meganuclease of claim 1.

8. The method of claim 7, wherein said int22h-1 sequence comprises a nucleotide sequence having at least 95% sequence identity to SEQ ID NO: 3 or SEQ ID NO: 4.

9. The method of claim 7 or claim 8, wherein said first recognition sequence is within an F8A1 coding sequence of said Factor VIII gene.

10. The method of claim 9, wherein said F8A1 coding sequence comprises a nucleotide sequence having at least 95% sequence identity to SEQ ID NO: 5 or SEQ ID NO: 6.

11. The method of claim 7, wherein said nucleic acid is an mRNA.

12. The method of claim 11, wherein said mRNA is encapsulated in a lipid nanoparticle.

13. The method of claim 7, wherein said nucleic acid is introduced using a viral vector comprising said nucleic acid.

14. The method of claim 13, wherein said viral vector is a recombinant AAV vector.

15. The method of claim 7, wherein said mammalian cell can express Factor VIII following reversion of exons 1-22 to a wild-type orientation.

16. The method of claim 15, wherein said mammalian cell is a hepatic cell.

17. The method of claim 16, wherein said mammalian cell is a hepatic sinusoidal endothelial cell.

18. A genetically-modified cell made by the method of claim 7.

* * * * *

SEQUENCE LISTING

```
Sequence total quantity: 50
SEQ ID NO: 1              moltype = AA   length = 163
FEATURE                   Location/Qualifiers
source                    1..163
                          mol_type = protein
                          organism = Chlamydomonas reinhardtii
SEQUENCE: 1
MNTKYNKEFL LYLAGFVDGD GSIIAQIKPN QSYKFKHQLS LAFQVTQKTQ RRWFLDKLVD  60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                    163

SEQ ID NO: 2              moltype = AA   length = 9
FEATURE                   Location/Qualifiers
source                    1..9
                          mol_type = protein
                          organism = Chlamydomonas reinhardtii
SEQUENCE: 2
LAGLIDADG                                                          9

SEQ ID NO: 3              moltype = DNA   length = 9512
FEATURE                   Location/Qualifiers
source                    1..9512
                          mol_type = genomic DNA
                          organism = Homo sapiens
SEQUENCE: 3
ttgaacagtc actgagcaac tactatgtcc tgggttctaa ttcaggggtg ggcaaactat  60
agccccagaa tttggcccat agcctgcttt tgtacggact gtgagttaag aatagttttt  120
acacgttgaa aggattgcaa agacaaacat acaaagaaac aaagaagact gtgcaacaga  180
gaccacctgt ggtctgtaaa gactaacaca tttctatccc gcccttgaca gaaagagtct  240
gtgggctgct ggtctcctct aacggtggta gagatgcctg cacggttaac attaatcctt  300
ggcaccagaa tcctcagcac ctaggaacca gatcttgcct aacacgctaa tttcagtctt  360
gaccaccttc ctccggcgta gcggttctca aacgtctttg tctttgtact attcacgtat  420
aaaatattct ttcataagca acatttatcc ttttgggaat acctcacaat ggggagaagg  480
ggaaccccaa cagcctttaa gggttcactg cttcgctgcc accatttccg acggtttaca  540
ctgtttttaag tgtgaatttg gaattgtttt caagttaaaa agcaaactaa tcatgtcctc  600
tgaaagtatt tgcttttggc atgctagaaa tcagtgttga cttttgatac tgatgtgata  660
cattacgagg gaattctcaa aactgctgaa atctggcctc ggcccagtta tcactgctct  720
taagcttctg agggagatac atgaatgagc ccacggcaaa tggaaaacga ggagttttag  780
tgtttcctag aattatgctc agatacccac tacctgaccg tctggttatc cttcccctca  840
cctccctgac gcaaggagtt tggaccagag gcctaaggag gcttctcctg aagcccaaat  900
cccaaactgg tcaccagtca tgctccgtaa ctcctgaacc tgacaagaag ccagccggcc  960
aggtctgcag cccgggttaa gaggagcata ccaggaaaga gccaaagagc aaaggagcat  1020
gagcccttca accgctttta caataatttg ggctaggcgt tcagggctcc gtaggaccct  1080
tcctggcagc caagtgagag aaagaggaat gatggtggaa tgggcctctc ctgtgcttcc  1140
cattacttcc acactgtcga aatagaaata gaagcagaaa agaacaccct acaagtccca  1200
cccatttgga ggcactcaac tcacagtgac aaccctccac acctctcccc tgcaaaaaga  1260
cgcaaaacaa aaacacctac tccaaactgt gtccttacat ctcagccccg aagatcagga  1320
ttgtgtgcaa cttcggccca aaggatgcat ttccccaggt tgaaagttt gagaaagagg  1380
ctatattctg aagagttctt gttgtcacca tcaaaaggat taaaaagacg caataaataa  1440
gaaaacagcg tagttggggg gcatgctcca tttgagccag aaagccttgg aaacttaagt  1500
```

-continued

```
gttctcaaac ggaacgccat cctgctttgg gggaacacgg aggctgcctt gcagtcacgt 1560
gatcgcacaa caccaaaggg ccacgcactc tgatttcacc tacttaacta aaagttgcag 1620
caaaatccct attacaggcc aggcgtggtg gctcatgcct gtaatcccag cactttggga 1680
ggccgaggag ggtggatcat ttgaggtcag gagttggaga ccagcttggc caacatggtg 1740
agaccccatc tctattaaaa atacaaaaat tagcccagcg tggtggtgca cgcctgtaat 1800
cccaggcacc ctggaggttg aggtaggaga atcgcttgaa cccaggaggc ggaggttgca 1860
gtgagccgag atcacgccac tgcgctcctg cctgggcgac agagtgagac tccatctcgg 1920
ggaaaaaaaa aaaaaaaaa aaaaaatcc ctattacaaa taaaagctgt tgtgatccag 1980
actgcatata cctctgcgaa tggaaccaga accgtgaatt ccaatgcaaa tcgatgcatc 2040
ggcaccagac ccgctgcact ggatgtatct gcattgcagt cacccgagta cggagcacat 2100
catagatgat ctctgcaggt tcgttgccca cataggaggc atagcgcaaa tttcaaagga 2160
acgaatacat cctggagccc aaacagctat ctggttctgc tgctggcctc ctgacaagta 2220
ggtaagagag tcacatttta tagacgacgg acaccaaaac cacacatgag gagtacaaga 2280
gtagctttat catggattta gggctgtggt tacaaggaag ctgtaaggaa taaaatgact 2340
cccatgaaga cgtaccgtgc ggacgagtgg aaggagaaat ttggccatta caaagacaca 2400
ggaatatgtt aagaagtgag gggcaggatg aaatcatcta gggtaggtat ttagagggag 2460
ggcgccgtgc aaaataaaat cctcactatg aaacaaaggc ggaggcagga ggctgcgtta 2520
ggtggaagca gcggaggaag gagacgaaag ggattgtcat tttcatgtcg tggcttttta 2580
gaagacagcc atgtcctcta ctctgattct atcaaaatgt gttctcgggg tgctggtaac 2640
gttcagccaa cgaaataatt cctatggcgg cagtaggaat aacaaaacgc agaagcggga 2700
acgatgtctt tttattcctc cccagacgca aacgtggatg catgaggttt ggtaacaggc 2760
aaagtcatct ggttaacgtg actgatgcaa aaagtccagg cctgggcaaa aagaagtcac 2820
tgggtgaatg ggatggatca gactccctgt cctgagggg agatggtttc ttgcagaacg 2880
aggtgaagga ggtggttctg ctcagcagtc aacagtggcc acatctccac ctgcagcgac 2940
ttgatggctt ccgtgtcctt ttcgtgggta gccatgacca aagactggag cagcagaaag 3000
agctcctcgg gaagctggcc gctgctctcc tgcccgtgac tgtcaaaagc ctcccagcag 3060
tacttctcca gggtctgggc gtgctccggc agcagcttgg cgggcggtgg ttgcaggagg 3120
agcagcagca gcacgcggga cacctcgcag cggaccagca cgtccgagaa ggcgcccagg 3180
gcggcggag agggcgccgc cgagccgag ttcggaggaa gcagcgcggc cggtagggcg 3240
ggcgtcgccc cgggcccggg ctggggtgcc ggcggcggag gcggcggcag tgactgcacc 3300
gggtggctgc cgtgctcccg cgccaggcgc tgcatgcgcg tgaagaccgc cagggcgccg 3360
gtgtagtcgc gcgccagcag ctggcaggag gcggcctcgc caagcgcctg cagcgcggcc 3420
aggggcagct ggggcagctg gagctgggcg gcgcgctgga agtgaccggc ggcggcggcc 3480
ggctggccca ggtcgcgcag ggcggcggcc agctcgaggc agagggcggc ggcggcggcc 3540
ggctggccca gctcgaggtg cagacgcacc gcggcgccca gggcgctggc ggcggcctgc 3600
agcggctccc cgtaggcggc ggggcagacc aggcgctggc gcgcgtcgcg ctcctgccgc 3660
aggaagaggc gggcggcctc ggtgagggcc agcgcctccc cgggcccgtg gaagagcgcc 3720
tgctggcagc gcgccaccgc cagctggcac caggccgcgt agggcagaca ctcctgggcg 3780
cgcagctccc ggcccagctg tccgaactgc tcgccggcct ccgccacgtt cggcttccgc 3840
aggaaccgct tcttcagctt gttcgatacc agccggtagc gggccaggaa gtccccggcc 3900
tcgggtcccg ggccggcgcc gccgccgccc aggcctgcag ccgctgccgc catgctcgcc 3960
gccccaagca cttcccgacg cgccgccgca gctggcgggc gggccggggc ggggcgacgt 4020
gccctgcgtc ccctcggcg ggctgccgcc gtgcccgcc gcccgagcct 4080
gcccccttgcc ctgatgaggt gcaaagagcg ggatcggagg cggggcctgg ccgggctgtg 4140
agcggcgtat gcaaatcgag ggtctcgggg atgcggatcc aagaccctgg gaaggtacgc 4200
ggggcctggc ggggcaccag ctgctgctag ctcggctgca atgcaagtgg tctaggttgc 4260
taaagcatc ccacagcctc tccatctgaa catgacccaa acgaaactcg tgaccctaat 4320
tccatgtctg cgcatttcta gactgttgtc ccccccccc cccgcccga ctactcagtc 4380
ctccgtcttc cggtccaggg ccccttgcca agcaccgggt ccacctctcc gtccccaccc 4440
cggttgcctt agaagtccgt cctgtcgcaa cactgcagtc atggtcttga ggcccacccg 4500
ccccaacgaa caccatcatg ctgaggactt tcccgggcag gcctgactt gctcagaacc 4560
agcggggggtg tccccttccc acccaggggc actccctgc actgtcaccc ggagagactg 4620
ctcctctgtg ccatccctgg ctcccaccca accccagacc cccaccacct ctccatccct 4680
ccagctgtg aggtctcaca acccccaac ccatctcacc gcccccccac ccccacccca 4740
aggcaaagtg actgaagcgg gcagatggct tccttgaaac attttattga cagaattaat 4800
gaaggcccaa gactttgggg cctgggttgt gggggagggg tgtttaaggc cggggggttca 4860
ggccggggga tttggggccg ggtgggtgga cgagtggacc tgtcaggtcc caggggccgg 4920
gtgtcagaag ctagtcctcg ccaggggcca cttgagagat ggtggtcgtg ttgaaaaggg 4980
tgctcagtag cctgtcgttg tgaaccacca tgtccagcag caggggagtg atgttccgct 5040
ctccgctgtt ctgggcctcg ttgcccgcca gctccggcac cttggccgtc aggtactcaa 5100
taaccgcagc gaggtagacc ggcgccgtgc gactcaggcg ctgagcgtag tggccctccc 5160
gtagactgcg ctccacctgg ctcactgaaa acgaaagctc cgctcggacg gtgcgagagc 5220
aggtccgccc ccggccgcca gcaccggagg accctcggcg tctcctcctc ctcggcatgc 5280
tgggcgttga gtgtgctatc tcggcttggc ccagctaggc aagatggctc tcaagaggac 5340
agttaccgcg tccagtactg tgtatcctag cgaccagggc ccagcccctc attggctagg 5400
gagccgagac caatgggcac gcacatccgg cgacgggcac gcatgtggtg acggcccctc 5460
acaagggaca cacgtccgtc aggtgacctc atcactttcc cattggcctc gagggagcag 5520
gcctgggcct agaagtggct ggagggccgt ggggtgggg tgggcggggg caggggggaat 5580
cgcgctggtg accctctctt tgccagtggg aactttccct ttctactgga tgggaacacc 5640
gtgggaaaga caaaggggtg ggcgagggga ggacgggtac cacgccttca caatgttgca 5700
catccatcac gaccacctag ttccaaaacg ttttcaacac cccgaaaaga aaccgaaacc 5760
cctgtaccta taagcagtca cttgccgcac gcctccttcc acaccaccac taccagcccc 5820
cacacccctcc cacacacacc ccctgccccc gcccatacac acgttcccga tagtccctga 5880
caacccctag tccatctgct ttctgtccat agaggttagc ctgttctgga gatttcctat 5940
agatggaatt atacgaccaa atgtgaggcc gtgtgtgtct ggctgctttc acttagcgta 6000
atggtttcat cagggtgcat ccatgtgagg gcatgaatca ctacttcctt cctttgaatg 6060
actgagtacg attctgttgt atgaatagga ggccacattt tgtttaccca ctcgtcagtt 6120
gatggacagg ttatttcccc cttctggcta ttgtgagtgg cactgccatg accatctctc 6180
tacaggtttt tctttgaata tctcttttca gttcttttgg gtctatttct agcagtcaaa 6240
```

-continued

```
ctgctggctc gtgtggtaat tctgtttaac ttattgagga accaccaaac tgatttccac   6300
agcagctgta atctttcgca ttcccaacag tagtgcatga gagtcccaat ttcttcacag   6360
cctcatcaaa acctgttttc tgtttgcctc attttgtttt gtttacagta gccatcctac   6420
tgggtgtcaa gtgctatctc atggtggttt tcattcgtat ttcccaaatg gctaatgatg   6480
ttgctgtggt ttgagtgcat cccccaaatt gtgtgtcttg gaaacttaat ccccaaattc   6540
acatgttgat tggaggcgca gcctctgaga cggtaattag gattagataa ggtcatcggg   6600
gtgagacccc caggatgcga ctggtggctt tataagaata ggaagagagg cctgaaacga   6660
catacacgct cttgccctct cgccgtgtga taccctctgc cgtccccaga tgccgggtca   6720
cttcccagtc cccagaacgg taagaaataa atttcttttc tttataaatt gttcagtgtc   6780
gggtattcaa ttatggcaac agaaaacaga ctaagacatc ttttcatgtg cttcttggcc   6840
ctctgtacct ctgctttgga ggaatgtcta ttcaagccct ttgcccattt tttaattcgg   6900
ttgattgtat tttggctgtg ggcttctaaa acttattcat atattctgga aaatagactc   6960
ttatcagata tgtgacttgc aaatgtttct cccattcact ttctggatag agcccttgt    7020
tgcccaaaag atttacattt ggatgtagtc caacttgcca aatgaaaaga tatctgtggc   7080
tttgcctttg gtgtcatact gaaggagctg ttgcctaatc caaggtcgtg caaagttaca   7140
tctccgtttt cttcttagag tttttatagtt tcagcccttta catttagatc tgtgatccat   7200
tttgaattaa ttctttacat gatgtgaggt aggggtccag gggccttctt ttgcatgtgg   7260
ctatccagtt gtcccagcgc agtttgttga ggggattatt cttcccctcc acccattgag   7320
gggtgccgga actcttactg aaaataaact ttacataaat atatgggttt attcctgact   7380
ctgagttctg taacattgac ctaatgtatc gatcacgatg gcagtaccac cctttttcgga   7440
ttactgcggt tttgtagtac gttttgaaat tgggaagtgt gagtccttca actttttct    7500
tttctgagat tgtttttggct atctgagccc cttacatttt cttatgaatt ttaggatcag   7560
cttgtcagtt tttacaaaga aggcaggttg gattctgaca ggcatcacga tgaatcgtta   7620
tattgccttg gagattatgg gcatcttaac aatattaagt gtcccaatcc gttaacacaa   7680
aatgcctttc gatttattta ggtcttcttt aatttatttt agcaacgtct tgaaattttc   7740
agagtataca tcttgtacac ctttagttaa atttattcct cgacatttta ttgtttcgat   7800
gctactgtaa aatgaatcat ttccttaatc ttattttcat gttattcatt gctaggtgt    7860
agaaatacaa ccgactgttg cagattgatc ttggatactg caactttgct gagccgaata   7920
tgctttgctg agcatactca gacagggttg gcatattagt ccgttcctac actgctataa   7980
agaactgcct gagaatgggt aattcctaaa gaaaagatgt ttaattgcct catggttctg   8040
caggctgtac aaggcttctg cttctgggca ggcctcagga aacgtgcaat catggcggaa   8100
ggcgaagggg aagcaagcac cttcttcaca tgttggagca ggaggaagag agagagaacg   8160
cacgcaaagg gggaagcgct gcacattttc aaacaatcat cagatcttgt gagcgctcta   8220
tcagaagaat agcaagggggg aagtccgccc ccatgattca atcacctccc actaggccct   8280
tccttcaaca ggtggggatt acaattcgac atgagatttg ggtgggggaca cagagccaaa   8340
ccgtctcagt ttttttttt ttcttttgtt ggactcttta gtgtcctcta tataagaaca   8400
tgccatctat gcatctatga atagagatgg ttttacttgt tcctttccga tctggatgcc   8460
ttttatttct ttttcttgac taattgccct gactagaact ttgagtacga tgttgagtta   8520
caagtggcat tcctgatctt agggggaaat caaccagtct ttcaccatta agtatgatat   8580
tatctctggg tttttcatgg atgccctcta tcaggttgaa gaagtttctt tctgttcctg   8640
gtttgttgaa tttatttttca tgaaagggta ctgcgttttg tcaaatgatc cttttttgtac   8700
atgattaaga tgaccatgag ccccctcccc cgccccgct ccgccatgca ttctgttaat   8760
atggtgtatt atataaattg atttttcacat gttgaaccaa ccttacattt gtgggataaa   8820
tcctatttgg tcatagtgta taaagagtgg tcaataaaca tttcgttgaa agaataggag   8880
tggatctggc aagcttcttg gaggacaatg tgtgtgttaa agaatctgta gcatgatgag   8940
aagccaaggc accggtggga ggagggggagt tgcaaccaat tcattaaggc tggagagtac   9000
gatgccagtg gagcagtagt ggttgatgtg gctgggaaag aggtaggcag gagccaagac   9060
atggaggttc tattatgcca tgctcaggtt ttagaatacc ctgtaggcta cactgaaccc   9120
actgtggtct ttcagcttgg gagtgacgtg gtctgatttg cctctagaaa tatcaccctg   9180
gaagctgtgt ggagaataga acagagagga ttgtgtgtgg agaatagaac agagaggact   9240
gagattggaa ttagaaagct gctgtattat accagtcaag aaatgacaga tatctcaact   9300
aagacaatgg cattggtaga taagactagg ggacagagtc cataaaaagt ttaggtagta   9360
aaatggcaca cagtagacac tcactacata ttactcatac tggcgaacct agctggagac   9420
atgataattc atgtgctcat tcttcaaaaa atattgaagg gtagtgccag gtatactgtg   9480
ttaagcattg agacaacacc aacgagaaat at                                 9512
```

```
SEQ ID NO: 4            moltype = DNA   length = 13008
FEATURE                 Location/Qualifiers
source                  1..13008
                        mol_type = genomic DNA
                        organism = Canis lupus
                        sub_species = familiaris
SEQUENCE: 4
aagatttat ttttatttat ttgaaagaga gcatgagggg atccctgggt ggctcagcgg    60
tttagcgcct gcctttggcc cagggcgtga tcctggagac ccgggatcga gtcccacatc   120
aggctccttg catggagctt gcttctccct ctgcctgtgt ctccacctct ctctgtgtgt   180
ttctcatgaa taaataaata aattttcaaa agagagagag agcatgagta agagggagag   240
ggagagatag agaatctaaa gcagactctg tgctgagcag gaacccaaca cagggctcaa   300
tcccacgacc ctgagatcgt gacctgagcc aaaaacagga gtcagatgct taaccaactg   360
agccacccag gcgcccctgg agttgttttc taactcatta atttctgttc aaaactttaa   420
aattttcttt tactttcttt cggtttttgtc tttcctaaaa catggagttg aatgactagt   480
tcatttattt tcagtctttc tcattcagta tgataaaaga gttaactact ctcatgaagg   540
tcattcattt aataaacagt tactgagtaa ctgctatgtt ctagattcta gtacagagat   600
ggggaagcta gagcccatcc ttgaatttgg actaccactt gcttttgtac ggactgtgac   660
ttaagaatgg ttttttacagg tttaaagttg caaaaacaaa cattatgcaa cgaagatcat   720
ttgtggcctaa aaaagactaa aatattgcca tctggtcctt tacagaaagt ttgcagactg   780
ctggtctggc ctaaaggcag tagagatgcc taggcagtgc catgaagcag gactcttcat   840
ccccacagct tgcctaatgt gcagatttca atcttagtca tcgtccccca gtgtagtgat   900
tctcagatgt ttttatatct ttgttttgct cacagacaaa atcttgttca tcagagatat   960
```

-continued

```
ttcttatcat ggatgtccca cataaagagg gagaggggaa cctttaagga ccacagctac   1020
actgccaccg ttctcaatag tgtagaataa tgtaaatgtt aacttttta tttttttaag   1080
atttatttat tcacgaaaga cacagagaga gaggcacaga cagaggcaga gggagaagca   1140
ggctccatgc agggagcccg acatgggact ccatcctggg gccccagcat cacgccctgg   1200
actaaaggcg gcgctaaacc gctgagccac ctgggctgcc ctaacttttt tatttttaa   1260
aagattttac ttatttatcc atgagagaca cagagaggca gagacacagg cagagggagg   1320
agcaggcttc atgcagtgag cccgatgcgg gactcgatcc caggacccca ggatcatgac   1380
ctgagccaaa ggcagatgct cagccactga gccacccagg tgccctgta tatgttaact   1440
ttgatatatc aatgaacatt tcagtgatgt ggctttttct ctctggtttt caagttaaaa   1500
agaagagtat ttttaatgtc ctttaaaaat atttattttt ggttgtgtta gaaatcagtg   1560
ttattttgac ataaagttga taattaccaa gggatttgtc aaagcctatg aaaattgcag   1620
aaatctagcc ttagcccagc tatctatgct ttgaagtttc tgaggagag ctataaagga   1680
gccaatgaca aatggaaaac aactttcatg ttttctaaaa ttatacttgt atacccaaca   1740
ccaggctctc tggcaaaccc tcccctctac atcctcaatg caaggagtta gaccagaggt   1800
ccaagggtgc ttttccttaa gcccaaaccc aaatactgcc accagtcaca tatcaaaact   1860
cctatacatt gttgttgtag tgatgtgatt tgaagtgagg tttgggagcc aatggcgaag   1920
aattcttgag acttttttcag tgcaaaaaat gctgttttaa ttacagcaca gggacaggac   1980
ccatgggcag aaagacctgc actggggttg cgaggagtgg ctgattatgt aagattttcc   2040
atcctatgga ggggagggtg atgttaaggt cccaggaaat tgagtatagg gttcgggagg   2100
tctggctatt gatgattgct ttttttcctt gtaaatcatt aagacagttg caaactgatg   2160
gaagattcat gtcgtgcatg actgtgatct ctgtcagtta agcatttgtt tttccccttc   2220
ctttgctctt gggcagccag gagtgcctgc acaacatcac accttcccca cctggtgggt   2280
ggggtgggag gggggcagtt gttgcggagt attagcgtgt gctttacccct cagcttgcct   2340
tttgctccct catcaataag actactggcc agactgaggg gggcacttga cgggatgagc   2400
actgggtgtt actctagatg ttggcaaatt gaacaccaat aaaaaataaa tgtataaaaa   2460
aaaaaaagac tactggccag gcctgtagcc cgggttgaga gtataccaag aaaagtaaaa   2520
ctgcaaagga ccatgcaccc taaccacttt tttaaaaaat gttttttcaaa aattccagta   2580
taattaatgt agtgttacat tagtttcagg tgtacaacat ggtgactcaa cacctctata   2640
catttcccag ggctcatgat gattacgtgc actcttaatc cccatcatgt atttcaccca   2700
tccccacacc tacacccat ctggtgacca tcagtttctg gtctatattt aggagtctgg   2760
tttttttatc tcttttttttt cttttcatctt ttgtttctta aattccacag gagtgaaatc   2820
atacagtatt tgtctttctc tgacttattt cacataacat tatacattct agatccatcc   2880
atgttgcaaa tggcaagatt gaattctttt tcagggctca aaaatactcc attttggatc   2940
tgtgtgtgtg tgtgtgtgtg tgtgtgtgtg tgtgtgtgtg tcttgatcct ttcatctatg   3000
gacacttgga ttgcttccat atattgactg ttgtaaataa tgctgctgta aacatagggg   3060
tgtgtatctt tcttcgaatt agtgttctca tttttcgttgg gtaaatacccc agttggggaa   3120
ttacatggtc atatggtggt tctattttta attttttaaag gaacctccat actatttttcc   3180
acagtggccg caacagctgg cattcacacc aatagtgcat gaaggctcct ttttctccac   3240
atcctcacca acacctgtgc tttcctgtgg tttttgatttt agccattctg acagatgtga   3300
tatctcattg tggttttcac ttgcatttcc ctgatgatta gtgatgttga gcatcttttc   3360
atgtgtctga tacccctaaca cttttgcaat aagttagact aggcttttag ggctccgaaa   3420
gacccttcca ggcagccacg tgagtgcgca ggactggtgg cggagtctgt gtcagatggg   3480
cctcttttgt attttcttac ctactgactg cttcccccgtt gctgaaatgg cggcatgagg   3540
actacctaac cgtcccaccc atttacaggc gcttaactca cggtgaccac cgcctcacaca   3600
tcccccaaca cacacacaca ctaaaggcaa aacagaactg cccaaccgca tccttaaacc   3660
tcaccccacc agatcagttc cgtacacagc ctcaggctaa agggtgcatt ttccgaaagc   3720
agaaggactg agagggagat tacattctgg agagttctca ctggccctcc caaacccta   3780
aaggcaagtg gaatgtaaaa acacgcggct agtaacgttt gcacgcgaca tttggaccaa   3840
aaaagccttga aaatgtagga ttctgaaaca ggatgctgtc ctcttgggca agaaaggcgc   3900
ggtctcgcag accgaggacc acgcaatagg tcggaagcac gctgattcaa cacatctgag   3960
ttacctacca gtggcgggaa ggcgcccagg acaagtaagt cccagcgtgg cccaggccca   4020
cgtctgagaa tggaacctag gcccacaacc ctgagttcca aggcacgcca gacacctcga   4080
cagtcgaacg tgggcccctg cttttgcgcag gacacattcg ccttggcgcc gaggaaggcc   4140
cacgcggcca aggttgtctg tggattgact gtgcggcaca gcccgagcag caggcgcacg   4200
gaccgctgcg agtgaacgac cacactgcgg cccgaagcac agccacccgc tcttccccct   4260
gctgcctccc gacaggtgga gcagctattc cgcgttacgg aggaaggcga accgcaggcg   4320
agaggcatca gaacggcttt attgtggatt tagggcagca gccccgaggg cccgtgccat   4380
ctagtgctcc ccaggggtac gcgtggggcg tgggcaacaa aggagaacct gggtgagcac   4440
ctggagagac accggcctgc gctaaagcag atccccgacg aacaaaaaac ggaaccgaga   4500
ggcgtgtgca acatccaacc gtccgacttg caacagaggt gtacgggagg gtgggggtgg   4560
gggtggggggt gggggcccgc aggggagttg ggtgcaagaa gaggcagggg gtaaagggggc   4620
cgctcggtgt cccgtggccc gtcttgggga agagagccaa gtcctccagg ctgacccgt   4680
gatgctgggg tggttgccgc gccagggacg gcacgaagcc tgtgggatgc gggaggctgc   4740
agtcccgcag cgtccggtgg aggcgggcgg gcgaagagca agacaggtgc gagtgcccggg   4800
cccctgcccg tcggtccgtg ggcaccgccg cccgccagcc ggccggccgg ccggccggcc   4860
ggcccgcggt ccaacggcgg ggcagcagca ggccacgggg ccagaggcgg aaagcggctt   4920
cggggctggc gcgcgcgagt ggtcagacgc cctgccccga cggggacacg gcttcctgca   4980
gaacgaggtg cagcaggtgg ttctgctccg cactgagcag cggccacatg tccacctgca   5040
gcgacttgac ggcctccgtg tccttctcgt gggtggccat gaccagggac tggagcagca   5100
ggaacagctc gtcgggaagc tggccggcgc gtcgcggccc gtggccgtcg aaggcctccc   5160
aggagtactt ctccagcgtg tgggcgtgct cgggcagcag cttggcgggc ggcggctgca   5220
gcaggagcag cagcagcacg cgggacacct cgcagcggac cagcacgtcc gagaaggcgc   5280
ccagcgtggc gggcgcgggc gtgggcgtgg gcgcgggcgc ggcaggcagc agggcggcgg   5340
gcaggcccg ggcggccgcg gcgggcccca gcggggcccga gacggacagg gacgaggagg   5400
aggccgacga ggtcgaggcc gaggccgacg aggtcgacgc cgccgccggc ggggccaggg   5460
gcagcggcgg ggcggcgggc ggcggggccg ggggcggctg ccgcagcggg tggctgccgt   5520
gctcccgcgc caggcgctgc atgcgcgtga agacggccag ggcgccgctg tagtcgcgcg   5580
ccagcagctg gcaggaggcg gcgtcgccca gcgcctgcag cgcggccagg ggcagctgcg   5640
gcaggtgcag ctgcgcggcg cgcaggaagt ggccggccgc ggcggccggc tggcccaggt   5700
```

```
cgcgcagggc ggcggccagc tcgaggcaca ggccggcggc ggcggccggc tggcccagct   5760
ccaggtgcag gcgcacggcg gcgcccagcg cgctggcggc ggcctgcagc ggctccccgt   5820
aggccgcggg gcaggcgagg cgctggcggg cgtcgcgctc ctgccgcagg aagaggcgcg   5880
cggcctcggt cagcgccagc gcctccccgg gcccgtggaa cagcgcctgc tggcagcgcg   5940
ccacggccag ctggcaccac gcggcgtacg gcaggcactc ctgcgcgcgc agctcccggc   6000
ccagctgcgc gaactgctcg cccgcctccg ccacgttcgg cttccgcagg aaccgcttac   6060
gcagcttgct cgacacctgc cggtagcggg ccaggaagtc cccggcctcg ggccccgggc   6120
ccgcgccgcc gccgccgccg ccgccgccgc cgcccgggcc gccgccgccg ccgccgcccg   6180
ggccgccgc cgccgccgcc gccatcttgc ccgcacgcgc gcacgcccga cgtgcccgcg   6240
tcccccggcc ccgcccccctg cgggcccgc cccccgcgg accccgcgca tgcgtgcgcc   6300
gcccccgcc gtcccgccgg acggaaccga gcgcgcgggc cggcgcgggg cctgggcggc   6360
cgcggccctt ccgaggcgac cccggccccc gggtcggccc gcgccccccg gccctcccg   6420
gccctgccg gccccgagc taacgtcgcg gcgccggccc gcctggcccc gaggccgctt   6480
ggccggagtc aggatggtcc ccgcccccc agccttccgt caaagccctg tccctcgag   6540
tccgcgccgg cacctgtgtc ccccaacagt ccgcgccggc agctgtgtcc ccccattcac   6600
tccgcgccgg caggtgtgtc cccctccatc ccgcagccag gttgttactg caccggcgtt   6660
caccccatca ccacgccgca ggcatggtcc tgagctccag ccccacacac accatcgtcc   6720
acgggactgg cccgtgcggt ggggggggggt cttctatgcc ccagcgtcac tcccagccca   6780
gccacccct gtcctgaccc cgagcagtcc ccgtccccgc accccagccg gaccccacca   6840
ccacccctgc accccagccg gaccccgcca cagcccccgt ccctgcaccc caacaatgct   6900
ccggaccgca tgaccgaacc ccgcaccaca cccacgaacc cgcgccccac gccacacccc   6960
aaatcctcca tcaccccat cgtgcaccgc cgagggcacc ccaaccccccc gtcatccccg   7020
agccccgcac ccccacccca acctcgccca caacccaaa ccccaacctc ccccccgccc   7080
ccccccgccc tccccccgag gcgcgtcccg cacccagtga gccaggcgca cacgtctggt   7140
tgtctctgcg cctttattg cggggacgcg ggggtcaccg agccccccg gcggctcccc   7200
gggcggcggc gggcatcagg ggccggggc ggctagtacc gggccggggc cacctgggac   7260
acggtggtca tcgtgaacaa gccgctgagc agctcgtggt tgtgcagcgc ccggtccacg   7320
agctccgggg tgatgtacgc ggtgcgcctg tgccgggcct cgtcgcccgc cagccccagc   7380
acggtggccg tcaggaactg gatgacggcc gccaggaaga tggggcgga cgcgcccagg   7440
cgcttggcgt agcggccggc ccgcaggagg cgctccatct ggcacacgga gaaggccagc   7500
cccgcgcggg cgctgcgcga gcggcacgac ctcgggcggc cggcccgccc tccacggctc   7560
cccctgagcc gcgcgcgggg cctcggcggc gctcggcgcg gggcctcggg ctgcggcccg   7620
gctgcggccc ggctggggac gctcgggcgt cgggccgcgg agccacgggc ctcgggctgc   7680
ggagaccccg ggctgcggac gctcgggcgt cgggccgcgcg agccacgggc ctcgggctgc   7740
ggagaccccg ggctgcggac ggtcgggcgt cgggccgcgcg ggacatgggg cttgggctgc   7800
agagacatcg ggctgcggac agagagacac cggcctcggg ctgcggagag acggggcaag   7860
ggctgcagac agacgggcct caggctgcag agagaccgac ctcgggctgc agagagaccg   7920
aactcgggct gcagagtgtc tgacctcggg ctgcagagac cgacctcggg ctgcggagag   7980
acgggcctcg ggctgcagaa agtccgacct cgggctgcga agactgacct caggctgcgg   8040
agagacgggc ctcgcgctgc agagagaccg acctcgggct gtagagagac tgacctcggg   8100
ctgcagagac cgacctcggg ctgcagagag tccgacctcg ggctgcagag agtccgacct   8160
cggggctgcag agagacgggc ctcgggctgc gctgccgaaa cagcgtcggg gcgcagagag   8220
gagcgccagg gtgcaccgcc gtgcggccgg ctgggccgga tgcacccgag ccctcagcag   8280
cggggcgagga ggccccgctc cgtatccgag ggacacaccc cctcccccgcc ccgctgcgca   8340
cgcggtgaca cgcaggcctg atgaggtcac cgcgtcccca ttggcccggc ccggccctcg   8400
cccgccagaa aagccgctgg cgggaagtcg ctggctctgc gccgcgcgga cggcatgggg   8460
cgccaccgac gagcgtgcag gagctcgcgc gcccccacgt gcacccccga catgtcggcc   8520
ctctcggctg cacacgcggc accgccccgc acagacggcc cggccgccgc gcgctcactg   8580
cccccctgcac cccgtcctgc ccccgggggac cgaccgctcc tcggcctcct gtccctgccg   8640
cttggcgtcc gctggacacc tgctgcaggg gccaccctgg gaccagtagg tggccgtgtg   8700
cgccggccgg gttccctcgg caccgtgttc tcaggagggc tgttctctga gggagcggga   8760
accggggtcc ctccccccga gagagcagga atcgggcccc tcccccctgag ggagcaggaa   8820
tcggggcacc ccccccccagg gagcaggaat aacggcctct tccccccccc cagggagcag   8880
gaatcggggc ccctccccctc aagggagcag gagtcgggt ccctcccccc cgagagagca   8940
ggaatcgggc cctcccccct gagggagcag gaatcgggt ccctcctccc gagggagcag   9000
gaatcggggc accccccccc ccagggagca ggaataacgg cctcttcccc ccccccccc   9060
cgggagcagg aatcggggcc cctcccctcg agggagcagg aatccgggac ccccaaggga   9120
gcgggaattg gggtccctcc gcccgaggga gcaaaagacg gacctcgggc tgcagaaaga   9180
cggacctcgg gctgcggaga gaccgacctc gggctgcgga gagaccaacc tcgggctgcg   9240
cttccgaaag acggcgtcgg ggcgcagaga ggagcgcgcagg ggtgcaccgc cgtgcggcgg   9300
gctgggccgg ctgctcccga gctctgagca gcgggcgagg aggccccgct ccgtataaaa   9360
gcgacacccc ctcccctccc cgctgcgcac gcggtgacac gcagatctga tgaggtcacc   9420
gcgtcctcat tggcccggcc ctcgcccgcc agaaaaggcg ggaagtcgct ggctctgcgc   9480
cgcgcggacg gcatggggcg ccaccacga gcgtgcagga gctcgcgcgc ccccacgtgc   9540
acccccgaca tgtcggccct ctcggctgca cacgcggcag cgccccgcac agacggcccg   9600
gccgccgcgc gctcactgcc ccctgcaccc cgtcctgccc ccgggggaccg accgctcctc   9660
ggcctcctgt ccctgccgct tggcgtccgc tggacacctg ctgcagggc cacccctgga   9720
ccagtaggtg gccgtgtgcg ccggccgcgt tccctcggca ccgtgttctc aggagggctg   9780
ttctctgagg gagcgggaac ccggggtccc ccccccagga gcaggaat tggggtccct   9840
ccccccgagc gatcaggaag cggggtccct ccaccaaggg acaggagtcg gggtcctcc   9900
ccccgaggga tcaggaatcg gggtccctcc accaagggat caggagttgg ggtccctccc   9960
ccaagggaca ggagtcaggg tccctccccc aaggacagag agtcggggtc cctccgccaa  10020
gggacaggag tcgggtccg tccccccgag ggagcaggaa taggccccccc gaggcagcgg  10080
ggatcgccct gcacgtccat cgaggggcac tcgcccccac tcgcccccgc ccctggcggc  10140
gaggggcacc tgcgggcgga cgtgcgcggc ggcggcggcg gcgaaggtcg cgcggggccc  10200
ctccgggcgc gggatggggg gcccgacggc agggcgacac ccgctgtctg ggcagcgcgc  10260
tgacccggcc ccctgctccc gccgcgccgc cccactggcc ctggcccgcg cctgctcctc  10320
ccggtgcggc ctcgcgagcc cccgcgccgg ctgtgccgcg gcacctggca cctggggtc  10380
actgtcccccc gtgtgtaggg aggggcaggg cggggcccga gggacaggga gctcgggcag  10440
```

-continued

```
ctgcagcccg ctgacccggg ccccccgtgga gcctgcgggc tcccccccgcg ccccccaggggc   10500
tgccgacccg agcccgggct gcaggcgggc gcccagctga tcccccccgc ccccccccccc   10560
cccgggctgg gcctgtcgcg ccccccgggtc ccgagcgccg ccccgcggtg ccagcagcgg   10620
cgggtcggcg cggcgggagc gctgcaggtg cgccgggacc gggcgggggcc ctccctctgg   10680
gtgcccctcc aggcggcccc tgcactcggg ctgcgcaggg cggggcgggg gagcttcccg   10740
gagggggtgc ggcctgtctg tcgcctgggc gcgactcggc gatgggacac gttcaggtcc   10800
tgacaccggg ggggggggg ggagcggggg ggcttcccgc gtattcgggg cctcccgagt   10860
gactttcagc aatgttccgt gactttccgt gcacacgccc tgcacgtcct ccgctacgtg   10920
tattcctagg gatgtaattg cacgtgatcc cgatttgaat aaaattattc aatcagttag   10980
ttaactgatc aattaatcag tttcgtttga ggtcgtcgc cgctgccgcg tggaaaaccc   11040
cctaatttct gcacgttggt ctcatatcct gaagtttgtt gaattcacta actctgccgg   11100
tgtttcgtga attctttagg acttttttctg tgtaaggtta tgtcatctga gaacacagat   11160
ggttttccctt cttcctttcc aatttaaata ccctttattt ctttctcttg catcattgct   11220
ctagccagga tttccattac aatgtcggtt agaggcaggg aaagcgcgga ttcttgttcc   11280
tgattagggg aaaagcttctc agtcctccac cagtgagtat gaccttagct atgggtattt   11340
cataaatgcc ctttattatg tttggtgatt cccccttctat tcctagtttg ctgagtgttt   11400
tttgtcagga aaaggtggat tttagtcaat gcttttttctg catgaatcaa gacagtcatg   11460
tgggtttttc ccccttttatt ttattaacgt agagttattt tcttaagttg aagcatcttt   11520
gtattcctgg gacagttcct ttttggacat gaaatgtcac ttttataatg tactgctgga   11580
ttccgtctgc taaaatcatt tgaggatttc tgcacctata ttctttttta aagatttttt   11640
aggtactatt tgagagacca tgaatgatca ggggggcggag ggagaggatg aagcagactc   11700
cccactgagc aggggaccctg acgcgggcct cgatctcccg acccgggatc atgacctgag   11760
ctgaaagcgg atgcttcacc gactgagcca ccaggcaccc gggcaaaaca atttcttaca   11820
acattctgca cgatactgta atgctgatgt gtcatcatat aacacacact gattcctatt   11880
ctagtgtatt caagcataca caaagcctag gagatcattt taaactttcc gtagcctgta   11940
cgccatggtt taaaccgagg ccttctgagt aggtgttcct ttttttattta aagattttat   12000
ttatttattc atgagagaca cagagagaga gagagaggca gagacccagg cagagggaga   12060
agcaggctcc atgcagggag cccgacgcgg ggctcgatcc caggtctcca ggttcatgcc   12120
ctgggccgaa ggcaggtgcc aagccactga gcccccccagg gatcccctga ctaggtgttc   12180
ctatcacatt tctcaaactg tgttcccttt cctttgaaga tgccgtgtac tttctctgca   12240
ccctagactg ctcaaggtcc gaaccccccac atgttggatg ttaacacgtg tcttacaaat   12300
ccatacacaa ggaatcatta attaaagcct cacagttcat gcacatgtgc acacacacac   12360
acacacagag agagaccaca gtcttggaag attatcctga ggccagggtg gtaggggtggt   12420
gcctgccagc accctctcag atgtggaaca gggcccgaca tacaggactt ctagctacga   12480
cggttgtatg tgagcgctgc gtgctgtcga gagaagcaca aagcaaaatt agagggaaga   12540
tgcaatgggg agcaattgct ttgtaccctg tctgcacctg gcatgtacct gtgctaatcc   12600
ctccccacag gtcttctttg gcaacgtgga ttcatctggg atcaaacaca atattttttaa   12660
ccctccgatt attgctcagt acatccgttt gcacccaacc cattacagca tccgcagcac   12720
tcttcgcatg gagctcttgg gctgtgactt caacagtaag tgccagtca tcacgtgccc   12780
ttccgtgtcc cagcccccggg tgggatgaat gactgtccta gtcttctcga gggcagggcg   12840
atgtcccagg acacagaacc acgaatgcta agagcagcgc agtcccgagc aaacgcaggc   12900
cttggtcatt gtaaccatgg gattccctag gggcagccac ctcctccggc actcttaagg   12960
tcaaagtgcc cccgaactga gaagagctga ccagaaggcc cggggcag           13008
```

```
SEQ ID NO: 5              moltype = DNA   length = 1116
FEATURE                   Location/Qualifiers
source                    1..1116
                          mol_type = genomic DNA
                          organism = Homo sapiens
SEQUENCE: 5
atggcggcag cggctgcagg cctgggcggc ggcggcgccg gcccgggacc cgaggccggg   60
gacttcctgg cccgctaccg gctggtatcg aacaagctga agaagcggtt cctgcgggaag   120
ccgaacgtgg cggaggccgg cgagcagttc ggacagctgg gccgggagct gcgcgcccag   180
gagtgtctgc cctacgcggc ctggtgccag ctggcggtgg cgcgctgcca gcaggcgctc   240
ttccacgggc ccggggaggc gctggccctc accgaggccg cccgcctctt cctgcggcag   300
gagcgcgacg cgcgccagcg cctggtctgc cccgccgcct acggggagcc gctgcaggcc   360
gccgccagcg ccctgggcgc cgcggtgcgt ctgcacctcg agctgggcca gccggccgcc   420
gccgccgccc tctgcctcga gctggccgcc gccctgcgcg acctgggcca gccggccgcc   480
gccgccggtc acttccagcg cgccgcccag ctccagctgc cccagctgcc cctgccgcg   540
ctgcaggcgc ttggcgaggc cgcctcctgc cagctgctgg cgcgcgacta caccggcgac   600
ctggcggtct tcacgcgcat gcagcgcctg cgcgggagc acggcagcca cccggtgcag   660
tcactgccgc cgcccccgcc gccggcaccc cagcccgggc ccggggcgac gcccgcccta   720
ccggccgcgc tgcttcctcc gaactccggc tcggcggcgc cctctcccgc cgccctgggc   780
gccttctcgg acgtgctggt ccgctgcgag gtgtcccgcg tgctgctgct gctgctgctg   840
caaccaccgc ccgccaagct gctgccggag cacgcccaga ccctgagaa gtactcctg   900
gaggcttttg acagccacgg gcaggagagc agcggccagc ttcccgagga gctctttctg   960
ctgctccagt ctttggtcat ggctacccac gaaaaggaca cggaagccat caagtcgctg   1020
caggtggaga tgtggccact gttgactgct gagcagaacc acctccttca cctcgttctg   1080
caagaaacca tctccccctc aggacaggga gtctga                        1116
```

```
SEQ ID NO: 6              moltype = DNA   length = 1349
FEATURE                   Location/Qualifiers
source                    1..1349
                          mol_type = genomic DNA
                          organism = Canis lupus
                          sub_species = familiaris
SEQUENCE: 6
atgcgcgggg tccgcggggg ggcggggccc gcaggggggcg gggccggggg acgcgggcac   60
gtcgggcgtg cgcgcgtgcg ggcaagatgg cggcggcggc ggcgggcggc ccgggcgcgcg   120
```

-continued

```
gcggcggcgg cggcccgggc ggcggcggcg gcggcggcgg cggcggcgcg ggcccggggc    180
ccgaggccgg ggacttcctg gcccgctacc ggcaggtgtc gagcaagctg cgtaagcggt    240
tcctgcggaa gccgaacgtg gcggaggcgg gcgagcagtt cgcgcagctg ggccgggagc    300
tgcgcgcgca ggagtgcctg ccgtacgccg cgtggtgcca gctggccgtg gcgcgctgcc    360
agcaggcgct gttccacggg cccggggagg cgctggccgt gaccgaggcc gcgcgcctct    420
tcctgcggca ggagcgcgac gcccgccagc gcctcgcctg ccccgcgcc tacggggagc     480
cgctgcaggc cgccgccagc gcgctggggc ccgccgtgcg cctgcacctg gagctgggcc    540
agccggccgc cgccgccggc ctgtgcctcg agctggccgc cgccctgcgc gacctgggcc    600
agccggccgc cgccgccggc cacttcctgc gcgccgcgca gctgcacctg ccgcagctgc    660
ccctggccgc gctgcaggcg ctgggcgacg ccgcctcctg ccagctgctg gcgcgcgact    720
acagcggcgc cctggccgtc ttcacgcgca tgcagcgcct ggcgcgggag cacggcagcc    780
acccgctgcg gcagccgccc ccggccccgc cgccgcccgc ccgccgctg ccctggccc      840
cgccggcggc ggcgtcgacc tcgtcggcct cggcctcgac ctcgtcggcc tcggcctcgt    900
cctcgtcggc ctccgcccg ctgggccccg ccgccgcccg cccgccgccc ccgccgccc     960
tgctgcctgc cgcgcccgcg cccacgccca cgcccgcgcc cgccacgctg ggcgcccttc    1020
cggacgtgct ggtccgctgc gaggtgtccc gcgtgctgct gctgctcctg ctgcagccgc    1080
cgcccgccaa gctgctgccc gagcacgccc acacgctgga gaagtactcc tgggaggcct    1140
tcgacggcca cgggcccgac ggcgcggcca gcttcccga cgagctgttc ctgctgctcc     1200
agtccctggt catggccacc cacgagaagg acacggaggc cgtcaagtcg ctgcaggtgg    1260
acatgtggcc gctgctcagt gcggagcaga accacctgct gcacctcgtt ctgcaggaag    1320
ccgtgtcccc gtcggggcag ggcgtctga                                       1349
```

```
SEQ ID NO: 7              moltype = DNA   length = 22
FEATURE                   Location/Qualifiers
variation                 22
                          note = n = c or g
source                    1..22
                          mol_type = genomic DNA
                          organism = Homo sapiens
SEQUENCE: 7
ctcccaggag tacttctcca gn                                                 22
```

```
SEQ ID NO: 8              moltype = DNA   length = 22
FEATURE                   Location/Qualifiers
variation                 22
                          note = n = c or g
source                    1..22
                          mol_type = genomic DNA
                          organism = Homo sapiens
SEQUENCE: 8
gagggtcctc atgaagaggt cn                                                 22
```

```
SEQ ID NO: 9              moltype = DNA   length = 22
FEATURE                   Location/Qualifiers
source                    1..22
                          mol_type = genomic DNA
                          organism = Homo sapiens
SEQUENCE: 9
ctcccaggag tacttctcca gg                                                 22
```

```
SEQ ID NO: 10             moltype = DNA   length = 22
FEATURE                   Location/Qualifiers
source                    1..22
                          mol_type = genomic DNA
                          organism = Homo sapiens
SEQUENCE: 10
gagggtcctc atgaagaggt cc                                                 22
```

```
SEQ ID NO: 11             moltype = DNA   length = 22
FEATURE                   Location/Qualifiers
source                    1..22
                          mol_type = genomic DNA
                          organism = Canis lupus
                          sub_species = familiaris
SEQUENCE: 11
ctcccaggag tacttctcca gc                                                 22
```

```
SEQ ID NO: 12             moltype = DNA   length = 22
FEATURE                   Location/Qualifiers
source                    1..22
                          mol_type = genomic DNA
                          organism = Canis lupus
                          sub_species = familiaris
SEQUENCE: 12
gagggtcctc atgaagaggt cg                                                 22
```

```
SEQ ID NO: 13             moltype = AA   length = 354
FEATURE                   Location/Qualifiers
REGION                    1..354
```

```
                            note = Synthesized
source                      1..354
                            mol_type = protein
                            organism = synthetic construct
SEQUENCE: 13
MNTKYNKEFL LYLAGFVDGD GSIYASIKPH QSVKFKHELR LGFSVGQKTQ RRWFLDKLVD  60
EIGVGYVRDK GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDA DGSIYAAIQP EQSSKFKHTL RLCFDVSQKT  240
QRRWFLDKLV DEIGVGYVRD AGSVSHYVLS EIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 14          moltype = AA   length = 354
FEATURE                Location/Qualifiers
REGION                 1..354
                       note = Synthesized
source                 1..354
                       mol_type = protein
                       organism = synthetic construct
SEQUENCE: 14
MNTKYNKEFL LYLAGFVDGD GSIYASIKPR QDLKFKHELR LGFSVGQKTQ RRWFLDKLVD  60
EIGVGYVRDK GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDS DGSIYACIEP QQRMKFKHAL RLSFNVSQKT  240
QRRWFLDKLV DEIGVGYVRD NGSVSHYSLS EIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 15          moltype = AA   length = 354
FEATURE                Location/Qualifiers
REGION                 1..354
                       note = Synthesized
source                 1..354
                       mol_type = protein
                       organism = synthetic construct
SEQUENCE: 15
MNTKYNKEFL LYLAGFVDGD GSIYASIKPA QDSKFKHNLR LGFSVGQKTQ RRWFLDKLVD  60
EIGVGYVRDK GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDA DGSIYATIQP EQSGKFKHTL RLCFDVSQKT  240
QRRWFLDKLV DEIGVGYVRD AGSVSHYVLS EIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 16          moltype = AA   length = 354
FEATURE                Location/Qualifiers
REGION                 1..354
                       note = Synthesized
source                 1..354
                       mol_type = protein
                       organism = synthetic construct
SEQUENCE: 16
MNTKYNKEFL LYLAGFVDGD GSIYASIKPA QDSKFKHNLR LGFSVGQKTQ RRWFLDKLVD  60
EIGVGYVRDK GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDA DGSIYATIEP EQDVKFKHTL RLVFNVSQKT  240
QRRWLLDKLV DEIGVGYVND KGSVSSYTLS KIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 17          moltype = AA   length = 354
FEATURE                Location/Qualifiers
REGION                 1..354
                       note = Synthesized
source                 1..354
                       mol_type = protein
                       organism = synthetic construct
SEQUENCE: 17
MNTKYNKEFL LYLAGFVDGD GSIYASIKPA QDSKFKHNLR LGFSVGQKTQ RRWFLDKLVD  60
EIGVGYVRDK GSVSEYLLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDS DGSIYASIEP NQSPKFKHYL RLAFNVSQKT  240
QRRWFLDKLV DEIGVGYVRD QGSVSHYTLS QIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 18          moltype = AA   length = 354
FEATURE                Location/Qualifiers
REGION                 1..354
                       note = Synthesized
source                 1..354
                       mol_type = protein
                       organism = synthetic construct
```

-continued

```
SEQUENCE: 18
MNTKYNKEFL LYLAGFVDGD GSIYASIKPA QDSKFKHNLR LGFSVGQKTQ RRWFLDKLVD   60
EIGVGYVRDK GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDS DGSIYACIEP QQRVKFKHAL RLSFNVSQKT  240
QRRWFLDKLV DEIGVGYVRD NGSVSHYQLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 19                moltype = AA   length = 354
FEATURE                      Location/Qualifiers
REGION                       1..354
                             note = Synthesized
source                       1..354
                             mol_type = protein
                             organism = synthetic construct
SEQUENCE: 19
MNTKYNKEFL LYLAGFVDGD GSIYASIKPH QDLKFKHELR LGFEVSQKTQ RRWFLDKLVD   60
EIGVGYVRDR GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDA DGSIYAAIQP DQEVKFKHVL RLCFDVSQKT  240
QRRWFLDKLV DEIGVGYVRD ASSVSHYVLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 20                moltype = AA   length = 354
FEATURE                      Location/Qualifiers
REGION                       1..354
                             note = Synthesized
source                       1..354
                             mol_type = protein
                             organism = synthetic construct
SEQUENCE: 20
MNTKYNKEFL LYLAGFVDGD GSIYASIKPH QDLKFKHELR LGFEVSQKTQ RRWFLDKLVD   60
EIGVGYVRDR GSVSEYLLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDA DGSIYAAIQP DQEVKFKHVL RLCFDVSQKT  240
QRRWFLDKLV DEIGVGYVRD AGSVSHYVLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 21                moltype = AA   length = 354
FEATURE                      Location/Qualifiers
REGION                       1..354
                             note = Synthesized
source                       1..354
                             mol_type = protein
                             organism = synthetic construct
SEQUENCE: 21
MNTKYNKEFL LYLAGFVDGD GSIYASIKPH QDLKFKHELR LGFEVGQKTQ RRWFLDKLVD   60
EIGVGYVRDR GSVSHYLLSQ IKPLHNFLTQ LQPFLKLKQK QANLVLKIIE QLPSAKESPD  120
KFLEVCTWVD QIAALNDSKT RKTTSETVRA VLDSLPGSVG GLSSSQASSA ASSASSSPGS  180
GISEALRAGA GSGTGYNKEF LLYLAGFVDA DGSIYAAIQP DQKVKFKHVL RLCFDVSQKT  240
QRRWFLDKLV DEIGVGYVRD AYPCAHYVLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 22                moltype = AA   length = 147
FEATURE                      Location/Qualifiers
REGION                       1..147
                             note = Synthesized
source                       1..147
                             mol_type = protein
                             organism = synthetic construct
SEQUENCE: 22
KEFLLYLAGF VDGDGSIYAS IKPHQSVKFK HELRLGFSVG QKTQRRWFLD KLVDEIGVGY   60
VRDKGSVSEY LLSQIKPLHN FLTQLQPFLK LKQKQANLVL KIIEQLPSAK ESPDKFLEVC  120
TWVDQIAALN DSKTRKTTSE TVRAVLD                                     147

SEQ ID NO: 23                moltype = AA   length = 147
FEATURE                      Location/Qualifiers
REGION                       1..147
                             note = Synthesized
source                       1..147
                             mol_type = protein
                             organism = synthetic construct
SEQUENCE: 23
KEFLLYLAGF VDGDGSIYAS IKPRQDLKFK HELRLGFSVG QKTQRRWFLD KLVDEIGVGY   60
VRDKGSVSEY LLSQIKPLHN FLTQLQPFLK LKQKQANLVL KIIEQLPSAK ESPDKFLEVC  120
TWVDQIAALN DSKTRKTTSE TVRAVLD                                     147

SEQ ID NO: 24                moltype = AA   length = 147
FEATURE                      Location/Qualifiers
```

-continued

```
REGION                    1..147
                          note = Synthesized
source                    1..147
                          mol_type = protein
                          organism = synthetic construct
SEQUENCE: 24
KEFLLYLAGF VDGDGSIYAS IKPAQDSKFK HNLRLGFSVG QKTQRRWFLD KLVDEIGVGY  60
VRDKGSVSEY LLSQIKPLHN FLTQLQPFLK LKQKQANLVL KIIEQLPSAK ESPDKFLEVC 120
TWVDQIAALN DSKTRKTTSE TVRAVLD                                     147

SEQ ID NO: 25             moltype = AA   length = 147
FEATURE                   Location/Qualifiers
REGION                    1..147
                          note = Synthesized
source                    1..147
                          mol_type = protein
                          organism = synthetic construct
SEQUENCE: 25
KEFLLYLAGF VDGDGSIYAS IKPAQDSKFK HNLRLGFSVG QKTQRRWFLD KLVDEIGVGY  60
VRDKGSVSEY LLSQIKPLHN FLTQLQPFLK LKQKQANLVL KIIEQLPSAK ESPDKFLEVC 120
TWVDQIAALN DSKTRKTTSE TVRAVLD                                     147

SEQ ID NO: 26             moltype = AA   length = 147
FEATURE                   Location/Qualifiers
REGION                    1..147
                          note = Synthesized
source                    1..147
                          mol_type = protein
                          organism = synthetic construct
SEQUENCE: 26
KEFLLYLAGF VDGDGSIYAS IKPAQDSKFK HNLRLGFSVG QKTQRRWFLD KLVDEIGVGY  60
VRDKGSVSEY LLSEIKPLHN FLTQLQPFLK LKQKQANLVL KIIEQLPSAK ESPDKFLEVC 120
TWVDQIAALN DSKTRKTTSE TVRAVLD                                     147

SEQ ID NO: 27             moltype = AA   length = 147
FEATURE                   Location/Qualifiers
REGION                    1..147
                          note = Synthesized
source                    1..147
                          mol_type = protein
                          organism = synthetic construct
SEQUENCE: 27
KEFLLYLAGF VDGDGSIYAS IKPAQDSKFK HNLRLGFSVG QKTQRRWFLD KLVDEIGVGY  60
VRDKGSVSEY LLSQIKPLHN FLTQLQPFLK LKQKQANLVL KIIEQLPSAK ESPDKFLEVC 120
TWVDQIAALN DSKTRKTTSE TVRAVLD                                     147

SEQ ID NO: 28             moltype = AA   length = 147
FEATURE                   Location/Qualifiers
REGION                    1..147
                          note = Synthesized
source                    1..147
                          mol_type = protein
                          organism = synthetic construct
SEQUENCE: 28
KEFLLYLAGF VDGDGSIYAS IKPHQDLKFK HELRLGFEVS QKTQRRWFLD KLVDEIGVGY  60
VRDRGSVSEY LLSQIKPLHN FLTQLQPFLK LKQKQANLVL KIIEQLPSAK ESPDKFLEVC 120
TWVDQIAALN DSKTRKTTSE TVRAVLD                                     147

SEQ ID NO: 29             moltype = AA   length = 147
FEATURE                   Location/Qualifiers
REGION                    1..147
                          note = Synthesized
source                    1..147
                          mol_type = protein
                          organism = synthetic construct
SEQUENCE: 29
KEFLLYLAGF VDGDGSIYAS IKPHQDLKFK HELRLGFEVS QKTQRRWFLD KLVDEIGVGY  60
VRDRGSVSEY LLSQIKPLHN FLTQLQPFLK LKQKQANLVL KIIEQLPSAK ESPDKFLEVC 120
TWVDQIAALN DSKTRKTTSE TVRAVLD                                     147

SEQ ID NO: 30             moltype = AA   length = 147
FEATURE                   Location/Qualifiers
REGION                    1..147
                          note = Synthesized
source                    1..147
                          mol_type = protein
                          organism = synthetic construct
SEQUENCE: 30
KEFLLYLAGF VDGDGSIYAS IKPHQDLKFK HELRLGFEVG QKTQRRWFLD KLVDEIGVGY  60
```

```
VRDRGSVSHY LLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 31              moltype = AA  length = 147
FEATURE                    Location/Qualifiers
REGION                     1..147
                           note = Synthesized
source                     1..147
                           mol_type = protein
                           organism = synthetic construct
SEQUENCE: 31
KEFLLYLAGF VDADGSIYAA IQPEQSSKFK HTLRLCFDVS QKTQRRWFLD KLVDEIGVGY   60
VRDAGSVSHY VLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 32              moltype = AA  length = 147
FEATURE                    Location/Qualifiers
REGION                     1..147
                           note = Synthesized
source                     1..147
                           mol_type = protein
                           organism = synthetic construct
SEQUENCE: 32
KEFLLYLAGF VDSDGSIYAC IEPQQRMKFK HALRLSFNVS QKTQRRWFLD KLVDEIGVGY   60
VRDNGSVSHY SLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 33              moltype = AA  length = 147
FEATURE                    Location/Qualifiers
REGION                     1..147
                           note = Synthesized
source                     1..147
                           mol_type = protein
                           organism = synthetic construct
SEQUENCE: 33
KEFLLYLAGF VDADGSIYAT IQPEQSGKFK HTLRLCFDVS QKTQRRWFLD KLVDEIGVGY   60
VRDAGSVSHY VLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 34              moltype = AA  length = 147
FEATURE                    Location/Qualifiers
REGION                     1..147
                           note = Synthesized
source                     1..147
                           mol_type = protein
                           organism = synthetic construct
SEQUENCE: 34
KEFLLYLAGF VDADGSIYAT IEPEQDVKFK HTLRLVFNVS QKTQRRWLLD KLVDEIGVGY   60
VNDKGSVSSY TLSIKPLHN FLTQLQPFLK LKQKQANLVL KIIEQLPSAK ESPDKFLEVC    120
TWVDQIAALN DSKTRKTTSE TVRAVLD                                       147

SEQ ID NO: 35              moltype = AA  length = 147
FEATURE                    Location/Qualifiers
REGION                     1..147
                           note = Synthesized
source                     1..147
                           mol_type = protein
                           organism = synthetic construct
SEQUENCE: 35
KEFLLYLAGF VDSDGSIYAS IEPNQSPKFK HYLRLAFNVS QKTQRRWFLD KLVDEIGVGY   60
VRDQGSVSHY TLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 36              moltype = AA  length = 147
FEATURE                    Location/Qualifiers
REGION                     1..147
                           note = Synthesized
source                     1..147
                           mol_type = protein
                           organism = synthetic construct
SEQUENCE: 36
KEFLLYLAGF VDSDGSIYAC IEPQQRVKFK HALRLSFNVS QKTQRRWFLD KLVDEIGVGY   60
VRDNGSVSHY QLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 37              moltype = AA  length = 147
FEATURE                    Location/Qualifiers
REGION                     1..147
                           note = Synthesized
```

```
source                   1..147
                         mol_type = protein
                         organism = synthetic construct
SEQUENCE: 37
KEFLLYLAGF VDADGSIYAA IQPDQEVKFK HVLRLCFDVS QKTQRRWFLD KLVDEIGVGY   60
VRDASSVSHY VLSEIKPLHN FLTQLQPFLK LKQKQANLVL KIIEQLPSAK ESPDKFLEVC  120
TWVDQIAALN DSKTRKTTSE TVRAVLD                                      147

SEQ ID NO: 38            moltype = AA  length = 147
FEATURE                  Location/Qualifiers
REGION                   1..147
                         note = Synthesized
source                   1..147
                         mol_type = protein
                         organism = synthetic construct
SEQUENCE: 38
KEFLLYLAGF VDADGSIYAA IQPDQEVKFK HVLRLCFDVS QKTQRRWFLD KLVDEIGVGY   60
VRDAGSVSHY VLSEIKPLHN FLTQLQPFLK LKQKQANLVL KIIEQLPSAK ESPDKFLEVC  120
TWVDQIAALN DSKTRKTTSE TVRAVLD                                      147

SEQ ID NO: 39            moltype = AA  length = 147
FEATURE                  Location/Qualifiers
REGION                   1..147
                         note = Synthesized
source                   1..147
                         mol_type = protein
                         organism = synthetic construct
SEQUENCE: 39
KEFLLYLAGF VDADGSIYAA IQPDQKVKFK HVLRLCFDVS QKTQRRWFLD KLVDEIGVGY   60
VRDAYPCAHY VLSEIKPLHN FLTQLQPFLK LKQKQANLVL KIIEQLPSAK ESPDKFLEVC  120
TWVDQIAALN DSKTRKTTSE TVRAVLD                                      147

SEQ ID NO: 40            moltype = DNA  length = 38
FEATURE                  Location/Qualifiers
misc_feature             1..38
                         note = Synthesized
source                   1..38
                         mol_type = other DNA
                         organism = synthetic construct
SEQUENCE: 40
cccttacagt tattaactac tctcatgagg ttcattcc                           38

SEQ ID NO: 41            moltype = DNA  length = 39
FEATURE                  Location/Qualifiers
misc_feature             1..39
                         note = Synthesized
source                   1..39
                         mol_type = other DNA
                         organism = synthetic construct
SEQUENCE: 41
ggccctacaa ccattctgcc tttcactttc agtgcaata                          39

SEQ ID NO: 42            moltype = DNA  length = 36
FEATURE                  Location/Qualifiers
misc_feature             1..36
                         note = Synthesized
source                   1..36
                         mol_type = other DNA
                         organism = synthetic construct
SEQUENCE: 42
cacaaggggg aagagtgtga gggtgtggga taagaa                             36

SEQ ID NO: 43            moltype = DNA  length = 18
FEATURE                  Location/Qualifiers
misc_feature             1..18
                         note = Synthesized
source                   1..18
                         mol_type = other DNA
                         organism = synthetic construct
SEQUENCE: 43
gagccagttg tgtaccat                                                 18

SEQ ID NO: 44            moltype = DNA  length = 20
FEATURE                  Location/Qualifiers
misc_feature             1..20
                         note = Synthesized
source                   1..20
                         mol_type = other DNA
                         organism = synthetic construct
```

```
SEQUENCE: 44
acgtgatccc gatttgaata                                      20

SEQ ID NO: 45          moltype = DNA   length = 18
FEATURE                Location/Qualifiers
misc_feature           1..18
                       note = Synthesized
source                 1..18
                       mol_type = other DNA
                       organism = synthetic construct
SEQUENCE: 45
gcaccttact gtcctgat                                        18

SEQ ID NO: 46          moltype = DNA   length = 22
FEATURE                Location/Qualifiers
source                 1..22
                       mol_type = genomic DNA
                       organism = Homo sapiens
SEQUENCE: 46
ttcccagtag tacttctcca gt                                   22

SEQ ID NO: 47          moltype = DNA   length = 17
FEATURE                Location/Qualifiers
misc_feature           1..17
                       note = Synthesized
source                 1..17
                       mol_type = other DNA
                       organism = synthetic construct
SEQUENCE: 47
tctggatggc aacaagt                                         17

SEQ ID NO: 48          moltype =    length =
SEQUENCE: 48
000

SEQ ID NO: 49          moltype = DNA   length = 16
FEATURE                Location/Qualifiers
misc_feature           1..16
                       note = Synthesized
source                 1..16
                       mol_type = other DNA
                       organism = synthetic construct
SEQUENCE: 49
agaccattaa ggtccc                                          16

SEQ ID NO: 50          moltype = DNA   length = 19
FEATURE                Location/Qualifiers
misc_feature           1..19
                       note = Synthesized
source                 1..19
                       mol_type = other DNA
                       organism = synthetic construct
SEQUENCE: 50
tgatcccaga tgaatccac                                       19
```